United States Patent
Parsy et al.

(10) Patent No.: US 8,309,737 B2
(45) Date of Patent: Nov. 13, 2012

(54) PHOSPHINATE RUTHENIUM COMPLEXES

(75) Inventors: Christophe Claude Parsy, Jacou (FR); Francois-Rene Alexandre, Montpellier (FR); Florence Marie-Emilie Bonnaterre, Romainville (FR); Dominique Surleraux, Wauthier-Braine (BE)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/146,877

(22) PCT Filed: Feb. 2, 2010

(86) PCT No.: PCT/US2010/022798
§ 371 (c)(1),
(2), (4) Date: Sep. 26, 2011

(87) PCT Pub. No.: WO2010/090976
PCT Pub. Date: Aug. 12, 2010

(65) Prior Publication Data
US 2012/0041191 A1    Feb. 16, 2012

Related U.S. Application Data

(60) Provisional application No. 61/149,662, filed on Feb. 3, 2009, provisional application No. 61/231,408, filed on Aug. 5, 2009.

(51) Int. Cl.
    *C07F 15/00* (2006.01)
(52) U.S. Cl. ......................................... 548/103
(58) Field of Classification Search .................. 540/460; 548/103; 568/15; 564/12; 560/122
    See application file for complete search history.

(56) References Cited

U.S. PATENT DOCUMENTS

| | | |
|---|---|---|
| 6,620,955 B1 | 9/2003 | Pederson et al. |
| 6,867,303 B2 | 3/2005 | Grela |
| 7,026,495 B1 | 4/2006 | Pederson et al. |
| 7,268,242 B2 | 9/2007 | Pederson et al. |
| 8,003,659 B2 | 8/2011 | Parsy et al. |
| 2006/0122412 A1 | 6/2006 | Pederson et al. |
| 2007/0043180 A1 | 2/2007 | Zhan |
| 2008/0108841 A1 | 5/2008 | Pederson et al. |

FOREIGN PATENT DOCUMENTS

| | | |
|---|---|---|
| DE | 10335417 A1 | 2/2005 |
| WO | 03044060 A2 | 5/2003 |
| WO | 2004035596 A1 | 4/2004 |
| WO | 2005053843 A1 | 6/2005 |
| WO | 2007054483 A1 | 5/2007 |
| WO | 2007140954 A1 | 12/2007 |
| WO | 2008065187 A1 | 5/2008 |
| WO | 2009099596 A2 | 8/2009 |

OTHER PUBLICATIONS

Wallace et al., "A double ring closing metathesis reaction in the rapid, enantioselective synthesis of NK-1 receptor antagonists," Org. Lett. 2001, 3, 671-674.
Kanada et al., "Total synthesis of the potent antitumor macrolides pladienolide B and D," Angew. Chem. Int. Ed. 2007, 46, 4350-4355.
Necas et al., "Catalytic deallylation of allyl- and diallylmalonates," J. Am. Chem. Soc. 2004, 126, 10222-10223.
Yao et al., "Poly(fluoroalkyl acrylate)-bound ruthenium carbene complex: a fluorous and recyclable catalyst for ring-closing olefin metathesis," J. Am. Chem. Soc. 2004, 126, 74-75.

*Primary Examiner* — Kristin Bianchi
(74) *Attorney, Agent, or Firm* — Jones Day

(57) ABSTRACT

Provided herein are ruthenium complexes of Formula (I), and processes of preparation thereof. Also provided are methods of their use as a metathesis catalyst.

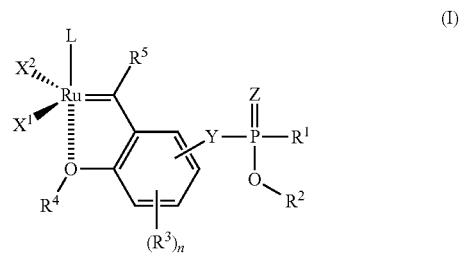

(I)

38 Claims, No Drawings

PHOSPHINATE RUTHENIUM COMPLEXES

CROSS REFERENCE TO RELATED APPLICATIONS

This application is a 371 of International Patent Application No. PCT/US2010/022798, filed on Feb. 2, 2010, which claims priority to U.S. Provisional Application Nos. 61/149,662, filed Feb. 3, 2009, and 61/231,408, filed Aug. 5, 2009, the disclosure of each of which is incorporated herein by reference in its entirety.

FIELD

Provided herein are ruthenium complexes, and processes of preparation thereof. Also provided are methods of their use as a metathesis catalyst.

BACKGROUND

Olefin metathesis provides an efficient method for the construction of carbon-carbon double bonds and has emerged as a powerful tool in preparation of cyclic organic molecules and polymeric materials. Some common olefin metathesis reactions include ring closure metathesis (RCM), acyclic diene metathesis polymerization (ADMET), ring opening metathesis polymerization (ROMP), ring opening metathesis (ROM), and cross metathesis (CM).

In recent years, olefin metathesis has been increasingly used by the pharmaceutical industry to synthesize biologically active molecules (Wallace et al., "A Double Ring Closing Metathesis Reaction in the Rapid, Enantioselective Synthesis of NK-1 Receptor Antagonists," *Org. Lett.* 2001, 3, 671-674; Kanada et al., "Total Synthesis of the Potent Antitumor macrolides Pladienolide B and D," *Angew. Chem., Int. Ed.* 2007, 46, 4350-4355). The increasing use of olefin metathesis in pharmaceutical industry has increased the demand for more efficient olefin metathesis catalysts.

SUMMARY OF THE DISCLOSURE

Provided herein is a ruthenium complex of Formula I:

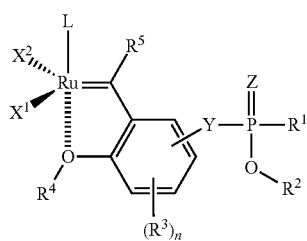

(I)

wherein:

L is a neutral ligand;

$R^1$ is $C_{1-12}$ alkyl, $C_{3-10}$ cycloalkyl, $C_{6-14}$ aryl, heteroaryl, heterocyclyl, or —$NR^{3b}R^{3c}$;

$R^2$ is H, $C_{1-12}$ alkyl, $C_{3-10}$ cycloalkyl, or $C_{6-14}$ aryl;

$R^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —$C(O)R^{3a}$, —$C(O)OR^{3a}$, —$C(O)NR^{3b}R^{3c}$, —$OR^{3a}$, —$NR^{3b}R^{3c}$, —$NR^{3a}C(O)R^{3b}$, —$NR^{3a}C(O)OR^{3b}$, —$NR^{3a}S(O)_2R^{3b}$, —$PR^{3a}R^{3b}$, —$P(OR^{3a})R^{3b}$, —$P(OR^{3a})(OR^{3b})$, —$P(O)R^{3a}R^{3b}$, —$P(O)(OR^{3a})R^{3b}$, —$P(O)(OR^{3a})(OR^{3b})$, —$S(O)_2R^{3a}$, or —$SO_2NR^{3b}R^{3c}$;

$R^4$ is $C_{1-12}$ alkyl, $C_{3-10}$ cycloalkyl, $C_{7-15}$ aralkyl, or —$C(R^{4a}R^{4b})C(O)NR^{4c}R^{4d}$;

$R^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;

each $R^{3a}$ and $R^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each $R^{3b}$ and $R^{3c}$ is independently hydrogen, $C_{1-6}$ alkyl, $C_{2-6}$ alkenyl, $C_{2-6}$ alkynyl, $C_{3-7}$ Cycloalkyl, $C_{6-14}$ aryl, heteroaryl, or heterocyclyl; or $R^{3b}$ and $R^{3c}$ together with the N atom form a heteroaryl or heterocyclyl;

$R^{4a}$ and $R^{4b}$ are each independently hydrogen, $C_{1-6}$ alkyl, $C_{3-8}$ cycloalkyl, $C_{6-14}$ aryl, or $C_{7-15}$ aralkyl;

$R^{4c}$ and $R^{4d}$ are each independently hydrogen, $C_{1-6}$ alkyl, $C_{3-8}$ cycloalkyl, $C_{6-14}$ aryl, or $C_{7-15}$ aralkyl; or $R^{4c}$ and $R^{4d}$ together with the N atom form heterocyclyl;

$X^1$ and $X^2$ are each independently an anionic ligand;

Y is a bond or —$NR^b$—;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —$C(O)R^a$, —$C(O)OR^a$, —$C(O)NR^bR^c$, —$C(NR^a)NR^bR^c$, —$OR^a$, —$OC(O)R^a$, —$OC(O)OR^a$, —$OC(O)NR^bR^c$, —$OC(=NR^a)NR^bR^c$, —$OS(O)R^a$, —$OS(O)_2R^a$, —$OS(O)NR^bR^c$, —$OS(O)_2NR^bR^c$, —$NR^bR^c$, —$NR^aC(O)R^d$, —$NR^aC(O)OR^d$, —$NR^aC(O)NR^bR^c$, —$NR^aC(=NR^d)NR^bR^c$, —$NR^aS(O)R^d$, —$NR^aS(O)_2R^d$, —$NR^aS(O)NR^bR^c$, —$NR^aS(O)_2NR^bR^c$, —$PR^aR^d$, —$P(OR^a)R^d$, —$P(OR^a)(OR^d)$, —$P(O)R^aR^d$, —$P(O)(OR^a)R^d$, —$P(O)(OR^a)(OR^d)$, —$SR^a$, —$S(O)R^a$, —$S(O)_2R^a$, or —$SO_2NR^bR^c$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or $R^b$ and $R^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —$C(O)R^e$, —$C(O)OR^e$, —$C(O)NR^fR^g$, —$C(NR^e)NR^fR^g$, —$OR^e$, —$OC(O)R^e$, —$OC(O)OR^e$, —$OC(O)NR^fR^g$, —$OC(=NR^e)NR^fR^g$, —$OS(O)R^e$, —$OS(O)_2R^e$, —$OS(O)NR^fR^g$, —$OS(O)_2NR^fR^g$, —$NR^fR^g$, —$NR^eC(O)R^h$, —$NR^eC(O)OR^h$, —$NR^eC(O)NR^fR^g$, —$NR^eC(=NR^h)NR^fR^g$, —$NR^eS(O)R^h$, —$NR^eS(O)_2R^h$, —$NR^eS(O)NR^fR^g$, —$NR^eS(O)_2NR^fR^g$, —$PR^eR^h$, —$P(OR^e)R^h$, —$P(OR^e)(OR^h)$, —$P(O)R^eR^h$, —$P(O)(OR^e)R^h$, —$P(O)(OR^e)(OR^h)$, —$SR^e$, —$S(O)R^e$, —$S(O)_2R^e$, or —$S(O)_2NR^fR^g$; wherein each $R^e$, $R^f$, $R^g$, and $R^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^f$ and $R^g$ together with the N atom to which they are attached form heterocyclyl.

Also provided herein is a ruthenium complex of Formula I:

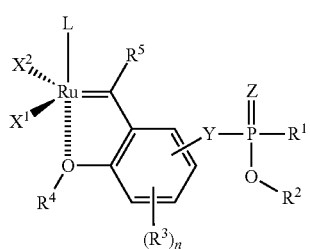

(I)

wherein:

L is a neutral ligand;

$R^1$ is $C_{1-12}$ alkyl, $C_{3-10}$ cycloalkyl, $C_{6-14}$ aryl, heteroaryl, heterocyclyl, or —$NR^{3b}R^{3c}$;

$R^2$ is H, $C_{1-12}$ alkyl, $C_{3-10}$ cycloalkyl, or $C_{6-14}$ aryl;

$R^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —$C(O)R^{3a}$, —$C(O)OR^{3a}$, —$C(O)NR^{3b}R^{3c}$, —$OR^{3a}$, —$NR^{3b}R^{3c}$, —$NR^{3a}C(O)R^{3b}$, —$NR^{3a}C(O)OR^{3b}$, —$NR^{3a}S(O)_2R^{3b}$, —$PR^{3a}R^{3b}$, —$P(OR^{3a})R^{3b}$, —$P(OR^{3a})(OR^{3b})$, —$P(O)R^{3a}R^{3b}$, —$P(O)(OR^{3a})R^{3b}$, —$P(O)(OR^{3a})(OR^{3b})$, —$S(O)_2R^{3a}$, or —$SO_2NR^{3b}R^{3c}$, $R^4$ is $C_{1-12}$ alkyl, $C_{3-10}$ cycloalkyl, or $C_{7-15}$ aralkyl;

$R^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;

$X^1$ and $X^2$ are each independently an anionic ligand;

Y is a bond or —$NR^b$—;

Z is O or S;

n is an integer of 0, 1, 2, or 3;

each $R^{3a}$ and $R^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; and each $R^{3b}$ and $R^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{3b}$ and $R^{3c}$ together with the N atom form a heteroaryl or heterocyclyl;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —$C(O)R^a$, —$C(O)OR^a$, —$C(O)NR^bR^c$, —$C(NR^a)NR^bR^c$, —$OR^a$, —$OC(O)R^a$, —$OC(O)OR^a$, —$OC(O)NR^bR^c$, —$OC(=NR^a)NR^bR^c$, —$OS(O)R^a$, —$OS(O)_2R^a$, —$OS(O)NR^bR^c$, —$OS(O)_2NR^bR^c$, —$NR^bR^c$, —$NR^aC(O)R^d$, —$NR^aC(O)OR^d$, —$NR^aC(O)NR^bR^c$, —$NR^aC(=NR^d)NR^bR^c$, —$NR^aS(O)R^d$, —$NR^aS(O)_2R^d$, —$NR^aS(O)NR^bR^c$, —$NR^aS(O)_2NR^bR^c$, —$PR^aR^d$, —$P(OR^a)R^d$, —$P(OR^a)(OR^d)$, —$P(O)R^aR^d$, —$P(O)(OR^a)R^d$, —$P(O)(OR^a)(OR^d)$, —$SR^a$, —$S(O)R^a$, —$S(O)_2R^a$, or —$SO_2NR^bR^c$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or $R^b$ and $R^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —$C(O)R^e$, —$C(O)OR^e$, —$C(O)NR^fR^g$, —$C(NR^e)NR^fR^g$, —$OR^e$, $OC(O)R^e$, —$OC(O)OR^e$, —$OC(O)NR^fR^g$, —$OC(=NR^e)NR^fR^g$, —$OS(O)R^e$, —$OS(O)_2R^e$, —$OS(O)NR^fR^g$, —$OS(O)_2NR^fR^g$, —$NR^fR^g$, —$NR^eC(O)R^h$, —$NR^eC(O)OR^h$, —$NR^eC(O)NR^fR^g$, —$NR^eC(=NR^h)NR^fR^g$, —$NR^eS(O)R^h$, —$NR^eS(O)_2R^h$, —$NR^eS(O)NR^fR^g$, —$NR^eS(O)_2NR^fR^g$, —$PR^eR^h$, —$P(OR^e)R^h$, —$P(OR^e)(OR^h)$, —$P(O)R^eR^h$, —$P(O)(OR^e)R^h$, —$P(O)(OR^e)(OR^h)$, —$S(O)R^e$, —$S(O)_2R^e$, or —$S(O)_2NR^fR^g$; wherein each $R^e$, $R^f$, $R^g$, and $R^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^f$ and $R^g$ together with the N atom to which they are attached form heterocyclyl.

Further provided herein is a compound of Formula II:

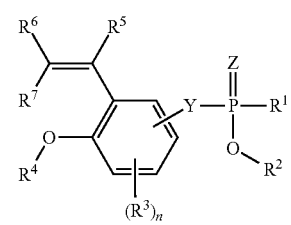

(II)

wherein:

$R^1$ is $C_{1-12}$ alkyl, $C_{3-10}$ cycloalkyl, $C_{6-14}$ aryl, heteroaryl, heterocyclyl, or —$NR^{3b}R^{3c}$;

$R^2$ is H, $C_{1-12}$ alkyl, $C_{3-10}$ cycloalkyl, or $C_{6-14}$ aryl;

$R^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —$C(O)R^{3a}$, —$C(O)OR^{3a}$, —$C(O)NR^{3b}R^{3c}$, —$OR^{3a}$, —$NR^{3b}R^{3c}$, —$NR^{3a}C(O)R^{3b}$, —$NR^{3a}C(O)OR^{3b}$, —$NR^{3a}S(O)_2R^{3b}$, —$PR^{3a}R^{3b}$, —$P(OR^{3a})R^{3b}$, —$P(OR^{3a})(OR^{3b})$, —$P(O)R^{3a}R^{3b}$, —$P(O)(OR^{3a})R^{3b}$, —$P(O)(OR^{3a})(OR^{3b})$, —$S(O)_2R^{3a}$, or —$SO_2NR^{3b}R^{3c}$.

$R^4$ is $C_{1-12}$ alkyl, $C_{3-10}$ cycloalkyl, $C_{7-15}$ aralkyl, or —$C(R^{4a}R^{4b})C(O)NR^{4c}R^{4d}$;

$R^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;

$R^6$ and $R^7$ are independently hydrogen or $C_{1-6}$ alkyl;

each $R^{3a}$ and $R^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each $R^{3b}$ and $R^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{3b}$ and $R^{3c}$ together with the N atom form a heteroaryl or heterocyclyl;

$R^{4a}$ and $R^{4b}$ are each independently hydrogen, $C_{1-6}$ alkyl, $C_{3-8}$ cycloalkyl, $C_{6-14}$ aryl, or $C_{7-15}$ aralkyl;

$R^{4c}$ and $R^{4d}$ are each independently hydrogen, $C_{1-6}$ alkyl, $C_{3-8}$ cycloalkyl, $C_{6-14}$ aryl, or $C_{7-15}$ aralkyl; or $R^{4c}$ and $R^{4d}$ together with the N atom form heterocyclyl;

Y is a bond or —$NR^b$—;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —C(O)R$^a$, —C(O)OR$^a$, —C(O)NR$^b$R$^c$, —C(NR$^a$)NR$^b$R$^c$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —PR$^a$R$^d$, —P(OR$^a$)R$^d$, —P(OR$^a$)(OR$^d$), —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, or —SO$_2$NR$^b$R$^c$; wherein each R$^a$, R$^b$, R$^c$, and R$^d$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q; or R$^b$ and R$^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —PR$^e$R$^h$, —P(OR$^e$)R$^h$, —P(OR$^e$)(OR$^h$), —P(O)R$^e$R$^h$, —P(O)(OR$^e$)R$^h$, —P(O)(OR$^e$)(OR$^h$), —SR$^e$, —S(O)R$^e$, —S(O)$_2$R$^e$, or —S(O)$_2$NR$^f$R$^g$; wherein each R$^e$, R$^f$, R$^g$, and R$^h$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or R$^f$ and R$^g$ together with the N atom to which they are attached form heterocyclyl.

Provided herein is a compound of Formula II:

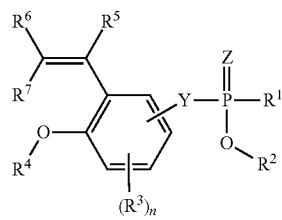

(II)

wherein:
R$^1$ is C$_{1-12}$ alkyl, C$_{3-10}$ cycloalkyl, C$_{6-14}$ aryl, heteroaryl, heterocyclyl, or —NR$^{3b}$R$^{3c}$;
R$^2$ is H, C$_{1-12}$ alkyl, C$_{3-10}$ cycloalkyl, or C$_{6-14}$ aryl;
R$^3$ is halo, cyano, nitro, C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, —C(O)R$^{3a}$, —C(O)OR$^{3a}$, —C(O)NR$^{3b}$R$^{3c}$, —OR$^{3a}$, —NR$^{3b}$R$^{3c}$, —NR$^{3a}$C(O)R$^{3b}$, —NR$^{3a}$C(O)OR$^{3b}$, —NR$^{3a}$S(O)$_2$R$^{3b}$, —PR$^{3a}$R$^{3b}$, —P(OR$^{3a}$)R$^{3b}$, —P(OR$^{3a}$)(OR$^{3b}$), —P(O)R$^{3a}$R$^{3b}$, —P(O)(OR$^{3a}$)R$^{3b}$, —P(O)(OR$^{3a}$)(OR$^{3b}$), —S(O)$_2$R$^{3a}$, or —SO$_2$NR$^{3b}$R$^{3c}$,
R$^4$ is C$_{1-12}$ alkyl, C$_{3-10}$ cycloalkyl, or C$_{7-15}$ aralkyl;
R$^5$ is hydrogen, C$_{1-12}$ alkyl, C$_{2-12}$ alkenyl, C$_{2-12}$ alkynyl, C$_{3-10}$ cycloalkyl, or C$_{6-14}$ aryl;
R$^6$ and R$^7$ are independently hydrogen or C$_{1-6}$ alkyl;
Y is a bond or —NR$^b$—;
Z is O or S;
n is an integer of 0, 1, 2, or 3;

each R$^{3a}$ and R$^{3d}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; and
each R$^{3b}$ and R$^{3c}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or R$^{3b}$ and R$^{3c}$ together with the N atom form a heteroaryl or heterocyclyl;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q; or
(c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, NR$^a$S(O)R$^d$, —NR$^a$S(O)$_2$R$^d$, —NR$^a$S(O)NR$^b$R$^c$, —NR$^a$S(O)$_2$NR$^b$R$^c$, —R$^a$R$^d$, —P(OR$^a$)R$^d$, —P(OR$^a$)(OR$^d$), —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, or —SO$_2$NR$^b$R$^c$; wherein each R$^a$, R$^b$, R$^c$, and R$^d$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q; or R$^b$ and R$^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —PR$^e$R$^h$, —P(OR$^e$)R$^h$, —P(OR$^e$)(OR$^h$), —P(O)R$^e$R$^h$, —P(O)(OR$^e$)R$^h$, —P(O)(OR$^e$)(OR$^h$), —S(O)R$^e$, —S(O)$_2$R$^e$, or —S(O)$_2$NR$^f$R$^g$; wherein each R$^e$, R$^f$, R$^g$, and R$^h$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or R$^f$ and R$^g$ together with the N atom to which they are attached form heterocyclyl.

Furthermore, provided herein is a method for catalyzing an olefin metathesis reaction, comprising the step of contacting an olefin with a ruthenium complex of Formula I.

Also provided herein is a method for catalyzing a ring closure metathesis, comprising the step of contacting a compound having two or more olefin groups with a ruthenium complex of Formula I.

DETAILED DESCRIPTION

To facilitate understanding of the disclosure set forth herein, a number of terms are defined below.

Generally, the nomenclature used herein and the laboratory procedures in chemistry described herein are those well known and commonly employed in the art. Unless defined otherwise, all technical and scientific terms used herein generally have the same meaning as commonly understood by one of ordinary skill in the art to which this disclosure belongs.

The term "alkyl" refers to a linear or branched saturated monovalent hydrocarbon radical, wherein the alkyl may optionally be substituted as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkenyl" refers to a linear or branched monovalent hydrocarbon radical, which contains one or more, in one embodiment, one to five, in another embodiment, one, carbon-carbon double bond(s). The alkenyl may be optionally substituted as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one to five, in another embodiment, one, carbon-carbon triple bond(s). The alkynyl may be optionally substituted as described herein. For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl ($-C\equiv CH$), propynyl (including all isomeric forms, e.g., 1-propynyl ($-C\equiv CCH_3$) and propargyl ($-CH_2C\equiv CH$)), butynyl (including all isomeric foams, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "cycloalkyl" refers to a cyclic monovalent hydrocarbon radical, which may be optionally substituted as described herein. In one embodiment, cycloalkyl groups may be saturated or unsaturated but non-aromatic, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "aryl" refers to a monovalent monocyclic aromatic group and/or monovalent multicyclic aromatic group that contain at least one aromatic carbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, aralkyl are optionally substituted with one or more substituents as described herein.

The term "heteroaryl" refers to a monovalent monocyclic aromatic group or monovalent multicyclic aromatic group that contain at least one aromatic ring, wherein at least one aromatic ring contains one or more heteroatoms independently selected from O, S, and N in the ring. Heteroaryl groups are bonded to the rest of a molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein.

The term "heterocyclyl" or "heterocyclic" refers to a monovalent monocyclic non-aromatic ring system or monovalent multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "halogen", "halide" or "halo" refers to fluorine, chlorine, bromine, and/or iodine.

The term "optionally substituted" is intended to mean that a group, such as an alkyl, alkenyl, alkynyl, cycloalkyl, aryl, aralkyl, heteroaryl, or heterocyclyl group, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents Q; and (b) halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —PR$^a$R$^d$, —P(OR$^a$)R$^d$, —P(OR$^a$)(OR$^d$), —P(O)R$^a$R$^d$, —P(O)(OR$^a$)R$^d$, —P(O)(OR$^a$)(OR$^d$), —SR$^a$, S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (iii) R$^b$ and R$^c$ together with the N atom to which they are attached form heteroaryl or heterocyclyl, optionally substituted with one or more, in one embodiment, one, two, three, or four, substituents Q. As used herein, all groups that can be substituted are "optionally substituted," unless otherwise specified.

In one embodiment, each Q is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —PR$^e$R$^h$, —P(OR$^e$)R$^h$, —P(OR$^e$)(OR$^h$), —P(O)R$^e$R$^h$, —P(O)(OR$^e$)R$^h$, —P(O)(OR$^e$)(OR$^h$), —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

Compounds

In one embodiment, provided herein is a ruthenium complex of Formula I:

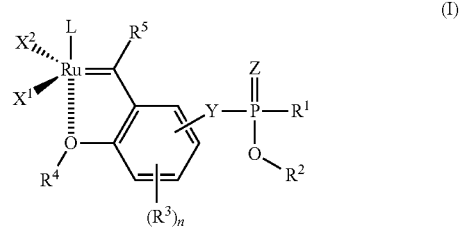

wherein:

L is a neutral ligand;

R$^1$ is $C_{1-12}$ alkyl, $C_{3-10}$ cycloalkyl, $C_{6-14}$ aryl, heteroaryl, heterocyclyl, or —NR$^{3b}$R$^{3c}$;

R$^2$ is H, $C_{1-12}$ alkyl, $C_{3-10}$ cycloalkyl, or $C_{6-14}$ aryl;

R$^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)R$^{3a}$, —C(O)OR$^{3a}$, —C(O)NR$^{3b}$R$^{3c}$, —OR$^{3a}$, —NR$^{3b}$R$^{3c}$, —NR$^{3a}$C(O)R$^{3b}$, —NR$^{3a}$C(O)OR$^{3b}$ —NR$^{3a}$S(O)$_2$R$^{3b}$, —PR$^{3a}$R$^{3b}$, —P(OR$^{3a}$)R$^{3b}$, —P(OR$^{3a}$)(OR$^{3b}$), —P(O)R$^{3a}$R$^{3b}$, —P(O)(OR$^{3a}$)R$^{3b}$, —P(O)(OR$^{3a}$)(OR$^{3b}$), —S(O)$_2$R$^{3a}$, or —SO$_2$NR$^{3b}$R$^{3c}$, R$^4$ is C$_{1-12}$ alkyl, C$_{3-10}$ cycloalkyl, C$_{7-15}$ aralkyl, or —C(R$^{4a}$R$^{4b}$)C(O)NR$^{4c}$R$^{4d}$;

R$^5$ is hydrogen, C$_{1-12}$ alkyl, C$_{2-12}$ alkenyl, C$_{2-12}$ alkynyl, C$_{3-10}$ cycloalkyl, or C$_{6-14}$ aryl;

each R$^{3a}$ and R$^{3d}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl;

each R$^{3b}$ and R$^{3c}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or R$^{3b}$ and R$^{3c}$ together with the N atom form a heteroaryl or heterocyclyl;

R$^{4a}$ and R$^{4b}$ are each independently hydrogen, C$_{1-6}$ alkyl, C$_{3-8}$ cycloalkyl, C$_{6-14}$ aryl, or C$_{7-15}$ aralkyl;

R$^{4c}$ and R$^{4d}$ are each independently hydrogen, C$_{1-6}$ alkyl, C$_{3-8}$ cycloalkyl, C$_{6-14}$ aryl, or C$_{7-15}$ aralkyl; or R$^{4c}$ and R$^{4d}$ together with the N atom form heterocyclyl;

X$^1$ and X$^2$ are each independently an anionic ligand;

Y is a bond or —NR$^b$—;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q; or (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —PR$^a$R$^d$, —P(OR$^a$)R$^d$, —P(OR$^a$)(OR$^d$), —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, or —SO$_2$NR$^b$R$^c$; wherein each R$^a$, R$^b$, R$^c$, and R$^d$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q; or R$^b$ and R$^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) —C(O)R$^e$, —C(O)OR$^e$, —C(O)NR$^f$R$^g$, —C(NR$^e$)NR$^f$R$^g$, —OC(O)R$^e$, —OC(O)R$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —PR$^e$R$^h$, —P(OR$^e$)R$^h$, —P(OR$^e$)(OR$^h$), —P(O)R$^e$R$^h$, —P(O)(OR$^e$)R$^h$, —P(O)(OR$^e$)(OR$^h$), —SR$^e$, —S(O)R$^e$, —S(O)$_2$R$^e$, or —S(O)$_2$NR$^f$R$^g$; wherein each R$^e$, R$^f$, R$^g$, and R$^h$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or R$^f$ and R$^g$ together with the N atom to which they are attached form heterocyclyl.

In another embodiment, provided herein is a ruthenium complex of Formula I:

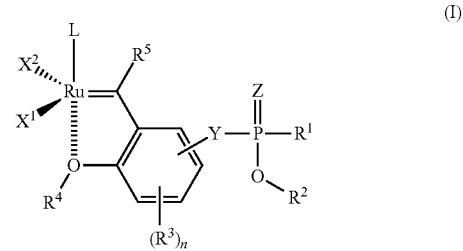

(I)

wherein:

L is a neutral ligand;

R$^1$ is C$_{1-12}$ alkyl, C$_{3-10}$ cycloalkyl, C$_{6-14}$ aryl, heteroaryl, heterocyclyl, or —NR$^{3b}$R$^{3c}$;

R$^2$ is H, C$_{1-12}$ alkyl, C$_{3-10}$ cycloalkyl, or C$_{6-14}$ aryl;

R$^3$ is halo, cyano, nitro, C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, —C(O)R$^{3a}$, —C(O)OR$^{3a}$, —C(O)NR$^{3b}$R$^{3c}$, —OR$^{3a}$, —NR$^{3b}$R$^{3c}$, —NR$^{3a}$C(O)R$^{3b}$, —NR$^{3a}$C(O)OR$^{3b}$, —NR$^{3a}$S(O)$_2$R$^{3b}$, —PR$^{3a}$R$^{3b}$, —P(OR$^{3a}$)R$^{3b}$, —P(OR$^{3a}$)(OR$^{3b}$), —P(O)R$^{3a}$R$^{3b}$, —P(O)(OR$^{3a}$)R$^{3b}$, —P(O)(OR$^{3a}$)(OR$^{3b}$), —S(O)$_2$R$^{3a}$, or —SO$_2$NR$^{3b}$R$^{3c}$, R$^4$ is C$_{1-12}$ alkyl, C$_{3-10}$ cycloalkyl, or C$_{7-15}$ aralkyl;

R$^5$ is hydrogen, C$_{1-12}$ alkyl, C$_{2-12}$ alkenyl, C$_{2-12}$ alkynyl, C$_{3-10}$ cycloalkyl, or C$_{6-14}$ aryl;

X$^1$ and X$^2$ are each independently an anionic ligand;

Y is a bond or —NR$^b$—;

Z is O or S;

n is an integer of 0, 1, 2, or 3;

each R$^{3a}$ and R$^{3d}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; and each R$^{3b}$ and R$^{3c}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or R$^{3b}$ and R$^{3c}$ together with the N atom form a heteroaryl or heterocyclyl;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q; or (c) —C(O)R$^a$, —C(O)OR$^a$, —C(O)NR$^b$R$^c$, —C(NR$^a$)NR$^b$R$^e$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —PR$^a$R$^d$, —P(OR$^a$)R$^d$, —P(OR$^a$)(OR$^d$), —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, or —SO$_2$NR$^b$R$^c$; wherein each R$^a$, R$^b$, R$^c$, and R$^d$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q; or R$^b$ and R$^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) C$_{1-6}$ alkyl, C$_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —C(O)R$^e$, —C(O)OR$^e$, —C(O)NR$^f$R$^g$, —C(NR$^e$)NR$^f$R$^g$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —PR$^e$R$^h$, —P(OR$^e$)R$^h$, —P(OR$^e$)(OR$^h$), —P(O)R$^e$R$^h$, —P(O)(OR$^e$)R$^h$, —P(O)(OR$^e$)(OR$^h$), —SR$^e$, —S(O)R$^e$, —S(O)$_2$R$^e$, or —S(O)$_2$NR$^f$R$^g$; wherein each R$^e$, R$^f$, R$^g$, and R$^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or R$^f$ and R$^g$ together with the N atom to which they are attached form heterocyclyl.

In one embodiment, provided herein is a ruthenium complex of Formula Ia:

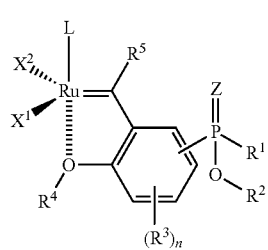

(Ia)

wherein:

L is a neutral ligand;

R$^1$ is $C_{1-12}$ alkyl, $C_{3-10}$ cycloalkyl, $C_{6-14}$ aryl, heteroaryl, heterocyclyl, or —NR$^{3b}$R$^{3c}$;

R$^2$ is H, $C_{1-12}$ alkyl, $C_{3-10}$ cycloalkyl, or $C_{6-14}$ aryl;

R$^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)R$^{3a}$, —C(O)OR$^{3a}$, —C(O)NR$^{3b}$R$^{3c}$, —OR$^{3a}$, —NR$^{3b}$R$^{3c}$, —NR$^{3a}$C(O)R$^{3b}$, —NR$^{3a}$C(O)OR$^{3b}$, —NR$^{3a}$S(O)$_2$R$^{3b}$, —PR$^{3a}$R$^{3b}$, —P(OR$^{3a}$)R$^{3b}$, —P(OR$^{3a}$)(OR$^{3b}$), —P(O)R$^{3a}$R$^{3b}$, —P(O)(OR$^{3a}$)R$^{3b}$, —P(O)(OR$^{3a}$)(OR$^{3b}$), —S(O)$_2$R$^{3a}$, or —SO$_2$NR$^{3b}$R$^{3c}$, R$^4$ is $C_{1-12}$ alkyl, $C_{3-10}$ cycloalkyl, $C_{7-15}$ aralkyl, or —C(R$^{4a}$R$^{4b}$)C(O)NR$^{4c}$R$^{4d}$;

R$^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;

each R$^{3a}$ and R$^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each R$^{3b}$ and R$^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or R$^{3b}$ and R$^{3c}$ together with the N atom form a heteroaryl or heterocyclyl;

R$^{4a}$ and R$^{4b}$ are each independently hydrogen, $C_{1-6}$ alkyl, $C_{3-8}$ cycloalkyl, $C_{6-14}$ aryl, or $C_{7-15}$ aralkyl;

R$^{4c}$ and R$^{4d}$ are each independently hydrogen, $C_{1-6}$ alkyl, $C_{3-8}$ cycloalkyl, $C_{6-14}$ aryl, or $C_{7-15}$ aralkyl; or R$^{4c}$ and R$^{4d}$ together with the N atom form heterocyclyl; X$^1$ and X$^2$ are each independently an anionic ligand;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, NR$^a$S(O)$_2$R$^d$, —NR$^a$S(O)NR$^b$R$^c$, —NR$^a$S(O)$_2$NR$^b$R$^c$, —PR$^a$R$^d$, —P(OR$^a$)R$^d$, —P(OR$^a$)(OR$^d$), —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, or —SO$_2$NR$^b$R$^c$; wherein each R$^a$, R$^b$, R$^c$, and R$^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or R$^b$ and R$^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —PR$^e$R$^h$, —P(OR$^e$)R$^h$, —P(OR$^e$)(OR$^h$), —P(O)R$^e$R$^h$, —P(O)(OR$^e$)R$^h$, —P(O)(OR$^e$)(OR$^h$), —S(O)R$^e$, —S(O)$_2$R$^e$, or —S(O)$_2$NR$^f$R$^g$; wherein each R$^e$, R$^f$, R$^g$, and R$^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or R$^f$ and R$^g$ together with the N atom to which they are attached form heterocyclyl.

In another embodiment, provided herein is a ruthenium complex of Formula Ia:

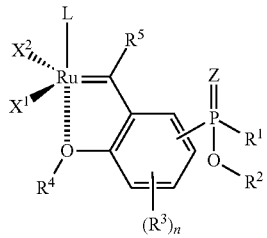

(Ia)

wherein:

L is a neutral ligand;

R$^1$ is $C_{1-12}$ alkyl, $C_{3-10}$ cycloalkyl, $C_{6-14}$ aryl, heteroaryl, heterocyclyl, or NR$^{3b}$R$^{3c}$;

R$^2$ is H, $C_{1-12}$ alkyl, $C_{3-10}$ cycloalkyl, or $C_{6-14}$ aryl;

R$^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)R$^{3a}$, —C(O)OR$^{3a}$, —C(O)NR$^{3b}$R$^{3c}$, —OR$^{3a}$, —NR$^{3b}$R$^{3c}$, —NR$^{3a}$C(O)R$^{3b}$, —NR$^{3a}$C(O)OR$^{3b}$, —NR$^{3a}$S(O)$_2$R$^{3b}$, —PR$^{3a}$R$^{3b}$, —P(OR$^{3a}$)R$^{3b}$, —P(OR$^{3a}$)(OR$^{3b}$), —P(O)R$^{3a}$R$^{3b}$, —P(O)(OR$^{3a}$)R$^{3b}$, —P(O)(OR$^{3a}$)(OR$^{3b}$), —S(O)$_2$R$^{3a}$, or —SO$_2$NR$^{3b}$R$^{3c}$, R$^4$ is $C_{1-12}$ alkyl, $C_{3-10}$ cycloalkyl, or $C_{7-15}$ aralkyl;

R$^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;

each $R^{3a}$ and $R^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each $R^{3b}$ and $R^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{3b}$ and $R^{3c}$ together with the N atom form a heteroaryl or heterocyclyl;

$X^1$ and $X^2$ are each independently an anionic ligand;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —P$R^aR^d$, —P(O$R^a$)$R^d$, —P(O$R^a$)(O$R^d$), —P(O)$R^aR^d$, —P(O)(O$R^a$)$R^d$, —P(O)(O$R^a$)(O$R^d$), —S$R^a$, —S(O)$R^a$, —S(O)$_2R^a$, or —SO$_2$N$R^bR^c$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or $R^b$ and $R^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —P(O$R^e$)$R^h$, —P(O$R^e$)(O$R^h$), —P(O)$R^eR^h$, —P(O)(O$R^e$)$R^h$, —P(O)(O$R^e$)(O$R^h$), —S$R^e$, —S(O)$R^e$, —S(O)$_2R^e$, or —S(O)$_2$N$R^fR^g$; wherein each $R^e$, $R^f$, $R^g$, and $R^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^f$ and $R^g$ together with the N atom to which they are attached form heterocyclyl.

In yet another embodiment, provided herein is a ruthenium complex of Formula Ib:

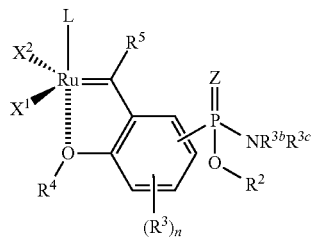

(Ib)

wherein:

L is a neutral ligand;

$R^2$ is H, $C_{1-12}$ alkyl, $C_{3-10}$ cycloalkyl, or $C_{6-14}$ aryl;

$R^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)$R^{3a}$, —C(O)O$R^{3a}$, —C(O)N$R^{3b}R^{3c}$, —O$R^{3a}$, —N$R^{3b}R^{3c}$, —N$R^{3a}$C(O)$R^{3b}$, —N$R^{3a}$C(O)O$R^{3b}$, —N$R^{3a}$S(O)$_2R^{3b}$, —P$R^{3a}R^{3b}$, —P(O$R^{3a}$)$R^{3b}$, —P(O$R^{3a}$)(O$R^{3b}$), —P(O)$R^{3a}R^{3b}$, —P(O)(O$R^{3a}$)$R^{3b}$, —P(O)(O$R^{3a}$)(O$R^{3b}$), —S(O)$_2R^{3a}$, or —SO$_2$N$R^{3b}R^{3c}$;

$R^4$ is $C_{1-12}$ alkyl, $C_{3-10}$ cycloalkyl, $C_{7-15}$ aralkyl, or —C($R^{4a}R^{4b}$)C(O)N$R^{4c}R^{4d}$;

$R^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;

each $R^{3a}$ and $R^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each $R^{3b}$ and $R^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{3b}$ and $R^{3c}$ together with the N atom form a heteroaryl or heterocyclyl;

$R^{4a}$ and $R^{4b}$ are each independently hydrogen, $C_{1-6}$ alkyl, $C_{3-8}$ cycloalkyl, $C_{6-14}$ aryl, or $C_{7-15}$ aralkyl;

$R^{4c}$ and $R^{4d}$ are each independently hydrogen, $C_{1-6}$ alkyl, $C_{3-8}$ cycloalkyl, $C_{6-14}$ aryl, or $C_{7-15}$ aralkyl; or $R^{4c}$ and $R^{4d}$ together with the N atom form heterocyclyl;

$X^1$ and $X^2$ are each independently an anionic ligand;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —P$R^aR^d$, —P(P$R^aR^d$), —P(O$R^a$)(O$R^d$), —P(O)$R^aR^d$, —P(O)(O$R^a$)$R^d$, —P(O)(O$R^a$)(O$R^d$), —S$R^a$, —S(O)$R^a$, —S(O)$_2R^a$, or —SO$_2$N$R^bR^c$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or $R^b$ and $R^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —P$R^eR^h$, —P(O$R^e$)$R^h$, —P(O$R^e$)(O$R^h$), —P(O)$R^eR^h$, —P(O)(O$R^e$)$R^h$, —P(O)(O$R^e$)(O$R^h$), —S$R^e$, —S(O)$R^e$, —S(O)$_2R^e$, or —S(O)$_2$N$R^fR^g$; wherein each $R^e$, $R^f$, $R^g$, and $R^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^f$ and $R^g$ together with the N atom to which they are attached form heterocyclyl.

In yet another embodiment, provided herein is a ruthenium complex of Formula Ib:

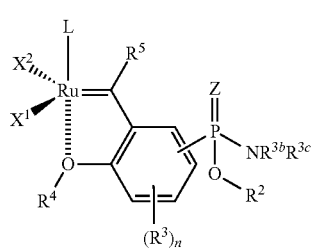

(Ib)

wherein:
L is a neutral ligand;
$R^2$ is H, $C_{1-12}$ alkyl, $C_{3-10}$ cycloalkyl, or $C_{6-14}$ aryl;
$R^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)$R^{3a}$, —C(O)O$R^{3a}$, —C(O)N$R^{3b}R^{3c}$, —O$R^{3a}$, —N$R^{3b}R^{3c}$, —N$R^{3a}$C(O)$R^{3b}$, —N$R^{3a}$C(O)O$R^{3b}$, —N$R^{3a}$S(O)$_2$$R^{3b}$, —P$R^{3a}R^{3b}$, —P(O$R^{3a}$)$R^{3b}$, —P(O$R^{3a}$)(O$R^{3b}$), —P(O)$R^{3a}R^{3b}$, —P(O)(O$R^{3a}$)$R^{3b}$, —P(O)(O$R^{3a}$)(O$R^{3b}$), —S(O)$_2$$R^{3a}$, or —SO$_2$N$R^{3b}R^{3c}$,
$R^4$ is $C_{1-12}$ alkyl, $C_{3-10}$ cycloalkyl, or $C_{7-15}$ aralkyl;
$R^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;
each $R^{3a}$ and $R^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;
each $R^{3b}$ and $R^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{3b}$ and $R^{3c}$ together with the N atom form a heteroaryl or heterocyclyl;
$X^1$ and $X^2$ are each independently an anionic ligand;
Z is O or S; and
n is an integer of 0, 1, 2, or 3;
wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2$$R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2$$R^d$, —N$R^a$S(O)N$R^bR^c$, —N$R^a$S(O)$_2$N$R^bR^c$, —P$R^aR^d$, —P(O$R^a$)$R^d$, —P(O$R^a$)(O$R^d$), —P(O)$R^aR^d$, —P(O)(O$R^a$)$R^d$, —P(O)(O$R^a$)(O$R^d$), —S$R^a$, —S(O)$R^a$, —S(O)$_2$$R^a$, or —SO$_2$N$R^bR^c$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or $R^b$ and $R^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2$$R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^b$)N$R^fR^g$, —N$R^e$S(O)$R^h$, —N$R^e$S(O)$_2$$R^h$, —N$R^e$S(O)N$R^fR^g$, —N$R^e$S(O)$_2$N$R^fR^g$, —P(O$R^e$)$R^h$, —P(O$R^e$)(O$R^h$), —P(O)$R^eR^h$, —P(O)(O$R^e$)$R^h$, —P(O)(O$R^e$)(O$R^h$), —S$R^e$, —S(O)$R^e$, —S(O)$_2$$R^e$, or —S(O)$_2$N$R^fR^g$; wherein each $R^e$, $R^f$, $R^g$, and $R^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^f$ and $R^g$ together with the N atom to which they are attached form heterocyclyl.

In yet another embodiment, the compound is a ruthenium complex of Formula Ic:

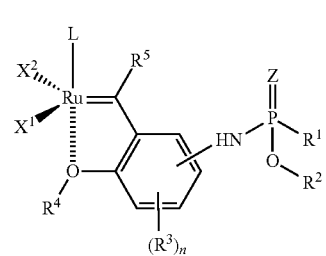

(Ic)

wherein:
L is a neutral ligand;
$R^1$ is $C_{1-12}$ alkyl, $C_{3-10}$ cycloalkyl, $C_{6-14}$ aryl, heteroaryl, heterocyclyl, or —N$R^{3b}R^{3c}$;
$R^2$ is H, $C_{1-12}$ alkyl, $C_{3-10}$ cycloalkyl, or $C_{6-14}$ aryl;
$R^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)$R^{3a}$, —C(O)O$R^{3a}$, —C(O)N$R^{3b}R^{3c}$, —O$R^{3a}$, —N$R^{3b}R^{3c}$, —N$R^{3a}$C(O)$R^{3b}$, —N$R^{3a}$C(O)O$R^{3b}$, —N$R^{3a}$S(O)$_2$$R^{3b}$, —P$R^{3a}R^{3b}$, —P(O$R^{3a}$)$R^{3b}$, —P(O$R^{3a}$)(O$R^{3b}$), —P(O)$R^{3a}R^{3b}$, —P(O)(O$R^{3a}$)$R^{3b}$, —P(O)(O$R^{3a}$)(O$R^{3b}$), —S(O)$_2$$R^{3a}$, or —SO$_2$N$R^{3b}R^{3c}$,
$R^4$ is $C_{1-12}$ alkyl, $C_{3-10}$ cycloalkyl, $C_{7-15}$ aralkyl, or —C($R^{4a}R^{4b}$)C(O)N$R^{4c}R^{4d}$;
$R^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;
each $R^{3a}$ and $R^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;
each $R^{3b}$ and $R^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{3b}$ and $R^{3c}$ together with the N atom form a heteroaryl or heterocyclyl;
$R^{4a}$ and $R^{4b}$ are each independently hydrogen, $C_{1-6}$ alkyl, $C_{3-8}$ cycloalkyl, $C_{6-14}$ aryl, or $C_{7-15}$ aralkyl;
$R^{4c}$ and $R^{4d}$ are each independently hydrogen, $C_{1-6}$ alkyl, $C_{3-8}$ cycloalkyl, $C_{6-14}$ aryl, or $C_{7-15}$ aralkyl; or $R^{4c}$ and $R^{4d}$ together with the N atom form heterocyclyl;
$X^1$ and $X^2$ are each independently an anionic ligand;
Z is O or S; and
n is an integer of 0, 1, 2, or 3;
wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —PR$^a$R$^d$, —P(OR$^a$)R$^d$, —P(OR$^a$)(OR$^d$), —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, or —SO$_2$NR$^b$R$^c$; wherein each R$^a$, R$^b$, R$^c$, and R$^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or R$^b$ and R$^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —PR$^e$R$^h$, —P(OR$^e$)R$^h$, —P(OR$^e$)(OR$^h$), —P(O)R$^e$R$^h$, —P(O)(OR$^e$)R$^h$, —P(O)(OR$^e$)(OR$^h$), —SR$^e$, —S(O)R$^e$, —S(O)$_2$R$^e$, or —S(O)$_2$NR$^f$R$^g$; wherein each R$^e$, R$^f$, R$^g$, and R$^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or R$^f$ and R$^g$ together with the N atom to which they are attached form heterocyclyl.

In yet another embodiment, the compound is a ruthenium complex of Formula Ic:

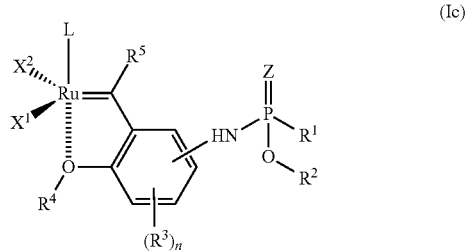

(Ic)

wherein:
L is a neutral ligand;
R$^1$ is $C_{1-12}$ alkyl, $C_{3-10}$ cycloalkyl, $C_{6-14}$ aryl, heteroaryl, heterocyclyl, or —NR$^{3b}$R$^{3c}$;
R$^2$ is H, $C_{1-12}$ alkyl, $C_{3-10}$ cycloalkyl, or $C_{6-14}$ aryl;
R$^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)R$^{3a}$, —C(O)OR$^{3a}$, —C(O)NR$^{3b}$R$^{3c}$, —OR$^{3a}$, —NR$^{3b}$R$^{3c}$, —NR$^{3a}$C(O)R$^{3b}$, —NR$^{3a}$C(O)OR$^{3b}$, —NR$^{3a}$S(O)$_2$R$^{3b}$, —PR$^{3a}$R$^{3b}$, —P(OR$^{3a}$)R$^{3b}$, —P(OR$^{3a}$)(OR$^{3b}$), —P(O)R$^{3a}$R$^{3b}$, —P(O)(OR$^{3a}$)R$^{3b}$, —P(O)(OR$^{3a}$)(OR$^{3b}$), —S(O)$_2$R$^{3a}$, or —SO$_2$NR$^{3b}$R$^{3c}$,
R$^4$ is $C_{1-12}$ alkyl, $C_{3-10}$ cycloalkyl, $C_{7-15}$ aralkyl;

R$^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;
each R$^{3a}$ and R$^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;
each R$^{3b}$ and R$^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or R$^{3b}$ and R$^{3c}$ together with the N atom form a heteroaryl or heterocyclyl;
X$^1$ and X$^2$ are each independently an anionic ligand;
Z is O or S; and
n is an integer of 0, 1, 2, or 3;
wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —PR$^a$R$^d$, —P(OR$^a$)R$^d$, —P(OR$^a$)(OR$^d$), —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, or —SO$_2$NR$^b$R$^c$; wherein each R$^a$, R$^b$, R$^c$, and R$^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or R$^b$ and R$^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —PR$^e$R$^h$, —P(OR$^e$)R$^h$, —P(OR$^e$)(OR$^h$), —P(O)R$^e$R$^h$, —P(O)(OR$^e$)R$^h$, —P(O)(OR$^e$)(OR$^h$), —SR$^e$, —S(O)R$^e$, —S(O)$_2$R$^e$, or —S(O)$_2$NR$^f$R$^g$; wherein each R$^e$, R$^f$, R$^g$, and R$^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or R$^f$ and R$^g$ together with the N atom to which they are attached form heterocyclyl.

In yet another embodiment, provided herein is a compound of Formula II:

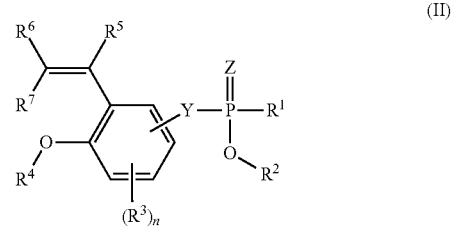

(II)

wherein:

$R^1$ is $C_{1-12}$ alkyl, $C_{3-10}$ cycloalkyl, $C_{6-14}$ aryl, heteroaryl, heterocyclyl, or —$NR^{3b}R^{3c}$;

$R^2$ is H, $C_{1-12}$ alkyl, $C_{3-10}$ cycloalkyl, or $C_{6-14}$ aryl;

$R^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)$R^{3a}$, —C(O)O$R^{3a}$, —C(O)$NR^{3b}R^{3c}$, —O$R^{3a}$, —$NR^{3b}R^{3c}$, —$NR^{3a}$C(O)$R^{3b}$, —$NR^{3a}$C(O)O$R^{3b}$, —$NR^{3a}$S(O)$_2R^{3b}$, —P$R^{3a}R^{3b}$, —P(O$R^{3a}$)$R^{3b}$, —P(O$R^{3a}$)(O$R^{3b}$), —P(O)$R^{3a}R^{3b}$, —P(O)(O$R^{3a}$)$R^{3b}$, —P(O)(O$R^{3a}$)(O$R^{3b}$), —S(O)$_2R^{3a}$, or —SO$_2NR^{3b}R^{3c}$, $R^4$ is $C_{1-12}$ alkyl, $C_{3-10}$ cycloalkyl, $C_{7-15}$ aralkyl, or —C($R^{4a}R^{4b}$)C(O)$NR^{4c}R^{4d}$;

$R^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;

$R^6$ and $R^7$ are independently hydrogen or $C_{1-6}$ alkyl;

each $R^{3a}$ and $R^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each $R^{3b}$ and $R^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{3b}$ and $R^{3c}$ together with the N atom form a heteroaryl or heterocyclyl;

$R^{4a}$ and $R^{4b}$ are each independently hydrogen, $C_{1-6}$ alkyl, $C_{3-8}$ cycloalkyl, $C_{6-14}$ aryl, or $C_{7-15}$ aralkyl;

$R^{4c}$ and $R^{4d}$ are each independently hydrogen, $C_{1-6}$ alkyl, $C_{3-8}$ cycloalkyl, $C_{6-14}$ aryl, or $C_{7-15}$ aralkyl; or $R^{4c}$ and $R^{4d}$ together with the N atom form heterocyclyl;

Y is a bond or —$NR^b$—;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —C(O)$R^a$, —C(O)O$R^a$, —C(O)$NR^bR^c$, —C($NR^a$)$NR^bR^c$, —O$R^a$, —OC(O)$R^a$, —OC(O)O$R^a$, —OC(O)$NR^bR^c$, —OC(=$NR^a$)$NR^bR^c$, —OS(O)$R^a$, —OS(O)$_2R^a$, —OS(O)$NR^bR^c$, —OS(O)$_2NR^bR^c$, —$NR^bR^c$, —$NR^a$C(O)$R^d$, —$NR^a$C(O)O$R^d$, —$NR^a$C(O)$NR^bR^c$, —$NR^a$C(=$NR^d$)$NR^bR^c$, —$NR^a$S(O)$R^d$, —$NR^a$S(O)$_2R^d$, —$NR^a$S(O)$NR^bR^c$, —$NR^a$S(O)$_2NR^bR^c$, —P$R^aR^d$, —P(O$R^a$)$R^d$, —P(O$R^a$)(O$R^d$), —P(O)$R^aR^d$, —P(O)(O$R^a$)$R^d$, —P(O)(O$R^a$)(O$R^d$), —S$R^a$, —S(O)$R^a$, —S(O)$_2R^a$, or —SO$_2NR^bR^c$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or $R^b$ and $R^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —C(O)$R^e$, —C(O)O$R^e$, —C(O)$NR^fR^g$, —C($NR^e$)$NR^fR^g$, —O$R^e$, —OC(O)$R^e$, —OC(O)O$R^e$, —OC(O)$NR^fR^g$, —OC(=$NR^e$)$NR^fR^g$, —OS(O)$R^e$, —OS(O)$_2R^e$, —OS(O)$NR^fR^g$, —OS(O)$_2NR^fR^g$, —$NR^fR^g$, —$NR^e$C(O)$R^h$, —$NR^e$C(O)O$R^h$, —$NR^e$C(O)$NR^fR^g$, —$NR^e$C(=$NR^h$)$NR^fR^g$, —$NR^e$S(O)$R^h$, —$NR^e$S(O)$_2R^h$, —$NR^e$S(O)$NR^fR^g$, —$NR^e$S(O)$_2NR^fR^g$, —P$R^eR^h$, —P(O$R^e$)$R^h$, —P(O$R^e$)(O$R^h$), —P(O)$R^eR^h$, —P(O)(O$R^e$)$R^h$, —P(O)(O$R^e$)(O$R^h$), —S$R^e$, —S(O)$R^e$, —S(O)$_2R^e$, or —S(O)$_2NR^fR^g$; wherein each $R^e$, $R^f$, $R^g$, and $R^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^f$ and $R^g$ together with the N atom to which they are attached form heterocyclyl.

In still another embodiment, provided herein is a compound of Formula II:

(II)

wherein:

$R^1$ is $C_{1-12}$ alkyl, $C_{3-10}$ cycloalkyl, $C_{6-14}$ aryl, heteroaryl, heterocyclyl, or —$NR^{3b}R^{3c}$;

$R^2$ is H, $C_{1-12}$ alkyl, $C_{3-10}$ cycloalkyl, or $C_{6-14}$ aryl;

$R^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)$R^{3a}$, —C(O)O$R^{3a}$, —C(O)$NR^{3b}R^{3c}$, —O$R^{3a}$, —$NR^{3b}R^{3c}$, —$NR^{3a}$C(O)$R^{3b}$—$NR^{3a}$C(O)O$R^{3b}$, —$NR^{3a}$S(O)$_2R^{3b}$, —P$R^{3a}R^{3b}$, —P(O$R^{3a}$)$R^{3b}$, —P(O$R^{3a}$)(O$R^{3b}$), —P(O)$R^{3a}R^{3b}$, —P(O)(O$R^{3a}$)$R^{3b}$, —P(O)(O$R^{3a}$)(O$R^{3b}$), —S(O)$_2R^{3a}$, or —SO$_2NR^{3b}R^{3c}$, $R^4$ is $C_{1-12}$ alkyl, $C_{3-10}$ cycloalkyl, or $C_{7-15}$ aralkyl;

$R^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;

$R^6$ and $R^7$ are independently hydrogen or $C_{1-6}$ alkyl;

each $R^{3a}$ and $R^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each $R^{3b}$ and $R^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{3b}$ and $R^{3c}$ together with the N atom form a heteroaryl or heterocyclyl;

Y is a bond or —$NR^b$—;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —C(O)$R^a$, —C(O)O$R^a$, —C(O)$NR^bR^c$, —C($NR^a$)$NR^bR^c$, —O$R^a$, —OC(O)$R^a$, —OC(O)O$R^a$, —OC(O)$NR^bR^c$, —OC(=$NR^a$)$NR^bR^c$, —OS(O)$R^a$, —OS(O)$_2R^a$, —OS(O)$NR^bR^c$, —OS(O)$_2NR^bR^c$, —$NR^bR^c$, —$NR^a$C(O)$R^d$, —$NR^a$C(O)O$R^d$, —$NR^a$C(O)$NR^bR^c$, —$NR^a$C(=$NR^d$)$NR^bR^c$, —$NR^a$S(O)$R^d$, —$NR^a$S(O)$_2R^d$, —$NR^a$S(O)$NR^bR^c$, —$NR^a$S(O)$_2NR^bR^c$, —P$R^aR^d$, —P(O$R^a$)$R^d$, —P(O$R^a$)(O$R^d$), —P(O)$R^aR^d$, —P(O)(O$R^a$)$R^d$, —P(O)(O$R^a$)(O$R^d$), —S$R^a$, —S(O)$R^a$, —S(O)$_2R^a$, or —SO$_2NR^bR^c$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or $R^b$ and $R^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —PR$^e$R$^h$, —P(OR$^e$)R$^h$, —P(OR$^e$)(OR$^h$), —P(O)R$^e$R$^h$, —P(O)(OR$^e$)R$^h$, —P(O)(OR$^e$)(OR$^h$), —SR$^e$, —S(O)R$^e$, —S(O)$_2$R$^e$, or —S(O)$_2$NR$^f$R$^g$; wherein each R$^e$, R$^f$, R$^g$, and R$^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or R$^f$ and R$^g$ together with the N atom to which they are attached form heterocyclyl.

In one embodiment, provided herein is a compound of Formula IIa:

(IIa)

wherein:

R$^1$ is $C_{1-12}$ alkyl, $C_{3-10}$ cycloalkyl, $C_{6-14}$ aryl, heteroaryl, heterocyclyl, or —NR$^{3b}$R$^{3c}$;

R$^2$ is H, $C_{1-12}$ alkyl, $C_{3-10}$ cycloalkyl, or $C_{6-14}$ aryl;

R$^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)R$^{3a}$, —C(O)OR$^{3a}$, —C(O)NR$^{3b}$R$^{3c}$, —OR$^{3a}$, —NR$^{3b}$R$^{3c}$, —NR$^{3a}$C(O)R$^{3b}$, —NR$^{3a}$C(O)OR$^{3b}$, —NR$^{3a}$S(O)$_2$R$^{3b}$, —PR$^{3a}$R$^{3b}$, P(OR$^{3a}$)R$^{3b}$, —P(OR$^{3a}$)(OR$^{3b}$), —P(O)R$^{3a}$R$^{3b}$, —P(O)(OR$^{3a}$)R$^{3b}$, —P(O)(OR$^{3a}$)(OR$^{3b}$), —S(O)$_2$R$^{3a}$, or —SO$_2$NR$^{3b}$R$^{3c}$, R$^4$ is $C_{1-12}$ alkyl, $C_{3-10}$ cycloalkyl, $C_{7-15}$ aralkyl, or —C(R$^{4a}$R$^{4b}$)C(O)NR$^{4c}$R$^{4d}$;

R$^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;

R$^6$ and R$^7$ are independently hydrogen or $C_{1-6}$ alkyl;

each R$^{3a}$ and R$^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each R$^{3b}$ and R$^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or R$^{3b}$ and R$^{3c}$ together with the N atom form a heteroaryl or heterocyclyl;

R$^{4a}$ and R$^{4b}$ are each independently hydrogen, $C_{1-6}$ alkyl, $C_{3-8}$ cycloalkyl, $C_{6-14}$ aryl, or $C_{7-15}$ aralkyl;

R$^{4c}$ and R$^{4d}$ are each independently hydrogen, $C_{1-6}$ alkyl, $C_{3-8}$ cycloalkyl, $C_{6-14}$ aryl, or $C_{7-15}$ aralkyl; or R$^{4c}$ and R$^{4d}$ together with the N atom form heterocyclyl;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —PR$^a$R$^d$, —P(OR$^a$)R$^d$, —P(OR$^a$)(OR$^d$), —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, or —SO$_2$NR$^b$R$^c$; wherein each R$^a$, R$^b$, R$^c$, and R$^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or R$^b$ and R$^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —PR$^e$R$^h$, —P(OR$^e$)R$^h$, —P(OR$^e$)(OR$^h$), —P(O)R$^e$R$^h$, —P(O)(OR$^e$)R$^h$, —P(O)(OR$^e$)(OR$^h$), —SR$^e$, —S(O)R$^e$, —S(O)$_2$R$^e$, or —S(O)$_2$NR$^f$R$^h$; wherein each R$^e$, R$^f$, R$^g$, and R$^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or R$^f$ and R$^g$ together with the N atom to which they are attached form heterocyclyl.

In another embodiment, provided herein is a compound of Formula IIa:

(IIa)

wherein:

R$^1$ is $C_{1-12}$ alkyl, $C_{3-10}$ cycloalkyl, $C_{6-14}$ aryl, heteroaryl, heterocyclyl, or —NR$^{3b}$R$^{3c}$;

R$^2$ is H, $C_{1-12}$ alkyl, $C_{3-10}$ cycloalkyl, or $C_{6-14}$ aryl;

R$^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)R$^{3a}$, —C(O)OR$^{3a}$, —C(O)NR$^{3b}$R$^{3c}$, —OR$^{3a}$, —NR$^{3b}$R$^{3c}$, —NR$^{3a}$C(O)R$^{3b}$, —NR$^{3a}$C(O)OR$^{3b}$, —NR$^{3a}$S(O)$_2$R$^{3b}$, —PR$^{3a}$R$^{3b}$, —P(OR$^{3a}$)R$^{3b}$, —P(OR$^{3a}$)(OR$^{3b}$), —P(O)R$^{3a}$R$^{3b}$, —P(O)(OR$^{3a}$)R$^{3b}$, —P(O)(OR$^{3a}$)(OR$^{3b}$), —S(O)$_2$R$^{3a}$, or —SO$_2$NR$^{3b}$R$^{3c}$, R$^4$ is $C_{1-12}$ alkyl, $C_{3-10}$ cycloalkyl, or $C_{7-15}$ aralkyl;

R$^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;

R$^6$ and R$^7$ are independently hydrogen or $C_{1-6}$ alkyl;

each $R^{3a}$ and $R^{ad}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each $R^{3b}$ and $R^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{3b}$ and $R^{3c}$ together with the N atom form a heteroaryl or heterocyclyl;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —C(O)$R^a$, —C(O)O$R^a$, —C(O)N$R^b R^c$, —C(N$R^a$)N$R^b R^c$, —O$R^a$, —OC(O)$R^a$, —OC(O)O$R^a$, —OC(O)N$R^b R^c$, —OC(=N$R^a$)N$R^b R^c$, —OS(O)$R^a$, —OS(O)$_2 R^a$, —OS(O)N$R^b R^c$, —OS(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(=N$R^d$)N$R^b R^c$, —N$R^a$S(O)$R^d$, —N$R^a$S(O)$_2 R^d$, —N$R^a$S(O)N$R^b R^c$, —N$R^a$S(O)$_2$N$R^b R^c$, —P$R^a R^d$, —P(O$R^a$)$R^d$, —P(O$R^a$)(O$R^d$), —P(O)$R^a R^d$, —P(O)(O$R^a$)$R^d$, —P(O)(O$R^a$)(O$R^d$), —S$R^a$, —S(O)$R^a$, —S(O)$_2 R^a$, or —SO$_2$N$R^b R^c$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or $R^b$ and $R^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —C(O)$R^e$, —C(O)O$R^e$, —C(O)N$R^f R^g$, —C(N$R^e$)N$R^f R^g$, —O$R^e$, —OC(O)$R^e$, —OC(O)O$R^e$, —OC(O)N$R^f R^g$, —OC(=N$R^e$)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^h$, —N$R^e$C(O)O$R^h$, —N$R^e$C(O)N$R^f R^g$, —N$R^e$C(=N$R^h$)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —P$R^e R^h$, —P(O$R^e$)$R^h$, —P(O$R^e$)(O$R^h$), —P(O)$R^e R^h$, —P(O)(O$R^e$)$R^h$, —P(O)(O$R^e$)(O$R^h$), —S$R^e$, —S(O)$R^e$, —S(O)$_2 R^e$, or —S(O)$_2$N$R^f R^g$; wherein each $R^e$, $R^f$, $R^g$, and $R^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^f$ and $R^g$ together with the N atom to which they are attached form heterocyclyl.

In yet another embodiment, provided herein is a compound of Formula IIb:

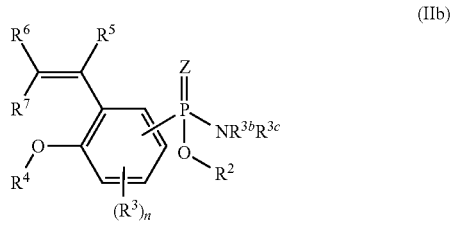

(IIb)

wherein:

$R^2$ is H, $C_{1-12}$ alkyl, $C_{3-10}$ cycloalkyl, or $C_{6-14}$ aryl;

$R^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)$R^{3a}$, —C(O)O$R^{3a}$, —C(O)N$R^{3b}R^{3c}$, —O$R^{3a}$, —N$R^{3b}R^{3c}$, —N$R^{3a}$C(O)$R^{3b}$, —N$R^{3a}$C(O)O$R^{3b}$, —N$R^{3a}$S(O)$_2 R^{3b}$, —P$R^{3a}R^{3b}$, —P(O$R^{3a}$)$R^{3b}$, —P(O$R^{3a}$)(O$R^{3b}$), —P(O)$R^{3a}R^{3b}$, —P(O)(O$R^{3a}$)$R^{3b}$, —P(O)(O$R^{3a}$)(O$R^{3b}$), —S(O)$_2 R^{3a}$, or —SO$_2$N$R^{3b}R^{3c}$;

$R^4$ is $C_{1-12}$ alkyl, $C_{3-10}$ cycloalkyl, $C_{7-15}$ aralkyl, or —C($R^{4a}R^{4b}$)C(O)N$R^{4c}R^{4d}$;

$R^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;

$R^6$ and $R^7$ are independently hydrogen or $C_{1-6}$ alkyl;

each $R^{3a}$ and $R^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each $R^{3b}$ and $R^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{3b}$ and $R^{3c}$ together with the N atom form a heteroaryl or heterocyclyl; $R^{4a}$ and $R^{4b}$ are each independently hydrogen, $C_{1-6}$ alkyl, $C_{3-8}$ cycloalkyl, $C_{6-14}$ aryl, or $C_{7-15}$ aralkyl;

$R^{4c}$ and $R^{4d}$ are each independently hydrogen, $C_{1-6}$ alkyl, $C_{3-8}$ cycloalkyl, $C_{6-14}$ aryl, or $C_{7-15}$ aralkyl; or $R^{4c}$ and $R^{4d}$ together with the N atom form heterocyclyl;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —C(O)$R^a$, —C(O)O$R^a$, —C(O)N$R^b R^c$, —C(N$R^a$)N$R^b R^c$, —O$R^a$, —OC(O)$R^a$, —OC(O)O$R^a$, —OC(O)N$R^b R^c$, —OC(=N$R^a$)N$R^b R^c$, —OS(O)$R^a$, —OS(O)$_2 R^a$, —OS(O)N$R^b R^c$, —OS(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(=N$R^d$)N$R^b R^c$, —N$R^a$S(O)$R^d$, —N$R^a$S(O)$_2 R^d$, —N$R^a$S(O)N$R^b R^c$, —N$R^a$S(O)$_2$N$R^b R^c$, —P$R^a R^d$, —P(O$R^a$)$R^d$, —P(O$R^a$)(O$R^d$), —P(O)$R^a R^d$, —P(O)(O$R^a$)$R^d$, —P(O)(O$R^a$)(O$R^d$), —S$R^a$, —S(O)$R^a$, —S(O)$_2 R^a$, or —SO$_2$N$R^b R^c$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or $R^b$ and $R^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —C(O)$R^e$, —C(O)O$R^e$, —C(O)N$R^f R^g$, —C(N$R^e$)N$R^f R^g$, —O$R^e$, —OC(O)$R^e$, —OC(O)O$R^e$, —OC(O)N$R^f R^g$, —OC(=N$R^e$)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^h$, —N$R^e$C(O)O$R^h$, —N$R^e$C(O)N$R^f R^g$, —N$R^e$C(=N$R^h$)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —P$R^e R^h$, —P(O$R^e$)$R^h$, —P(O$R^e$)(O$R^h$), —P(O)$R^e R^h$, —P(O)(O$R^e$)$R^h$, —P(O)(O$R^e$)(O$R^h$), S$R^e$, —S(O)$R^e$, —S(O)$_2 R^e$, or —S(O)$_2$N$R^f R^g$; wherein each $R^e$, $R^f$, $R^g$, and $R^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^f$ and $R^g$ together with the N atom to which they are attached form heterocyclyl.

In yet another embodiment, provided herein is a compound of Formula IIb:

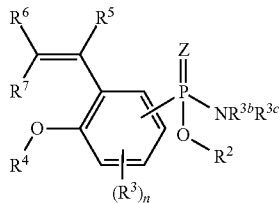

(IIb)

wherein:

$R^2$ is H, $C_{1-12}$ alkyl, $C_{3-10}$ cycloalkyl, or $C_{6-14}$ aryl;

$R^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)$R^{3a}$, —C(O)O$R^{3a}$, —C(O)N$R^{3b}R^{3c}$, —O$R^{3a}$, —N$R^{3b}R^{3c}$, —N$R^{3a}$C(O)$R^{3b}$, —N$R^{3a}$C(O)O$R^{3b}$, —N$R^{3a}$S(O)$_2R^{3b}$, —P$R^{3a}R^{3b}$, —P(O$R^{3a}$)$R^{3b}$, —P(O$R^{3a}$)(O$R^{3b}$), —P(O)$R^{3a}R^{3b}$, —P(O)(O$R^{3a}$)$R^{3b}$, —P(O)(O$R^{3a}$)(O$R^{3b}$), —S(O)$_2R^{3a}$, or —SO$_2$N$R^{3b}R^{3c}$, $R^4$ is $C_{1-12}$ alkyl, $C_{3-10}$ cycloalkyl, or $C_{7-15}$ aralkyl;

$R^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;

$R^6$ and $R^7$ are independently hydrogen or $C_{1-6}$ alkyl;

each $R^{3a}$ and $R^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each $R^{3b}$ and $R^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{3b}$ and $R^{3c}$ together with the N atom form a heteroaryl or heterocyclyl;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —P$R^aR^d$, —P(O$R^a$)$R^d$, —P(O$R^a$)(O$R^d$), —P(O)$R^aR^d$, —P(O)(O$R^a$)$R^d$, —P(O)(O$R^a$)(O$R^d$), —S$R^a$, —S(O)$R^a$, —S(O)$_2R^a$, or —SO$_2$N$R^bR^c$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or $R^b$ and $R^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —P$R^eR^h$, —P(O$R^e$)$R^h$, —P(O$R^e$)(O$R^h$), —P(O)$R^eR^h$, —P(O)(O$R^e$)$R^h$, —P(O)(O$R^e$)(O$R^h$), —S$R^e$, —S(O)$R^e$, —S(O)$_2R^e$, or —S(O)$_2$N$R^fR^g$; wherein each $R^e$, $R^f$, $R^g$, and $R^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^f$ and $R^g$ together with the N atom to which they are attached form heterocyclyl.

In yet another embodiment, provided herein is a compound of Formula IIc:

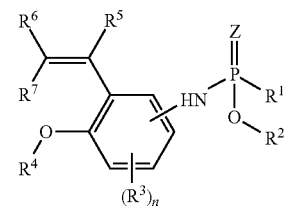

(IIc)

wherein:

$R^1$ is $C_{1-12}$ alkyl, $C_{3-10}$ cycloalkyl, $C_{6-14}$ aryl, heteroaryl, heterocyclyl, or —N$R^{3b}R^{3c}$;

$R^2$ is H, $C_{1-12}$ alkyl, $C_{3-10}$ cycloalkyl, or $C_{6-14}$ aryl;

$R^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)$R^{3a}$, —C(O)O$R^{3a}$, —C(O)N$R^{3b}R^{3c}$, —O$R^{3a}$, —N$R^{3b}R^{3c}$, —N$R^{3a}$C(O)$R^{3b}$, —N$R^{3a}$C(O)O$R^{3b}$, —N$R^{3a}$S(O)$_2R^{3b}$, —P$R^{3a}R^{3b}$, —P(O$R^{3a}$)$R^{3b}$, —P(O$R^{3a}$)(O$R^{3b}$), —P(O)$R^{3a}R^{3b}$, —P(O)(O$R^{3a}$)$R^{3b}$, —P(O)(O$R^{3a}$)(O$R^{3b}$), —S(O)$_2R^{3a}$, or —SO$_2$N$R^{3b}R^{3c}$, $R^4$ is $C_{1-12}$ alkyl, $C_{3-10}$ cycloalkyl, $C_{7-15}$ aralkyl, or —C($R^{4a}R^{4b}$)C(O)N$R^{4c}R^{4d}$;

$R^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;

$R^6$ and $R^7$ are independently hydrogen or $C_{1-6}$ alkyl;

each $R^{3a}$ and $R^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each $R^{3b}$ and $R^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{3b}$ and $R^{3c}$ together with the N atom form a heteroaryl or heterocyclyl;

$R^{4a}$ and $R^{4b}$ are each independently hydrogen, $C_{1-6}$ alkyl, $C_{3-8}$ cycloalkyl, $C_{6-14}$ aryl, or $C_{7-15}$ aralkyl;

$R^{4c}$ and $R^{4d}$ are each independently hydrogen, $C_{1-6}$ alkyl, $C_{3-8}$ cycloalkyl, $C_{6-14}$ aryl, or $C_{7-15}$ aralkyl; or $R^{4c}$ and $R^{4d}$ together with the N atom form heterocyclyl;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, aryl, $C_{7-15}$ aralkyl, heteroaryl, or heterocyclyl, each optionally substituted with one or more, in one embodiment, one, two, three, or four, substituents Q; or (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —NR$^a$S(O)$_2$NR$^b$R$^c$, —PR$^a$R$^d$, —P(OR$^a$)R$^d$, —P(OR$^a$)(OR$^d$), —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, or —SO$_2$NR$^b$R$^c$; wherein each R$^a$, R$^b$, R$^c$, and R$^d$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q; or R$^b$ and R$^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —PR$^e$R$^h$, —P(OR$^e$)R$^h$, —P(OR$^e$)(OR$^h$), —P(O)R$^e$R$^h$, —P(O)(OR$^e$)R$^h$, —P(O)(OR$^e$)(OR$^h$), —SR$^e$, —S(O)R$^e$, —S(O)$_2$R$^e$, or —S(O)$_2$NR$^f$R$^g$; wherein each R$^e$, R$^f$, R$^g$, and R$^h$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or R$^f$ and R$^g$ together with the N atom to which they are attached form heterocyclyl.

In yet another embodiment, provided herein is a compound of Formula IIc;

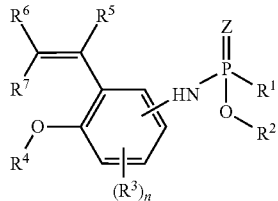

(IIc)

wherein:

R$^1$ is C$_{1-12}$ alkyl, C$_{3-10}$ cycloalkyl, C$_{6-14}$ aryl, heteroaryl, heterocyclyl, or —NR$^{3b}$R$^{3c}$;

R$^2$ is H, C$_{1-12}$ alkyl, C$_{3-10}$ cycloalkyl, or C$_{6-14}$ aryl;

R$^3$ is halo, cyano, nitro, C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, —C(O)R$^{3a}$, —C(O)OR$^{3a}$, —C(O)NR$^{3b}$R$^{3c}$, —OR$^{3a}$, —NR$^{3b}$R$^{3c}$, —NR$^{3a}$C(O)R$^{3b}$, —NR$^{3a}$C(O)OR$^{3b}$, —NR$^{3a}$S(O)$_2$R$^{3b}$, —PR$^{3a}$R$^{3b}$, —P(OR$^{3a}$)R$^{3b}$, —P(OR$^{3a}$)(OR$^{3b}$), —P(O)R$^{3a}$R$^{3b}$, —P(O)(OR$^{3a}$)R$^{3b}$, —P(O)(OR$^{3a}$)(OR$^{3b}$), —S(O)$_2$R$^{3a}$, or —SO$_2$NR$^{3b}$R$^{3c}$, R$^4$ is C$_{1-12}$ alkyl, C$_{3-10}$ cycloalkyl, or C$_{7-15}$ aralkyl;

R$^5$ is hydrogen, C$_{1-12}$ alkyl, C$_{2-12}$ alkenyl, C$_{2-12}$ alkynyl, C$_{3-10}$ cycloalkyl, or C$_{6-14}$ aryl;

R$^6$ and R$^7$ are independently hydrogen or C$_{1-6}$ alkyl;

each R$^{3a}$ and R$^{3d}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl;

each R$^{3b}$ and R$^{3c}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or R$^{3b}$ and R$^{3c}$ together with the N atom form a heteroaryl or heterocyclyl;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) C$_{1-6}$ alkyl, C$_{2-6}$ alkenyl, C$_{2-6}$ alkynyl, C$_{3-4}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q; or (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —PR$^a$R$^d$, —P(OR$^a$)R$^d$, —P(OR$_a$)(OR$^d$), —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, or —SO$_2$NR$^b$R$^c$; wherein each R$^a$, R$^b$, R$^c$, and R$^d$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q; or R$^b$ and R$^c$ together with the N atom to which they are attached form heterocyclyl, optionally substituted with one or more, in one embodiment, one, two, three, or four, substituents Q;

wherein each Q is independently selected from the group consisting of (i) cyano, halo, or nitro; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —PR$^e$R$^h$, —P(OR$^e$)R$^h$, P(OR$^e$)(OR$^h$), —P(O)R$^e$R$^h$, —P(O)(OR$^e$)R$^h$, —P(O)(OR$^e$)(OR$^h$), —SR$^e$, —S(O)R$^e$, —S(O)$_2$R$^e$, or —S(O)$_2$NR$^f$R$^g$; wherein each R$^e$, R$^f$, R$^g$, and R$^h$ is independently hydrogen; C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or R$^f$ and R$^g$ together with the N atom to which they are attached form heterocyclyl.

The groups in Formulae I, Ia, Ib, Ic, II, IIa, IIb, and IIc, including R$^1$, R$^2$, R$^3$, R$^4$, R$^5$, R$^6$, R$^7$, R$^{4a}$, R$^{4b}$, R$^{4c}$, R$^{4d}$, L, X$^1$, X$^2$, Z, Y, and n, are further defined in the following embodiments, independently or in combination. All combinations of such embodiments are within the scope of this disclosure.

In certain embodiments, R$^1$ is C$_{1-12}$ alkyl, optionally substituted with one or more substituents as described herein. In certain embodiments, R$^1$ is C$_{1-5}$ alkyl, optionally substituted with one or more substituents as described herein. In certain embodiments, R$^1$ is C$_{1-5}$ alkyl, optionally substituted with one or more halo. In certain embodiments, R$^1$ is trifluoromethyl. In certain embodiments, R$^1$ is C$_{3-10}$ cycloalkyl, optionally substituted with one or more substituents as described herein. In certain embodiments, R$^1$ is C$_{5-6}$ cycloalkyl, optionally substituted with one or more substituents as described herein.

In certain embodiments, R$^1$ is C$_{6-14}$ aryl, optionally substituted with one or more substituents as described herein. In certain embodiments, R$^1$ is C$_{6-14}$ aryl, substituted with one or more substituents, each independently selected from the group consisting of cyano, halo, nitro, trifluoromethyl, methoxy, trifluoromethylsulfonyl, trifluoroacetyl, and trifluoroacetamido. In certain embodiments, R$^1$ is phenyl. In certain embodiments, R$^1$ is phenyl, substituted with one or more substituents as described herein. In certain embodiments, R$^1$ is phenyl, substituted with one or more substituents, each independently selected from the group consisting of cyano, halo, nitro, trifluoromethyl, methoxy, trifluoromethyl-sulfonyl, trifluoroacetyl, and trifluoroacetamido. In certain embodiments, $R^1$ is phenyl, cyanophenyl (e.g., 2-, 3-, or 4-cyanophenyl), fluorophenyl (e.g., 2-, 3-, or 4-fluorophenyl), difluorophenyl (e.g., 2,4- or 3,5-difluorophenyl), trifluoromethylphenyl (e.g., 2-, 3-, or 4-trifluoromethylphenyl), bis(trifluoromethyl)phenyl (e.g., 3,5-bis(trifluoromethyl)-phenyl), methoxy-phenyl (e.g., 2-, 3-, or 4-methoxyphenyl), trifluoromethylsulfonylphenyl (e.g., 2-, 3-, or 4-trifluoromethylsulfonylphenyl), trifluoroacetylphenyl (e.g., 2-, 3-, or 4-trifluoroacetylphenyl), nitrophenyl (e.g., 2-, 3-, or 4-nitrophenyl), dinitrophenyl (e.g., 3,5-dinitrophenyl), trifluoroacetamidophenyl (e.g., 2-, 3-, 4-trifluoroacetamidophenyl), or pentofluorophenyl. In certain embodiments, $R^1$ is phenyl, 4-cyanophenyl, 4-fluorophenyl, 3,5-difluorophenyl, 4-trifluoromethylphenyl, 3,5-bis(trifluoromethyl)phenyl, 4-methoxy-phenyl, 4-trifluoromethylsulfonylphenyl, 4-trifluoroacetylphenyl, 4-nitrophenyl, 3,5-dinitrophenyl, 4-trifluoroacetamidophenyl, or pentofluorophenyl.

In certain embodiments, $R^1$ is heteroaryl, optionally substituted with one or more substituents as described herein. In certain embodiments, $R^1$ is pyridyl, thiazolyl, or pyrazolyl, each optionally substituted with one or more substituents as described herein. In certain embodiments, $R^1$ is pyridyl, thiazolyl, or pyrazolyl, each optionally substituted with one or more substituents, each independently selected from the group consisting of cyano, halo, nitro, trifluoromethyl, methoxy, trifluoromethyl-sulfonyl, trifluoroacetyl, and trifluoroacetamido. In certain embodiments, $R^1$ is pyridyl, trifluoromethyl-thiazolyl (e.g., 2-, 4-, or 5-trifluoro-methylthiazolyl), or trifluoromethyl-pyrazolyl (e.g., 3- or 4-trifluoromethylpyrazolyl). In certain embodiments, $R^1$ is pyridyl, 4-trifluoromethylthiazolyl, or 3-trifluoromethyl-pyrazolyl.

In certain embodiments $R^1$ is —$NR^{3b}R^{3c}$; wherein $R^{3b}$ and $R^{3c}$ are each as defined herein. In certain embodiments, $R^{3b}$ is hydrogen or $C_{1-6}$ alkyl, optionally substituted with one or more substituents as described herein. In certain embodiments, $R^{3b}$ is hydrogen, methyl, ethyl, or propyl. In certain embodiments, $R^{3c}$ is hydrogen or $C_{1-6}$ alkyl, optionally substituted with one or more substituents as described herein. In certain embodiments, $R^{3c}$ is hydrogen, methyl, ethyl, or propyl. In certain embodiments $R^1$ is $C_{1-6}$ alkylamino, optionally substituted with one or more substituents as described herein. In certain embodiments $R^1$ is di($C_{1-6}$ alkyl)amino, each alkyl optionally substituted with one or more substituents as described herein. In certain embodiments $R^1$ is dimethylamino.

In certain embodiments, $R^2$ is $C_{1-5}$ alkyl, optionally substituted with one or more substituents as described herein. In certain embodiments, $R^2$ is ethyl. In certain embodiments, $R^2$ is $C_{5-6}$ cycloalkyl, optionally substituted with one or more substituents as described herein.

In certain embodiments, $R^3$ is halo. In certain embodiments, $R^3$ is chloro or fluoro. In certain embodiments, $R^3$ is nitro. In certain embodiments, $R^3$ is $C_{1-12}$ alkyl, optionally substituted with one or more substituents as described herein. In certain embodiments, $R^3$ is $C_{3-10}$ cycloalkyl, optionally substituted with one or more substituents as described herein. In certain embodiments, $R^3$ is $C_{6-14}$ aryl, optionally substituted with one or more substituents as described herein. In certain embodiments, $R^3$ is —$OR^{3a}$, wherein $R^{3a}$ is as defined herein. In certain embodiments, $R^3$ is —$SO_2NR^{3a}R^{3b}$, wherein $R^{3a}$ and $R^{3b}$ are each as defined herein. In certain embodiments, $R^3$ is —$P(O)(OR^2)(R^1)$, wherein $R^1$ and $R^2$ are each as defined herein. In certain embodiments, $R^3$ is —$CO_2R^{3a}$, wherein $R^{3a}$ is as defined herein. In certain embodiments, $R^3$ is —$NR^{3a}SO_2R^{3b}$, wherein $R^{3a}$ and $R^{3b}$ are each as defined herein. In certain embodiments, each $R^{3a}$ is independently $C_{1-12}$ alkyl, optionally substituted with one or more substituents as described herein. In certain embodiments, each $R^{3a}$ is $C_{3-10}$ cycloalkyl, optionally substituted with one or more substituents as described herein. In certain embodiments, each $R^{3b}$ is independently $C_{1-12}$ alkyl, optionally substituted with one or more substituents as described herein. In certain embodiments, each $R^{3b}$ is $C_{3-10}$ cycloalkyl, optionally substituted with one or more substituents as described herein.

In certain embodiments, $R^4$ is $C_{1-5}$ alkyl, optionally substituted with one or more substituents as described herein. In certain embodiments, $R^4$ is $C_{5-6}$ cycloalkyl, optionally substituted with one or more substituents as described herein. In certain embodiments, $R^4$ is propyl (e.g., n-propyl or isopropyl). In certain embodiments, $R^4$ is isopropyl. In certain embodiments, $R^4$ is $C_{7-15}$ aralkyl, optionally substituted with one or more substituents as described herein. In certain embodiments, $R^4$ is —$C(R^{4a}R^{4b})C(O)NR^{4c}R^{4d}$, wherein $R^{4a}$, $R^{4b}$, $R^{4c}$, and $R^{4d}$ are each as defined herein.

In certain embodiments, $R^5$ is hydrogen. In certain embodiments, $R^5$ is $C_{1-5}$ alkyl, optionally substituted with one or more substituents as described herein. In certain embodiments, $R^5$ is $C_{5-6}$ cycloalkyl, optionally substituted with one or more substituents as described herein.

In certain embodiments, $R^6$ is hydrogen. In certain embodiments, $R^7$ is hydrogen. In certain embodiments, $R^6$ and $R^7$ are hydrogen.

In certain embodiments, $R^{4a}$ is hydrogen. In certain embodiments, $R^{4a}$ is $C_{1-6}$ alkyl, optionally substituted with one or more substituents as described herein. In certain embodiments, $R^{4a}$ is $C_{3-8}$ cycloalkyl, optionally substituted with one or more substituents as described herein. In certain embodiments, $R^{4a}$ is $C_{6-14}$ aryl, optionally substituted with one or more substituents as described herein. In certain embodiments, $R^{4a}$ is $C_{7-15}$ aralkyl, optionally substituted with one or more substituents as described herein.

In certain embodiments, $R^{4b}$ is hydrogen. In certain embodiments, $R^{4b}$ is $C_{1-6}$ alkyl, optionally substituted with one or more substituents as described herein. In certain embodiments, $R^{4b}$ is $C_{3-8}$ cycloalkyl, optionally substituted with one or more substituents as described herein. In certain embodiments, $R^{4b}$ is $C_{6-14}$ aryl, optionally substituted with one or more substituents as described herein. In certain embodiments, $R^{4b}$ is $C_{7-15}$ aralkyl, optionally substituted with one or more substituents as described herein.

In certain embodiments, $R^{4c}$ is hydrogen. In certain embodiments, $R^{4c}$ is $C_{1-6}$ alkyl, optionally substituted with one or more substituents as described herein. In certain embodiments, $R^{4c}$ is $C_{3-8}$ cycloalkyl, optionally substituted with one or more substituents as described herein. In certain embodiments, $R^{4c}$ is $C_{6-14}$ aryl, optionally substituted with one or more substituents as described herein. In certain embodiments, $R^{4c}$ is $C_{7-15}$ aralkyl, optionally substituted with one or more substituents as described herein.

In certain embodiments, $R^{4d}$ is hydrogen. In certain embodiments, $R^{4d}$ is $C_{1-6}$ alkyl, optionally substituted with one or more substituents as described herein. In certain embodiments, $R^{4d}$ is $C_{3-8}$ cycloalkyl, optionally substituted with one or more substituents as described herein. In certain embodiments, $R^{4d}$ is $C_{6-14}$ aryl, optionally substituted with one or more substituents as described herein. In certain embodiments, $R^{4d}$ is $C_{7-15}$ aralkyl, optionally substituted with one or more substituents as described herein.

In certain embodiments, $R^{4c}$ and $R^{4d}$ together with the N atom form heterocyclyl, optionally substituted with one or more substituents as described herein. In certain embodiments, $R^{4c}$ and $R^{4d}$ together with the N atom form 5- to 8-membered heterocyclyl, optionally substituted with one or more substituents as described herein. In certain embodiments, $R^{4c}$ and $R^{4d}$ together with the N atom form 5- to 8-membered heterocyclyl, which may contains one or more heteroatoms, each independently selected from nitrogen, oxygen, and sulfur, wherein the heterocyclyl is optionally substituted with one or more substituents as described herein.

In certain embodiments, L is a heterocyclic carbene, optionally substituted with one or more substituents as described herein. In certain embodiments, L is selected from the group consisting of:

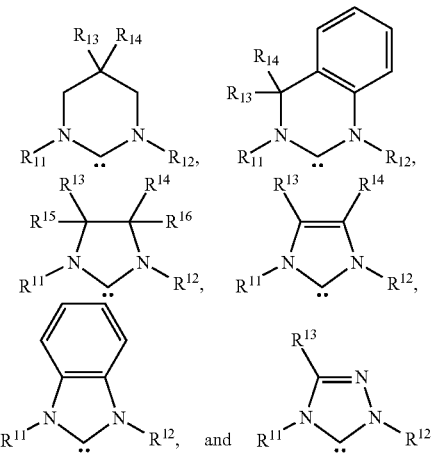

wherein:

each $R^{11}$ and $R^{12}$ is independently $C_{1-6}$ alkyl or $C_{6-14}$ aryl; and each $R^{13}$, $R^{14}$, $R^{15}$, and $R^{16}$ is independently hydrogen, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

wherein each alkyl, alkenyl, alkynyl, aryl, cycloalkyl, heterocyclyl, and heteroaryl is optionally substituted with one or more substituents.

In certain embodiments, $R^{11}$ is $C_{1-6}$ alkyl, optionally substituted with one or more substituents. In certain embodiments, $R^{11}$ is $C_{1-6}$ aryl, optionally substituted with one or more substituents. In certain embodiments, $R^{11}$ is $C_{6-14}$ aryl, substituted with one or more $C_{1-6}$ alkyl. In certain embodiments, $R^{11}$ is methylphenyl, trimethylphenyl, or di(isopropyl)phenyl. In certain embodiments, $R^{11}$ is 2-methylphenyl, 2,4,6-trimethylphenyl, or 2,6-di(isopropyl)phenyl.

In certain embodiments, $R^{12}$ is $C_{1-6}$ alkyl, optionally substituted with one or more substituents. In certain embodiments, $R^{12}$ is $C_{1-6}$ aryl, optionally substituted with one or more substituents. In certain embodiments, $R^{12}$ is $C_{6-14}$ aryl, substituted with one or more $C_{1-6}$ alkyl. In certain embodiments, $R^{12}$ is methylphenyl, trimethylphenyl, or di(isopropyl)phenyl. In certain embodiments, $R^{12}$ is 2-methylphenyl, 2,4,6-trimethylphenyl, or 2,6-di(isopropyl)phenyl.

In certain embodiments, $R^{11}$ and $R^{12}$ are trimethylphenyl. In certain embodiments, $R^{11}$ and $R^{12}$ are 2,4,6-trimethylphenyl. In certain embodiments, $R^{11}$ and $R^{12}$ are di(isopropyl)phenyl. In certain embodiments, $R^{11}$ and $R^{12}$ are 2,6-di(isopropyl)phenyl. In certain embodiments, $R^{11}$ and $R^{12}$ are methylphenyl. In certain embodiments, $R^{11}$ and $R^{12}$ are 2-methylphenyl.

In certain embodiments, $R^{13}$ is hydrogen. In certain embodiments, $R^{13}$ is $C_{1-6}$ alkyl, optionally substituted with one or more substituents. In certain embodiments, $R^{13}$ is methyl.

In certain embodiments, $R^{14}$ is hydrogen. In certain embodiments, $R^{14}$ is $C_{1-6}$ alkyl, optionally substituted with one or more substituents. In certain embodiments, $R^{14}$ is methyl.

In certain embodiments, $R^{15}$ is hydrogen. In certain embodiments, $R^{15}$ is $C_{1-6}$ alkyl, optionally substituted with one or more substituents. In certain embodiments, $R^{15}$ is methyl.

In certain embodiments, $R^{16}$ is hydrogen. In certain embodiments, $R^{16}$ is $C_{1-6}$ alkyl, optionally substituted with one or more substituents. In certain embodiments. $R^{16}$ is methyl.

In certain embodiments, $R^{13}$, $R^{14}$, $R^{15}$, and $R^{16}$ are hydrogen. In certain embodiments, $R^{13}$, $R^{14}$, $R^{15}$, and $R^{16}$ are methyl.

In certain embodiments, L is one selected from:

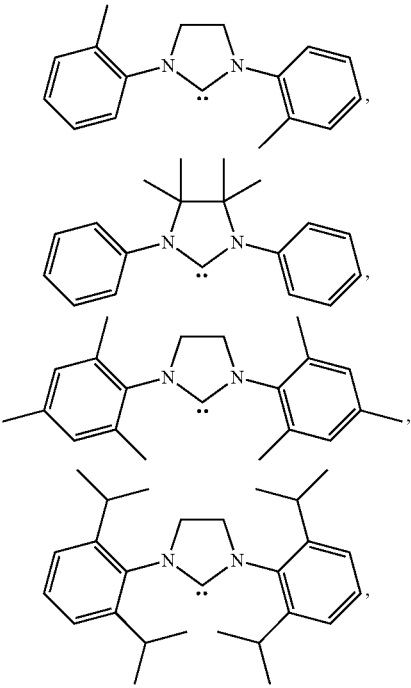

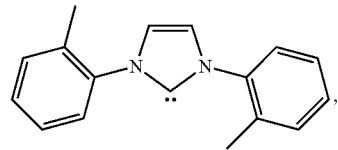

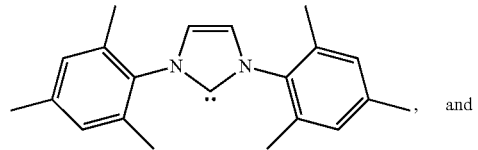, and

-continued

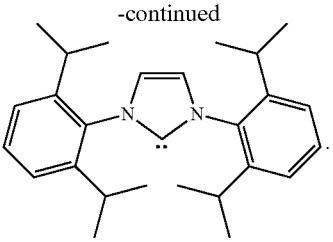

In certain embodiments, L is a phosphine. In certain embodiments, L is a P of $PR^{17}R^{18}R^{19}$, where $R^{17}$, $R^{18}$, and $R^{19}$ are each independently $C_{1-12}$ alkyl, $C_{3-10}$ cycloalkyl, or $C_{6-14}$ aryl, each optionally substituted with one or more substituents as described herein.

In certain embodiments, $R^{17}$ is $C_{1-12}$ alkyl, optionally substituted with one or more substituents as described herein. In certain embodiments, $R^{17}$ is $C_{3-10}$ cycloalkyl, optionally substituted with one or more substituents as described herein. In certain embodiments, $R^{17}$ is cyclohexyl. In certain embodiments, $R^{17}$ is $C_{6-14}$ aryl, optionally substituted with one or more substituents as described herein. In certain embodiments, $R^{17}$ is phenyl.

In certain embodiments, $R^{18}$ is $C_{1-12}$ alkyl, optionally substituted with one or more substituents as described herein. In certain embodiments, $R^{18}$ is $C_{3-10}$ cycloalkyl, optionally substituted with one or more substituents as described herein. In certain embodiments, $R^{18}$ is cyclohexyl. In certain embodiments, $R^{18}$ is $C_{6-14}$ aryl, optionally substituted with one or more substituents as described herein. In certain embodiments, $R^{18}$ is phenyl.

In certain embodiments, $R^{19}$ is $C_{1-12}$ alkyl, optionally substituted with one or more substituents as described herein. In certain embodiments, $R^{19}$ is $C_{3-10}$ cycloalkyl, optionally substituted with one or more substituents as described herein. In certain embodiments, $R^{19}$ is cyclohexyl. In certain embodiments, $R^{19}$ is $C_{6-14}$ aryl, optionally substituted with one or more substituents as described herein. In certain embodiments, $R^{19}$ is phenyl.

In certain embodiments, L is triphenylphosphine or tricyclohexylphosphine.

In certain embodiments, $X^1$ is halide. In certain embodiments, $X^1$ is fluoride, chloride, bromide, or iodide. In certain embodiments, $X^1$ is chloride. In certain embodiments, $X^1$ is —C(O)$R^x$ or —OC(O)$R^x$ where $R^x$ is $C_{1-6}$ alkyl, optionally substituted with one or more halides.

In certain embodiments, $X^2$ is halide. In certain embodiments, $X^2$ is fluoride, chloride, bromide, or iodide. In certain embodiments, $X^2$ is chloride. In certain embodiments, $X^2$ is —C(O)$R^x$ or —OC(O)$R^x$ where $R^x$ is $C_{1-6}$ alkyl, optionally substituted with one or more halides.

In certain embodiments, Y is a bond. In certain embodiments, Y is —$NR^b$—, wherein $R^b$ is as defined herein. In certain embodiments, Y is —NH—.

In certain embodiments, Z is O. In certain embodiments, Z is S.

In certain embodiments, n is 0. In certain embodiments, n is 1. In certain embodiments, n is 2. In certain embodiments, n is 3.

In one embodiment, provided herein is the ruthenium complex of Formula I, wherein:

L is a heterocyclic carbene or phosphine;

$R^1$ is $C_{1-5}$ alkyl, $C_{5-6}$ cycloalkyl, $C_{6-14}$ aryl, heteroaryl, heterocyclyl, or —$NR^{3b}R^{3c}$;

$R^2$ is $C_{1-5}$ alkyl or $C_{5-6}$ cycloalkyl;

$R^3$ is halo, cyano, nitro, —C(O)$OR^{3a}$, —$NR^{3a}S(O)_2R^{3b}$, —P(O)(OR$^{3a}$)$R^{3b}$, or —$SO_2NR^{3b}R^{3c}$;

$R^4$ is $C_{1-5}$ alkyl or $C_{5-6}$ cycloalkyl;

$R^5$ is hydrogen, $C_{1-5}$ alkyl, or $C_{5-6}$ cycloalkyl;

each $R^{3a}$, $R^{3b}$, and $R^{3c}$ is as defined herein;

$X^1$ and $X^2$ are each independently an anionic ligand;

Y is a bond or —$NR^b$—;

Z is O or S; and n is an integer of 0, 1, 2, or 3;

wherein each alkyl, aryl, cycloalkyl, heterocyclyl, heterocyclic carbene, and heteroaryl is optionally substituted with one or more substituents as described herein.

In another embodiment, provided herein is the ruthenium complex of Formula I, wherein:

L is triphenylphosphine, tricyclohexylphosphine, or a heterocyclic carbene selected from:

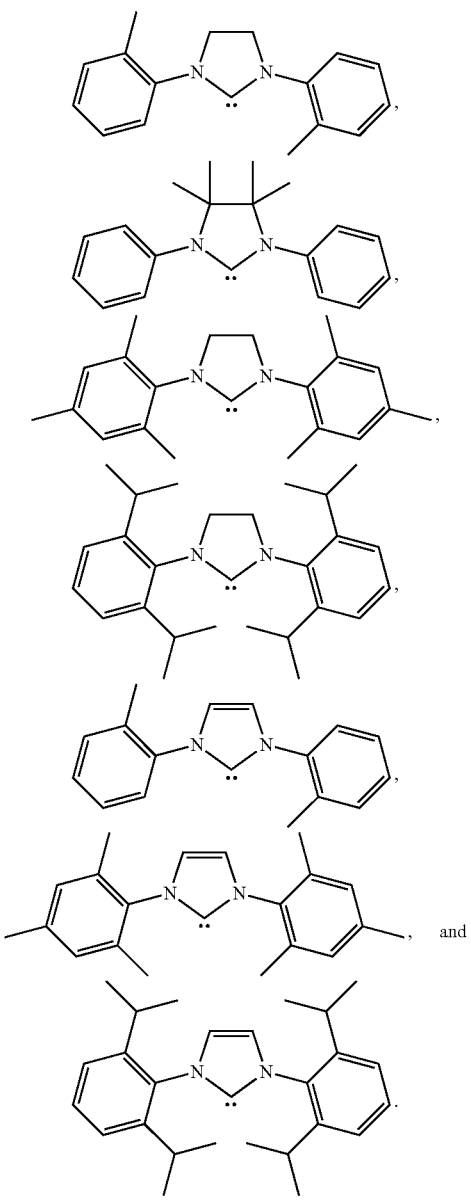

R$^1$ is C$_{1-5}$ alkyl, C$_{5-6}$ cycloalkyl, C$_{6-14}$ aryl, heteroaryl, heterocyclyl, or —NR$^{3b}$R$^{3c}$;

R$^2$ is C$_{1-5}$ alkyl or C$_{5-6}$ cycloalkyl;

R$^3$ is halo, cyano, nitro, —C(O)OR$^{3a}$, —NR$^{3a}$S(O)$_2$R$^{3b}$, —P(O)(OR$^{3a}$)R$^{3b}$, or —SO$_2$NR$^{3b}$R$^3$;

R$^4$ is C$_{1-5}$ alkyl or C$_{5-6}$ cycloalkyl;

R$^5$ is hydrogen, C$_{1-5}$ alkyl, or C$_{5-6}$ cycloalkyl;

each R$^{3a}$, R$^{3b}$, and R$^{3c}$ is as defined herein;

X$^1$ and X$^2$ are each independently an anionic ligand;

Y is a bond or —NR$^b$—;

Z is O or S; and n is an integer of 0, 1, 2, or 3;

wherein each alkyl, aryl, cycloalkyl, heterocyclyl, and heteroaryl is optionally substituted with one or more substituents as described herein.

In yet another embodiment, provided herein is the ruthenium complex of Formula I, wherein:

L is triphenylphosphine, tricyclohexylphosphine, or a heterocyclic carbene selected from:

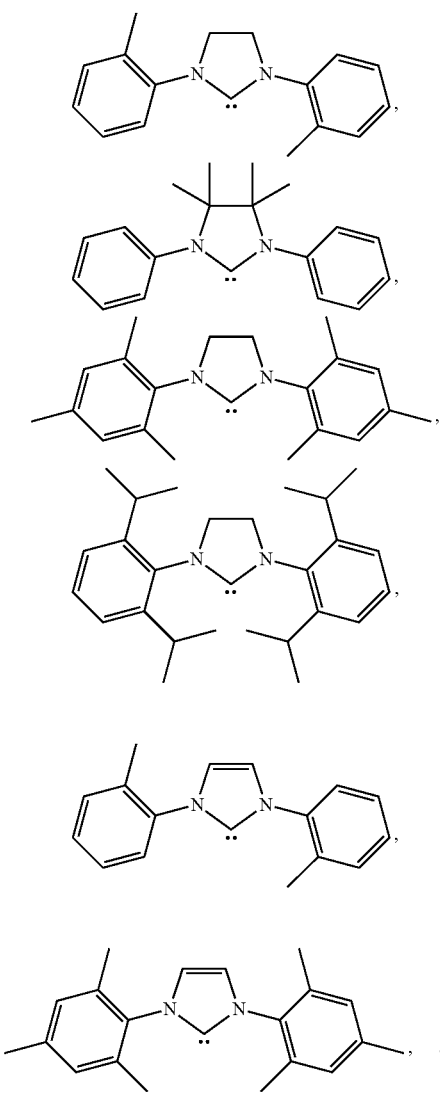

and

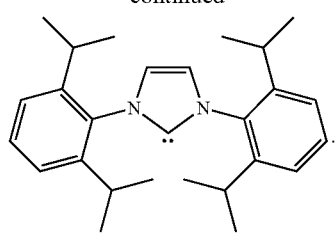

R$^1$ is trifluoromethyl, phenyl, cyanophenyl, fluorophenyl, difluorophenyl, trifluoromethylphenyl, bis(trifluoromethyl)phenyl, methoxyphenyl, trifluoromethylsulfonylphenyl, trifluoroacetylphenyl, nitrophenyl, dinitrophenyl, trifluoroacetamidophenyl, pentofluorophenyl, pyridyl, trifluoromethylthiazolyl, trifluoromethyl-pyrazolyl, or dimethylamino;

R$^2$ is ethyl;

R$^4$ is isopropyl;

R$^5$ is hydrogen;

Y is a bond or —NH—;

X$^1$ and X$^2$ are chloride;

Z is O; and n is 0.

In yet another embodiment, provided herein is the ruthenium complex of Formula I, wherein:

L is triphenylphosphine, tricyclohexylphosphine, or a heterocyclic carbene selected from:

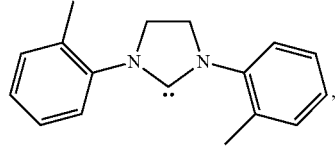

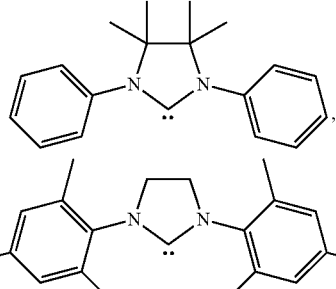

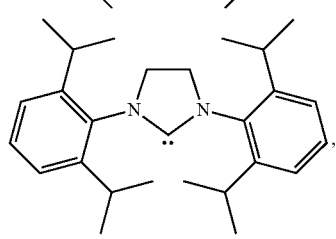

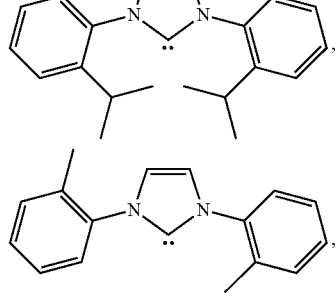

-continued

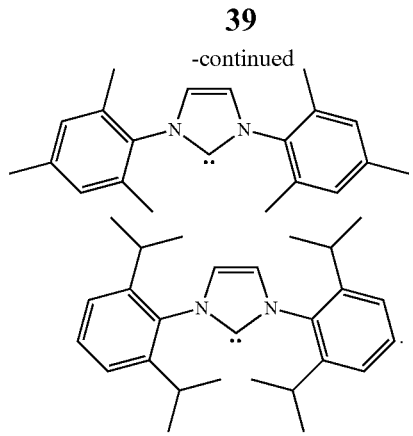
, and $R^1$ is phenyl, 4-cyanophenyl, 4-fluorophenyl, 3,5-difluorophenyl, 4-trifluoromethylphenyl), 3,5-bis(trifluoromethyl)phenyl, 4-methoxyphenyl, 4-trifluoromethylsulfonylphenyl, 4-trifluoroacetylphenyl, 4-nitrophenyl, 3,5-dinitrophenyl, 4-trifluoroacetamidophenyl, pentofluorophenyl, pyridyl, 4-trifluoromethylthiazolyl, 3-trifluoromethyl-pyrazolyl, or dimethylamino;

$R^2$ is ethyl;

$R^4$ is isopropyl;

$R^5$ is hydrogen;

$X^1$ and $X^2$ are chloride;

Y is a bond or —NH—;

Z is O; and n is 0.

In still another embodiment, provided herein is a ruthenium complex selected from:

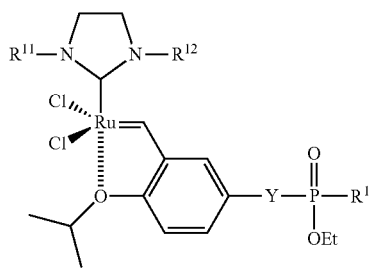

wherein:

| Cmpd No. | Y | $R^1$ | $R^{11}$ | $R^{12}$ |
|---|---|---|---|---|
| AP | A bond | | Mes | Mes |
| AQ | A bond | *—⌬ | Mes | Mes |
| AR | A bond | *—⌬—F | Mes | Mes |
| AT | A bond | *—⌬(CF_3)(CF_3) | Mes | Mes |
| C5 | A bond | —N(CH_3)_2 | Mes | Mes |
| D4 | A bond | *—⌬—OCH_3 | Mes | Mes |
| E6 | —NH— | *—⌬ | Mes | Mes |
| G2 | A bond | *—⌬ | 2-MePh | 2-MePh |

Mes: 2,4,6-trimethylphenyl
2-MePh: 2-methylphenyl

In one embodiment, provided herein is the compound of Formula II, wherein:

$R^1$ is $C_{1-5}$ alkyl, $C_{5-6}$ cycloalkyl, $C_{6-14}$ aryl, heteroaryl, heterocyclyl, or —$NR^{3b}R^{3c}$;

$R^2$ is $C_{1-5}$ alkyl or $C_{5-6}$ cycloalkyl;

$R^3$ is halo, cyano, nitro, —C(O)$OR^{3a}$, —$NR^{3a}S(O)_2R^{3b}$, —P(O)(OR^{3a})R^{3b}$, or —$SO_2NR^{3b}R^{3c}$;

$R^4$ is $C_{1-5}$ alkyl or $C_{5-6}$ cycloalkyl;

$R^5$ is hydrogen, $C_{1-5}$ alkyl, or $C_{5-6}$ cycloalkyl;

$R^6$ and $R^7$ are independently hydrogen or $C_{1-6}$ alkyl;

each $R^{3a}$, $R^{3b}$, and $R^{3c}$ is as defined herein;

Y is a bond or —NH—;

Z is O or S; and n is an integer of 0, 1, 2, or 3;

wherein each alkyl, aryl, cycloalkyl, heterocyclyl, heterocyclic carbene, and heteroaryl is optionally substituted with one or more substituents as described herein.

In another embodiment, provided herein is the compound of Formula II, wherein:

$R^1$ is $C_{1-5}$ alkyl, $C_{5-6}$ cycloalkyl, $C_{6-14}$ aryl, heteroaryl, heterocyclyl, or —$NR^{3b}R^{3c}$;

$R^2$ is $C_{1-5}$ alkyl or $C_{5-6}$ cycloalkyl;

$R^3$ is halo, cyano, nitro, —C(O)$OR^{3a}$, —$NR^{3a}S(O)_2R^{3b}$, —P(O)(OR^{3a})R^{3b}$, or —$SO_2NR^{3b}R^{3c}$; $R^4$ is $C_{1-5}$ alkyl or $C_{5-6}$ cycloalkyl;

$R^5$ is hydrogen, $C_{1-5}$ alkyl, or $C_{5-6}$ cycloalkyl;

$R^6$ and $R^7$ are independently hydrogen or $C_{1-6}$ alkyl;

each $R^{3a}$, $R^{3b}$, and $R^{3c}$ is as defined herein;

Y is a bond or —NH—;

Z is O or S; and n is an integer of 0, 1, 2, or 3;

wherein each alkyl, aryl, cycloalkyl, heterocyclyl, and heteroaryl is optionally substituted with one or more substituents as described herein.

In yet another embodiment, provided herein is the compound of Formula II, wherein:

$R^1$ is trifluoromethyl, phenyl, cyanophenyl, fluorophenyl, difluorophenyl, trifluoromethylphenyl, bis(trifluoromethyl)phenyl, methoxyphenyl, trifluoromethylsulfonylphenyl, trifluoroacetylphenyl, nitrophenyl, dinitrophenyl, trifluoroacetamidophenyl, pentofluorophenyl, pyridyl, trifluoromethyl-thiazolyl, trifluoromethyl-pyrazolyl, or dimethylamino;

$R^2$ is ethyl;
$R^4$ is isopropyl;
$R^5$ is hydrogen;
$R^6$ and $R^7$ are hydrogen;
Y is a bond or —NH—;
Z is O; and
n is 0.

In yet another embodiment, provided herein is the compound of Formula II, wherein:

$R^1$ is phenyl, 4-cyanophenyl, 4-fluorophenyl, 3,5-difluorophenyl, 4-trifluoromethylphenyl), 3,5-bis(trifluoromethyl)phenyl, 4-methoxyphenyl, 4-trifluoromethylsulfonylphenyl, 4-trifluoroacetylphenyl, 4-nitrophenyl, 3,5-dinitrophenyl, 4-trifluoroacetamidophenyl, pentotluorophenyl, pyridyl, 4-trifluoromethylthiazolyl, 3-trifluoromethyl-pyrazolyl, or dimethylamino;

$R^2$ is ethyl;
$R^4$ is isopropyl;
$R^5$ is hydrogen;
$R^6$ and $R^7$ are hydrogen;
Y is a bond or —NH—;
Z is O; and
n is 0.

In still another embodiment, provided herein is a compound selected from:

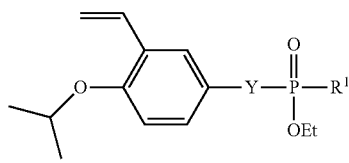

wherein:

| Cmpd No. | Y | $R^1$ |
|---|---|---|
| BA1 | A bond | *—⌬—CF$_3$ |
| BA4 | A bond | *—⌬ |
| BA2 | A bond | *—⌬—F |
| BA3 | A bond | *—⌬(CF$_3$)(CF$_3$) |
| C4 | A bond | —N(CH$_3$)$_2$ |
| D3 | A bond | *—⌬—OCH$_3$ |

-continued

| Cmpd No. | Y | $R^1$ |
|---|---|---|
| E5 | —NH— | *—⌬ |

The compounds provided herein are intended to encompass all possible stereoisomers, unless a particular stereochemistry is specified. Where the compound provided herein contains an alkenyl or alkenylene group, the compound may exist as one or a mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

In certain embodiments, the compound of Formula I, where $R^4$ is —$C(R^{4a}R^{4b})C(O)NR^{4c}R^{4d}$, also encompasses the structure of:

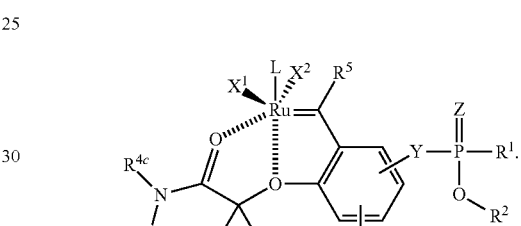

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

Methods of Synthesis

The compound provided herein can be prepared, isolated, or obtained by any method known to one of skill in the art. For an example, compounds of Formulae I to IV can be prepared as shown in Scheme 1.

Scheme 1

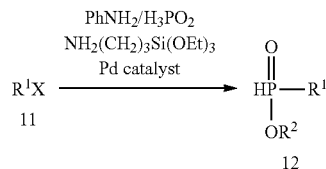

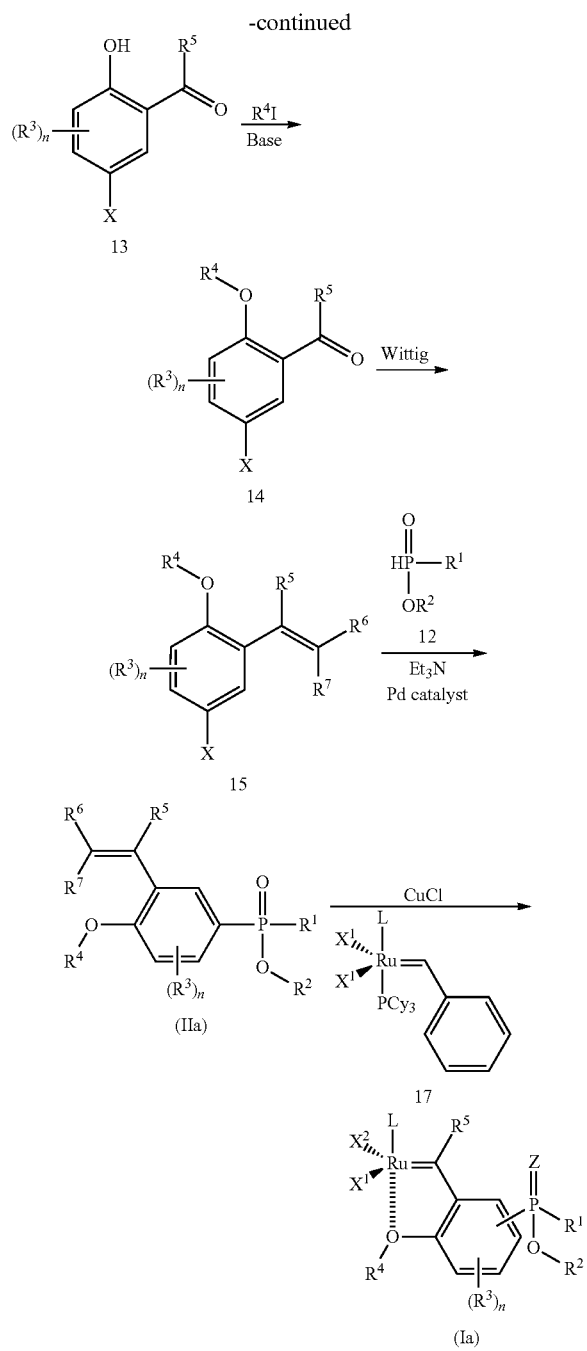

Olefin Metathesis

In one embodiment, provided herein is a method for catalyzing an olefin metathesis reaction, which comprises the step of contacting an olefin compound with a ruthenium complex of Formula I. In certain embodiments, the olefin compound has one terminal olefin group. In certain embodiments, the molar ratio between the ruthenium complex of Formula I and the olefin compound is no greater than about 0.5, no greater than about 0.4, no greater than about 0.3, no greater than about 0.2, no greater than about 0.1, no greater than about 0.08, no greater than about 0.06, no greater than about 0.05, no greater than about 0.04, no greater than about 0.03, no greater than about 0.02, or no greater than about 0.01.

In another embodiment, provided herein is a method for catalyzing a ring closure metathesis, which comprises the step of contacting an olefin compound having two or more olefin groups with a ruthenium complex of Formula I. In certain embodiments, the olefin compound has one terminal olefin group. In certain embodiments, the olefin compound has two terminal olefin groups. In certain embodiments, the molar ratio between the ruthenium complex of Formula I and the olefin compound is no greater than about 0.5, no greater than about 0.4, no greater than about 0.3, no greater than about 0.2, no greater than about 0.1, no greater than about 0.08, no greater than about 0.06, no greater than about 0.05, no greater than about 0.04, no greater than about 0.03, no greater than about 0.02, or no greater than about 0.01.

The ruthenium complex of Formula I as an olefin metathesis catalyst provides several advantages over the existing metathesis catalysts. In certain embodiments, the ruthenium complex of Formula I provides better catalytic efficiency for either olefin metathesis or ring closure metathesis reaction. In certain embodiments, the ruthenium complex of Formula I provides better yield for either olefin metathesis or ring closure metathesis reaction. In certain embodiments, the ruthenium complex of Formula I provides better chiral purity of the desired product produced via either olefin metathesis or ring closure metathesis reaction. In certain embodiments, the ruthenium complex of Formula I provides less metal contamination in the desired product produced via either olefin metathesis or ring closure metathesis reaction.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); eq. (equivalent); hr or hrs (hours); min (minutes); MS (mass spectrometry); NMR (nuclear magnetic resonance); ESI (electrospray ionization); ACN, (acetonitrile); $CDCl_3$ (deuterated chloroform); DCE (dichloroethane); DCM (dichloromethane); DMF (N,N-dimethylformamide); DMSO (dimethylsulfoxide); DMSO-$d_6$ (deuterated dimethylsulfoxide); EtOAc (ethyl acetate); MeOH (methanol); THF (tetrahydrofuran); DIPEA (N,N-diisopropylethylamine); TEA (triethylamine); DBU (1,8-diazabicyclo[5.4.0]undec-7-ene; CDI (carbonyldiimidazole); EDCI or EDC (N'-ethyl-N-(3-dimethylaminopropyl)-carbodiimide); $P_2O_5$, (phosphorus pentoxide); TBAF (tetrabutylammonium fluoride); TBTU (O-(benzotriazol-1-yl)-N,N,N',N'-tetramethyluronium tetrafluoroborate); Me (methyl); Et (ethyl); iPr, (isopropyl); tBu (tert-butyl); Boc (tert-butoxylcarbony); Bn (benzyl); PMB (p-methoxybenzyl); TsO (tosylate); DEAD (diethylazodicarboxylate), DIAD (diisopropylazodicarboxylate), $PPh_3$ (triphenylphosphine), PNBA (p-nitrobenzoic acid), PNB (p-nitrobenzoyl), and Mes (mesityl or 2,4,6-trimethylphenyl).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies illustrated in the schemes shown herein are intended to exemplify the applicable chemistry through the use of specific examples and are not indicative of the scope of the disclosure.

Example 1

Synthesis of Ruthenium Complexes

Ruthenium complexes, such as AP, AQ, AR, and AT, were prepared as shown in Scheme 2.

Step A: Preparation of 5-bromo-2-isopropoxybenzaldehyde AX. To a suspension of potassium carbonate (34.4 g, 249 mmol) and cesium carbonate (16.2 g, 50 mmol) in dimethylformamide were added 5-bromosalicaldehyde (25.0 g, 124 mmol) and 2-iodopropane (25.0 mL, 249 mmol). The suspension was stirred at room temperature overnight, then at 70° C. for 4 hrs. The volatiles were removed, and the residue was partitioned between methyl t-butylether and water. The aqueous layer was extracted with methyl t-butylether and the combined organic phases were washed with water, sodium hydroxide, and brine, and then dried over magnesium sulfate. Concentration to dryness afforded compound AX (30.0 g) as a pale yellow oil in 99% yield. $^1$H NMR (CDCl$_3$, 400 MHz): δ (ppm) 1.40 (d, J=6.3 Hz, 6H), 4.65 (sept., J=6.0 Hz, 1H), 6.89 (d, J=9.0 Hz, 1H), 7.59 (dd, J=9.0 and 2.7 Hz, 1H), 7.91 (d, J=2.7 Hz, 1H), 10.39 (s, 1H).

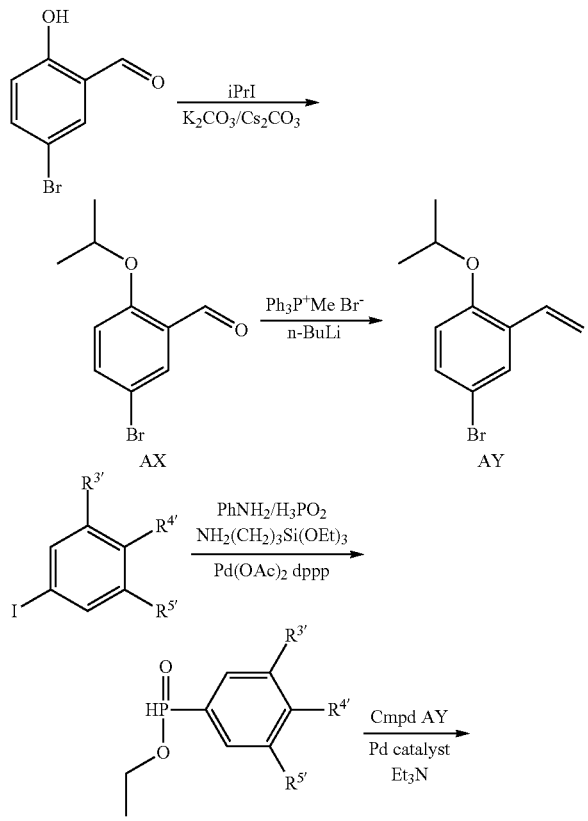

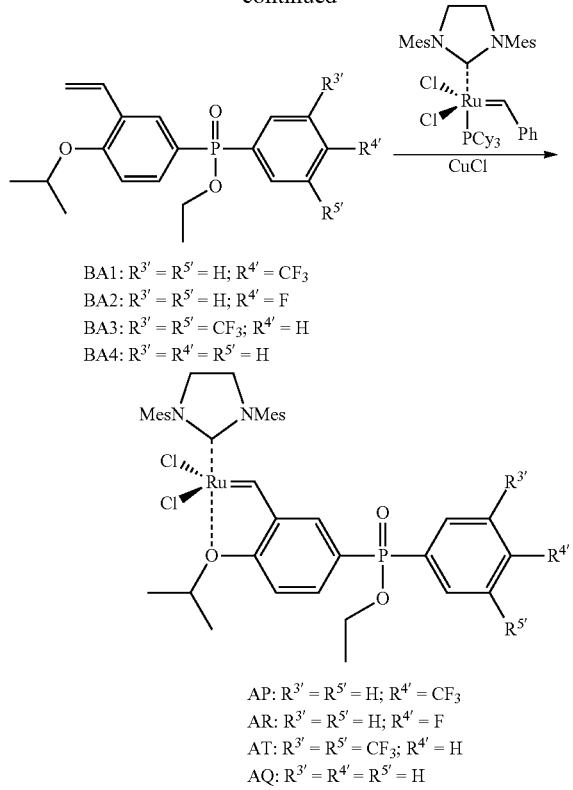

Step B: Preparation of 4-bromo-1-isopropoxy-2-vinylbenzene AY. To a suspension of methyltriphenylphosphonium bromide (41.1 g, 115 mmol) in anhydrous THF (1.2 L) was added n-butyllithium (123 mmol, 2.5 M in hexanes) at −70° C. The mixture was stirred for a further 10 min, and then allowed to warm up to 0° C. and stirred at this temperature for 10 min. The reaction mixture is then cooled again at −50° C., and 5-bromo-2-isopropoxybenzaldehyde (20.0 g, 82.2 mmol) in solution in anhydrous THF (5 mL) was added. The mixture was stirred for 10 min, and then allowed to warm up to room temperature. An ammonium chloride solution was added and the reaction mixture was diluted with a mixture methyl t-butylether/hexane, filtered through celite, and then dried over magnesium sulfate. The solvent was removed in vacuo to afford compound AY (18.9 g) as a pale yellow oil in 95% yield. $^1$H NMR (CDCl$_3$, 400 MHz): δ (ppm) 1.34 (d, J=6.0 Hz, 6H), 4.50 (sept., J=6.0 Hz, 1H), 5.27 (dd, J=11.0 and 1.1 Hz, 1H), 5.71 (dd, J=17.9 and 1.2 Hz, 1H), 6.75 (d, J=8.7 Hz, 1H), 6.97 (dd, J=17.7 and 11.2 Hz, 1H), 7.28 (dd, J=8.7 and 2.5 Hz, 1H), 7.57 (d, J=2.5 Hz, 1H).

Preparation of Ruthenium Complex AP

Step A: Preparation of ethyl 4-(trifluoromethyl)phenylphosphinate AZ1. To a degassed solution of 4-iodobenzotrifluoride (4.70 g, 17.2 mmol), anilinium hypophosphite (3.51 g, 22.1 mmol), and 3-aminopropyl triethoxysilane (4.88 g, 22.1 mmol) in anhydrous acetonitrile (110 mL) were added palladium acetate (82.5 mg, 0.367 mmol, 2 mol %) and 1,3-bis(diphenylphosphino)propane (167 mg, 0.404 mol, 2.2 mol %). The mixture was refluxed for 32 hrs. After cooling down to room temperature, the reaction mixture was diluted with ethyl acetate and hydrochloric acid (1M), and partitioned. The aqueous layer was further extracted with ethyl acetate. The combined extracts were washed sequentially with aqueous sodium hydrogen carbonate and brine, dried over magnesium sulfate, and concentration in vacuo. The resulting residue was purified by column chromatography using 25 to 100% ethyl acetate in petroleum ether. Further purification by distillation afforded compound AZ1 (1.14 g) in 28% yield. $^1$H NMR (CDCl$_3$, 400 MHz): δ (ppm) 1.35-1.43 (m, 3H), 4.12-4.27 (m, 2H), 7.63 (d, J=570.8 Hz, 1H), 7.75-7.80 (m, 2H), 7.90-7.94 (m, 2H); $^{31}$P NMR (CDCl$_3$, 161.8 MHz): δ (ppm) 22.6.

Step B: Preparation of ethyl [4-(trifluoromethyl)phenyl]-{4-(isopropoxy)-3-vinylphenyl}phosphinate BA1. To a degassed solution of ethyl 4-(trifluoromethyl)-phenylphosphinate (1.00 g, 4.20 mmol) and 4-bromo-1-isopropoxy-2-vinylbenzene (921 mg, 3.81 mmol) in DMF (40 mL) were added the triethylamine (1.1 mL, 7.62 mmol) and tris(dibenzylideneacetone)dipalladium (698 mg, 0.762 mmol). The mixture was heated at 70° C. overnight. The volatiles were removed in vacuo and the residue was purified by column chromatography using 5 to 100% ethyl acetate in petroleum ether to afford compound BA1 (130 mg) as a dark green oil in 8.6% yield. $^1$H NMR (CDCl$_3$, 400 MHz): δ (ppm) 1.37 (d, J=6.0 Hz, 6H), 1.38 (t, J=7.1 Hz, 3H), 4.07-4.17 (m, 2H), 4.63 (sept., J=6.1 Hz, 1H), 5.31 (dd, J=11.2 and 1.1 Hz, 1H), 5.79 (dd, J=17.7 and 1.1 Hz, 1H), 6.92 (dd, J=8.6 and 3.1 Hz, 1H), 6.99 (dd, J=17.3 and 10.8 Hz, 1H), 7.59-7.66 (m, 1H), 7.67-7.72 (m, 2H), 7.87-7.96 (m, 3H); $^{31}$P NMR (CDCl$_3$, 161.8 MHz): δ (ppm) 30.7.

Step C: Preparation of 1,3-bis(2,4,6-trimethylphenyl)-4,5-dihydroimidazol-2-ylidene[2-(i-propoxy-5-(4-trifluoromethylphenyl ethylphosphite))phenyl]methylene-ruthenium (II) dichloride AP. Grubbs' 2nd generation catalyst (277 mg, 0.326 mmol) and copper (I) chloride were charged in a Schlenk tube and degassed. A degassed solution of ethyl [4-(trifluoromethyl)phenyl]-{4-(isopropoxy)-3-vinylphenyl}phosphinate BA1 (130 mg, 0.326 mmol) in anhydrous dichloromethane (17 mL) was transferred via cannula to the solids. The mixture was heated at 30° C. for 70 mitt. The solvent was removed in vacuo and the residue was purified by column chromatography using 20 to 66% ethyl acetate in petroleum ether to afford compound AP (115 mg) as a green powder in 41% yield. $^1$H NMR (CDCl$_3$, 400 MHz): δ (ppm) 1.26 (d, J=6.0 Hz, 6H), 1.39 (t, J=7.0 Hz, 3H), 2.38 (br s) and 2.45 (br s) (18H), 4.07-4.16 (m, 2H), 4.19 (br s, 4H), 4.93 (sept., J=6.0 Hz, 1H), 6.88 (br dd, J=8.5 and 2.0 Hz, 1H), 7.05 (br s, 4H), 7.27-7.47 (m, 3H), 7.86-7.99 (m, 3H), 16.4 (br s, 1H); $^{31}$P NMR (CDCl$_3$, 161.8 MHz): δ (ppm) 29.0.

Preparation of Ruthenium Complex AR

Step A: Preparation of ethyl 4-fluorophenylphosphinate AZ2. To a degassed mixture of 4-fluoro-1-iodo-benzene (25.0 g, 112.6 mmol), anilinium hypophosphite (21.5 g, 135.1 mmol) and 3-aminopropyl triethoxysilane (24.9 g, 135.1 mmol) in anhydrous acetonitrile (750 mL) were added palladium acetate (560 mg, 2.48 mmol) and 1,3-bis(diphenylphosphino)propane (1.02 g, 2.48 mmol). The mixture was refluxed overnight. After cooling down to room temperature, the reaction mixture was concentrated in vacuo. The residue was diluted with ethyl acetate and hydrochloric acid (1M) and partitioned. The aqueous layer was further extracted with ethyl acetate and the combined extracts were washed sequentially with aqueous sodium hydrogen carbonate and brine. The volatiles were removed in vacuo, and then the residue was purified by column chromatography using 50 to 100% ethyl acetate in petroleum ether, affording compound AZ2 (10.1 g) as a dark orange oil in 48% yield. $^1$H NMR (CDCl$_3$, 400 MHz): δ (ppm) 1.84 (t, J=7.1 Hz, 3H), 4.08-4.24 (m, 2H), 7.20 (td, J=8.7 and 2.5 Hz, 2H), 7.58 (d, J=566.6 Hz, 1H), 7.74-7.85 (m, 2H); $^{31}$P NMR (CDCl$_3$, 161.8 MHz): δ (ppm) 23.62 (J=566.8 Hz).

Step B: Preparation of ethyl (4-fluorophenyl)-[4-{isopropoxy}-3-vinylphenyl]-phosphinate BA2. To a degassed mixture of 4-fluoro-phenylphosphinate AZ2 (2.07 g, 11.0 mmol) and 4-bromo-1-isopropoxy-2-vinylbenzene (2.43 g, 10.0 mmol) in acetonitrile (66 mL) were added triethylamine (3.1 mL, 22.0 mmol), palladium acetate (112 mg, 0.5 mmol), and 1,1'-bis(diphenylphosphino)ferrocene (277 mg, 0.5 mmol). The mixture was heated at 68° C. for 24 hrs. The volatiles were removed in vacuo, and the residue was purified by column chromatography using 40 to 80% ethyl acetate in petroleum ether to afford 2.84 g of compound BA2 in 82% yield. $^1$H NMR (CDCl$_3$, 400 MHz): δ (ppm) 1.36 (d, J=6.0 Hz, 6H), 1.38 (t, J=7.1 Hz, 3H), 4.02-4.15 (m, 2H), 4.62 (sept., J=6.0 Hz, 1H), 5.29 (dd, J=11.2 and 1.1 Hz, 1H), 5.78 (dd, J=17.7 and 1.4 Hz, 1H), 6.91 (dd, J=8.7 and 3.0 Hz, 1H), 6.99 (dd, J=17.4 and 10.9 Hz, 1H), 7.12 (td, J=8.8 and 2.5 Hz, 2H), 7.61 (ddd, J=11.7, 8.6 and 1.9 Hz, 1H), 7.75-7.84 (m, 2H), 7.88 (dd, J=12.5 and 1.9 Hz, 1H); $^{31}$P NMR (CDCl$_3$, 161.8 MHz): δ (ppm) 30.71.

Step C: Preparation of 1,3-bis(2,4,6-trimethylphenyl)-4,5-dihydroimidazol-2-ylidene[2-(i-propoxy-5-({4-fluorophenyl}ethylphosphite))phenyl]methyleneruthenium (II) dichloride AR. Grubbs' second generation catalyst (2.00 g, 2.36 mmol) and copper (I) chloride (233 mg, 2.36 mmol) were charged in a Schlenk tube and degassed. A degassed solution of ethyl phenyl-{4-(isopropoxy)-3-vinylphenyl}phosphinate (822 mg, 2.36 mmol) in anhydrous dichloromethane (120 mL) was transferred via cannula to the solids. The mixture was heated at 30° C. for 60 min. The solvent was removed in vacuo and the residue was purified by column chromatography using 30 to 60% ethyl acetate in petroleum ether to afford compound AR (552 mg) in 29% yield. $^1$H NMR (CDCl$_3$, 400 MHz): δ (ppm) 1.27 (d, J=6.1 Hz, 6H), 1.37 (t, J=7.0 Hz, 3H), 2.39 (br s) and 2.45 (br s) (18H), 3.98-4.15 (m, 2H), 4.19 (br s, 4H), 4.93 (sept., J=6.0 Hz, 1H), 6.87 (d, J=8.2 Hz, 1H), 7.05 (br s, 4H), 7.15 (dt, J=8.6 and 2.2 Hz, 2H), 7.29 (d, J=11.9 Hz, 1H), 7.72-7.81 (m, 2H), 7.91-7.99 (m, 1H), 16.44 (s, 1H); $^{31}$P NMR (CDCl$_3$, 161.8 MHz): δ (ppm) 29.94.

Preparation of Ruthenium Complex AT

Step A: Preparation of ethyl 3,5-bis(trifluoromethyl)phenylphosphinate AZ3. To a degassed solution of 1-iodo-3,5-bistrifluoromethylbenzene (10.0 g, 29.4 mmol), anilinium hypophosphite (5.62 g, 35.3 mmol) and 3-aminopropyl triethoxysilane (7.81 g, 35.3 mmol) in anhydrous acetonitrile (200 mL) were added palladium acetate (132 mg, 0.588 mmol, 2 mol %) and 1,3-bis(diphenylphosphino)propane (267 mg, 0.647 mol, 2.2 mol %). The mixture was refluxed overnight. After cooling down to room temperature, the reaction mixture was diluted with ethyl acetate and hydrochloric acid (IM), and then partitioned. The aqueous layer was further extracted with ethyl acetate. The combined extracts were washed sequentially with aqueous sodium hydrogen carbonate and brine, and dried over sodium sulfate. The volatiles were removed in vacuo, and the residue was purified by column chromatography using 30 to 70% ethyl acetate in petroleum ether to afford compound AZ3 (4.65 g) as a cloudy oil in 52% yield. $^1$H NMR (CDCl$_3$, 400 MHz): δ (ppm) 1.45 (t, J=7.1 Hz, 3H), 4.18-4.35 (m, 2H), 7.69 (d, J=579.6 Hz, 1H), 8.10 (s, 1H), 8.23 (s, 1H), 8.27 (s, 1H); $^{31}$P NMR (CDCl$_3$, 161.8 MHz): δ (ppm) 19.59 (J=580.6 Hz).

Step B: Preparation of ethyl [3,5-bis(trifluoromethyl)phenyl]-{4-(isopropoxy)-3-vinylphenyl}phosphinate BA3. To a degassed solution of ethyl 3,5-bis(trifluoromethyl)-phenylphosphinate (3.33 g, 15.24 mmol) and 4-bromo-1-isopropoxy-2-vinylbenzene (3.33 mg, 13.8 mmol) in DMF (25 mL) were added the triethylamine (3.85 mL, 27.6 mmol) and tris(dibenzylideneacetone)dipalladium (2.53 g, 2.76 mmol). The mixture was heated in an oil bath at 70° C. overnight. The volatiles were removed in vacuo and the mixture was purified by column chromatography with 20 to 70% ethyl acetate in petroleum ether to afford compound BA3 (185 mg) as an oil in 2.8% yield. $^1$H NMR (CDCl$_3$, 400 MHz): δ (ppm) 1.38 (dd, J=6.1 and 1.4 Hz, 6H) overlapping 1.41 (t, J=7.1 Hz, 3H), 4.11-4.21 (m, 2H), 4.65 (sept., J=6.1 Hz, 1H), 5.33 (dd, J=11.2 Hz and 1.4 Hz, 1H), 5.80 (dd, J=17.9 and 1.2 Hz, 1H), 6.96 (dd, J=8.6 and 3.0 Hz, 1H) overlapping 7.00 (dd, J=18.0 and 11.4 Hz, 1H), 7.63 (ddd, J=11.9, 11.9 and 2.0 Hz, 1H), 7.90 (dd, J=12.7 and 2.1 Hz, 1H), 7.99 (s, 1H), 8.22 (s, 1H), 8.25 (s, 1H); $^{31}$P NMR (CDCl$_3$, 161.8 MHz): δ (ppm) 28.59.

Step C: Synthesis of 1,3-bis(2,4,6-trimethylphenyl)-4,5-dihydroimidazol-2-ylidene[2-(i-propoxy)-5-(3,5-bis(trifluoromethyl)phenyl ethylphosphite))phenyl]methylene-ruthenium (II) dichloride AT. Grubbs' second generation catalyst (326 mg, 0.384 mmol), and copper (I) chloride (38 mg, 0.384 mmol) were charged in a Schlenk tube and degassed. A degassed solution of ethyl [3,5-bis(trifluoromethyl)phenyl]-{4-(isopropoxy)-3-vinylphenyl}-phosphinate (179 mg, 0.384 mmol) in anhydrous dichloromethane (20 mL) was transferred via cannula to the solids. The mixture was heated at 30° C. for 70 min. The solvent was removed in vacuo and the residue was purified by column chromatography with 20 to 80% ethyl acetate in petroleum ether to afford compound AT (185 mg) as a green powder in 52% yield. $^1$H NMR (CDCl$_3$, 400 MHz): δ (ppm) 1.26 (dd, J=6.0 and 4.0 Hz, 6H), 1.43 (t, J=7.0 Hz, 3H), 2.41 (br s) and 2.44 (br s) (18H), 4.07-4.25 (m, 2H) overlapping 4.20 (br s, 4H), 4.94 (sept., J=6.1 Hz, 1H), 6.91 (dd, J=8.5 and 2.4 Hz, 1H), 7.06 (br s, 4H), 7.29 (dd, J=11.9 and 1.7 Hz, 1H), 8.02 (br s, 1H), 8.03 (m, 1H), 8.20 (s, 1H), 8.23 (s, 1H), 16.40 (s, 1H); $^{31}$P NMR (CDCl$_3$, 161.8 MHz): δ (ppm) 26.33.

Preparation of Ruthenium Complex AQ

Step A: Preparation of ethyl phenyl-{4-(isopropoxy)-3-vinylphenyl}phosphinate BA4. To a degassed mixture of ethyl phenylphosphinate (1.87 g, 11.0 mmol) and 4-bromo-1-isopropoxy-2-vinylbenzene (2.43 g, 10.0 mmol), which was commercially available, in acetonitrile (66 mL) were added triethylamine (3.1 mL, 22.0 mmol), palladium acetate (112 mg, 0.5 mmol), and 1,1'-bis(diphenylphosphino)ferrocene (277 mg, 0.5 mmol). The mixture was further degassed and heated at 68° C. for 24 hrs. The volatiles were removed in vacuo and the crude was purified by column chromatography using 50 to 80% ethyl acetate in petroleum ether to afford compound BA4 (3.74 g) in 87% yield. $^1$H NMR (CDCl$_3$, 400 MHz): δ (ppm) 1.36 (d, J=5.7 Hz, 6H), 1.37 (t, J=6.9 Hz, 3H), 4.15-4.05 (m, 2H), 4.62 (sept., J=6.0 Hz, 1H), 5.28 (dd, J=11.2 and 1.4 Hz, 1H), 5.78 (dd, J=17.7 and 1.4 Hz, 1H), 6.91 (dd, J=8.45 and 3.0 Hz, 1H), 6.99 (dd, J=17.9 and 11.4 Hz, 1H), 7.41-7.47 (m, 2H), 7.47-7.55 (m, 1H), 7.63 (ddd. J=11.7, 8.5 and 2.0 Hz, 1H), 7.79 (dd, J=12.3 and 1.4 Hz, 1H), 7.81 (dt, J=12.3 and 1.4 Hz, 1H), 7.90 (dd, J=12.4 and 2.0 Hz, 1H); $^{31}$P NMR (CDCl$_3$, 161.8 MHz): δ (ppm) 32.61.

Step B: Preparation of 1,3-bis(2,4,6-trimethylphenyl)-4,5-dihydroimidazol-2-ylidene[2-(i-propoxy)-5-(phenyl ethylphosphite))phenyl]methyleneruthenium (II) dichloride AQ. Grubbs' second generation catalyst (2.00 g, 2.36 mmol) and copper (I) chloride (233 mg, 2.36 mmol) were charged in a Schlenk tube and degassed. A degassed solution of ethyl phenyl-{4-(isopropoxy)-3-vinylphenyl}phosphinate BA4 (778 mg, 2.36 mmol) in anhydrous dichloromethane (120 mL) was transferred via cannula to the solids. The mixture was heated at 30° C. for 60 min. The solvent was removed in vacuo and the residue was purified by column chromatography using 40 to 100% ethyl acetate in petroleum ether to afford compound AQ (775 mg) in 41% yield. $^1$H NMR (CDCl$_3$, 400 MHz): δ (ppm) 1.27 (d, J=6.1 Hz, 6H), 1.37 (t, J=7.0 Hz, 3H), 2.39 (br s) and 2.47 (br s) (18H), 3.98-4.17 (m, 2H), 4.18 (br s, 4H), 4.93 (sept., J=6.0 Hz, 1H), 6.87 (d, J=7.2 Hz, 1H), 7.05 (s, 4H), 7.32 (d, J=11.9 Hz, 1H), 7.42-7.57 (m, 3H), 7.77 (dd, J=12.3 and 7.2 Hz, 2H), 7.94-8.08 (m, 1H), 16.43 (s, 1H); $^{31}$P NMR (CDCl$_3$, 161.8 MHz): δ (ppm) 30.79.

Example 2

Synthesis of 1,3-bis(2,4,6-trimethylphenyl)-4,5-dihydroimidazol-2-ylidene[2-(i-propoxy)-5-(N,N-dimethylamino-ethylphosphite)phenyl]methyleneruthenium (II) dichloride C5

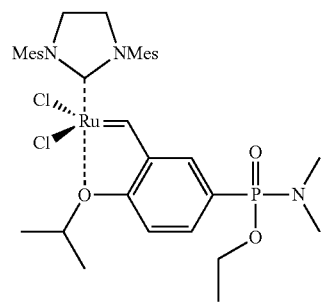

Ruthenium complex C5 were prepared as shown in Scheme 3.

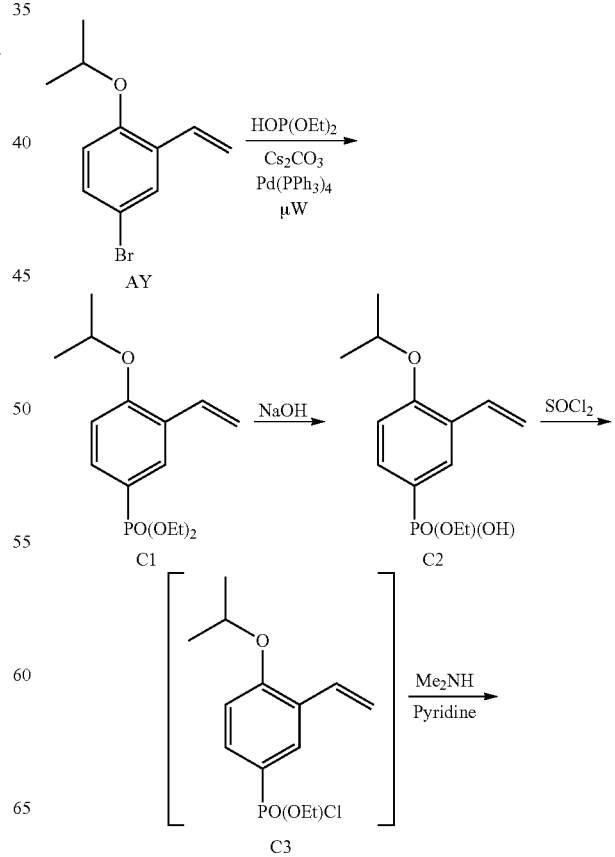

-continued

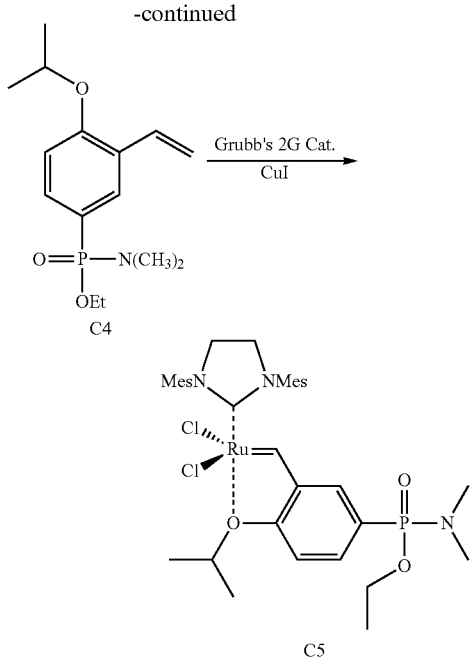

Step A: Preparation of (4-isopropoxy-3-vinyl-phenyl) phosphonic acid diethyl ester C1. A mixture of compound AY (928 mg, 1.1 eq.), diethyl phosphite (450 µl, 1 eq), cesium carbonate (1.37 g, 1.2 eq), and tetrakis triphenylphosphine palladium (0) (202 mg, 0.05 eq) in anhydrous THF (15 mL) was stirred under microwave irradiations at 120° C. for 15 min. The reaction mixture was then filtered, washed with DCM, and concentrated under reduced pressure. The crude material was purified by chromatography on silica gel (PE/EA) to afford compound C1 (835 mg) as a translucid oil in 80% yield. $^1$H NMR (CDCl$_3$, 400 MHz) δ (ppm) 1.32 (t, J=7.12 Hz, 6H), 1.38 (d, J=6.00 Hz, 6H), 4.02-4.16 (m, 4H), 4.64 (m, 1H), 5.30 (dd, J=11.08 Hz and J=1.25 Hz, 1H), 5.80 (dd, J=17.66 Hz and J=1.25 Hz, 1H), 6.93 (d, J=8.75 Hz, 1H), 7.10 (dd, J=17.50 Hz and J=11.08 Hz, 1H), 7.64 (dd, J=8.75 Hz and J=2.55 Hz, 1H), 7.90 (d, J=2.55 Hz, 1H); $^{31}$P NMR (CDCl$_3$, 161.8 MHz) δ (ppm) 19.93 (s, 1P).

Step B: Preparation of (4-isopropoxy-3-vinyl-phenyl) phosphonic acid ethyl ester C2. A solution of compound C1 (1.8 g, 1 eq.) in EtOH (35 mL) and aqueous NaOH (2N, 32 mL, 12 eq.) was stirred at 80° C. for 2 hrs. The reaction mixture was then concentrated, acidified with 1N HCl to pH 1, extracted with DCM, dried over Na$_2$SO$_4$, filtered, and concentrated under reduced pressure to afford compound C2 (1.53 g) as a translucid oil in 95% yield. $^1$H NMR (CDCl$_3$, 400 MHz) δ (ppm) 1.32 (t, J=7.12 Hz, 3H), 1.38 (d, J=6.00 Hz, 6H), 4.02-4.16 (m, 2H), 4.64 (m, 1H), 5.30 (dd, J=11.08 Hz and J=1.25 Hz, 1H), 5.80 (dd, J=17.66 Hz and J=1.25 Hz, 1H), 6.93 (d, J=8.75 Hz, 1H), 7.10 (dd, J=17.50 Hz and J=11.08 Hz, 1H), 7.64 (dd, J=8.75 Hz and J=2.55 Hz, 1H), 7.90 (d, J=2.55 Hz, 1H); $^{31}$P NMR (CDCl$_3$, 161.8 MHz) δ (ppm) 24.90 (s, 1P).

Step C: Preparation of (4-isopropoxy-3-vinyl-phenyl)dimethyl-phosphoramidate ethyl ester C4. To a stirred solution of compound C2 (133 mg, 1 eq.) in DCM (2 mL) with a few drops of DMF was added SOCl$_2$ (100 µL, 2.8 eq.) dropwise under nitrogen. The reaction mixture was allowed to stir at room temperature for 2 hrs and then concentrated under reduced pressure. The resulting residue was dissolved in pyridine (2 mL) and added to a solution of dimethylamine (2M, 0.75 mL) in THF. The mixture was stirred at room temperature for 16 hrs and then quenched with water. The reaction mixture was acidified with 1N HCl to pH 7, and then extracted with EtOAc. Organics were dried over Na$_2$SO$_4$, filtered, and purified by chromatography on silica gel (PE/EA) to afford compound C4 (407 mg) as a white solid in 69% yield. $^1$H NMR (CDCl$_3$, 400 MHz) δ (ppm) 1.36 (s, 3H), 1.37 (t, J=7.15 Hz, 3H), 1.38 (s, 3H), 2.67 (s, 3H), 2.70 (s, 3H), 4.10 (m, 2H), 4.62 (m, 1H), 5.30 (dd, J=11.16 Hz and J=1.50 Hz, 1H), 5.80 (dd, J=17.80 Hz and J=1.50 Hz, 1H), 6.90 (dd, J=8.5 Hz and J=3.2 Hz, 1H), 7.10 (dd, J=17.80 Hz and J=11.20 Hz, 1H), 7.55 (m, 1H), 7.80 (dd, J=12.90 Hz and J=2.00 Hz, 1H); $^{31}$P NMR (CDCl$_3$, 161.8 MHz) δ (ppm) 25.12 (s, 1P).

Step D: Preparation of 1,3-bis(2,4,6-trimethylphenyl)-4,5-dihydroimidazol-2-ylidene[2-(i-propoxy)-5-(N,N-dimethylamino-ethylphosphite)phenyl]methyleneruthenium (II) dichloride C5. Grubbs' second generation catalyst (226 mg, 1 eq) and copper (I) chloride (26 mg, 1 eq) were charged in a Schlenk tube and degassed. A degassed solution of compound C4 (26 mg, 21 eq.) in anhydrous dichloromethane (50 mL) was transferred via cannula to the solid. The mixture was heated at 30° C. for 60 min. The solvent was removed in vacuo and the residue was purified by chromatography on silica gel (PE/EA) to afford compound C5 (202 mg) as a green solid in 100% yield. $^{31}$P NMR (CDCl$_3$, 161.8 MHz) δ (ppm) 22.88 (s, 1P); HRMS (ES+): m/z=764 (M+H$^+$).

Example 3

Synthesis of 1,3-bis(2,4,6-trimethylphenyl)-4,5-dihydroimidazol-2-ylidene[2-(i-propoxy)-5-((4-methoxy-phenyl)-ethylphosphite)phenyl]methyleneruthenium (II) dichloride D4

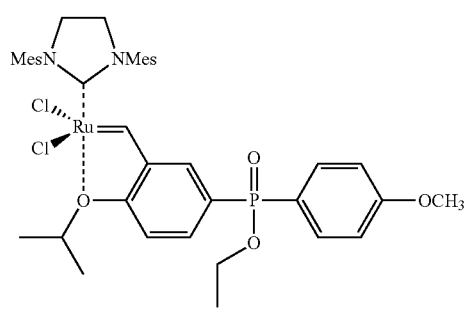

Ruthenium complex D4 were prepared as shown in Scheme 4.

Scheme 4

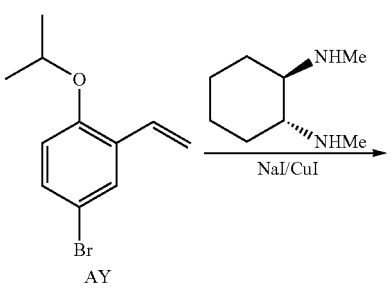

-continued

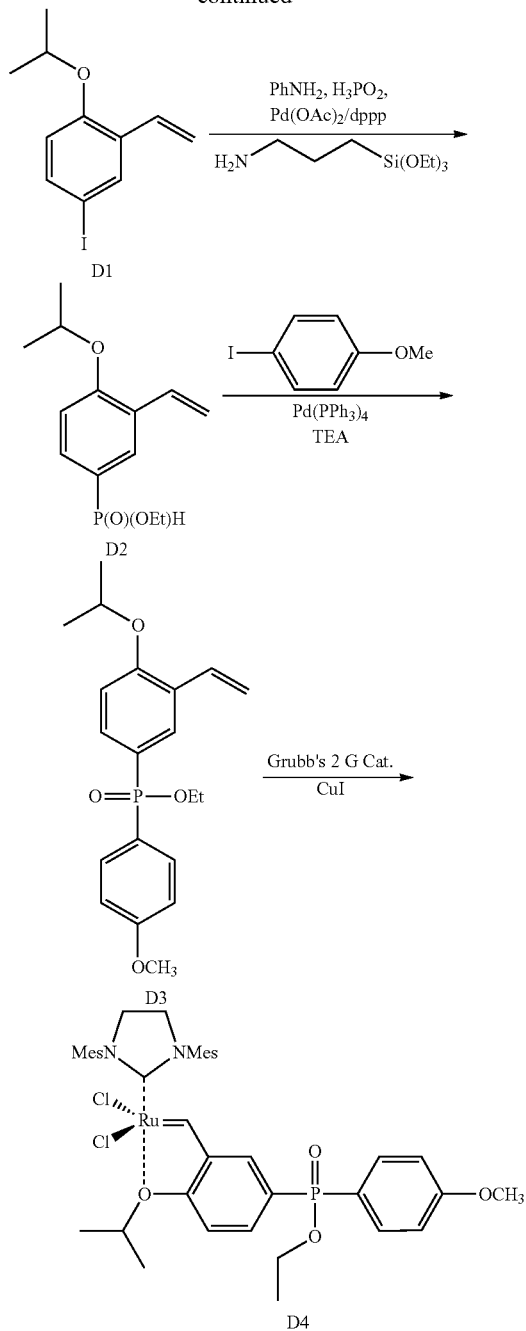

Step A: Preparation of 4-iodo-1-isopropoxy-2-vinyl-benzene D1. A mixture of compound AY (2.56 g, 1 eq.), sodium iodide (3.18 g, 2 eq.), copper iodide (100 mg, 0.05 eq.), and N,N'-dimethylcyclohexene-1,2-diamine (170 μL, 0.1 eq.) in dioxane (10 mL) was refluxed under nitrogen for 16 hrs. Aqueous NH$_3$ solution (20%, 100 mL) was added. The mixture was then poured into H$_2$O. Organics were separated, concentrated under reduced pressure, and purified by chromatography on silica gel (PE/EA) to afford compound D1 (1.83 g) as a yellow oil in 60% yield. $^1$H NMR (CDCl$_3$, 400 MHz) δ (ppm) 1.33 (s, 3H), 1.35 (s, 3H), 4.50 (m, 1H), 5.30 (dd, J=11.15 Hz, J=1.30 Hz, 1H), 6.70 (dd, J=17.80 Hz, J=1.30 Hz, 1H), 6.65 (d, J=8.80 Hz, 1H), 6.90-6.97 (dd, J=17.80 Hz, J=11.20 Hz, 1H), 7.47 (dd, J=8.80 Hz, J=2.20 Hz, 1H), 7.75 (d, J=2.20 Hz, 1H).

Step B: Preparation of (4-isopropoxy-3-vinyl-phenyl)-phosphinic acid ethyl ester D2. A mixture of compound D1 (4.85 g, 1 eq.), anilinium hypophosphite (3.21 g, 1.2 eq.), (3-aminopropyl)triethoxysilane (4.75 ml, 1.2 eq.), palladium acetate (75 mg, 0.02 eq.), and 1,3-bis(diphenylphosphino)propane (139 mg, 0.02 eq.) in acetonitrile (200 mL) was refluxed for 16 hrs. The reaction mixture was filtered, concentrated under reduced pressure, and purified by chromatography on silica gel (PE/EA) to afford compound D2 (1.97 g) as a yellow oil in 46% yield. $^1$H NMR (CDCl$_3$, 400 MHz) δ (ppm) 1.33 (s, 3H), 1.35 (s, 3H), 4.50 (m, 1H), 4.15 (m, 3H), 5.30 (dd, J=11.15 Hz, J=1.30 Hz, 1H), 6.70 (dd, J=17.80 Hz, J=1.30 Hz, 1H), 6.65 (d, J=8.80 Hz, 1H), 6.80 (m, 2H), 6.90-6.97 (dd, J=17.80 Hz, J=11.20 Hz, 1H), 7.47 (dd, J=8.80 Hz, J=2.20 Hz, 1H), 7.75 (d, J=2.20 Hz, 1H), 8.27 (s, 1H); $^{31}$P NMR (CDCl$_3$, 161.8 MHz) δ (ppm) 24.90 (s, 1P).

Step C: Preparation of (4-isopropoxy-3-vinyl-phenyl)-(4-methoxy-phenyl) phosphinic acid ethyl ester D3. A mixture of compound D2 (650 mg, 1 eq.), 4-iodoanisole (778 mg, 1.3 eq.), TEA (1.08 mL, 3 eq.), and Pd(PPh$_3$)$_4$ (295 mg, 0.1 eq.) in toluene (6.4 mL) was stirred at 110° C. for 16 hrs under nitrogen. The reaction mixture was filtered through a celite pad, washed with DCM, concentrated under reduced pressure, and purified by chromatography on silica gel (PE/EA) to afford compound D3 (1.97 g) as an orange oil in 58% yield. $^1$H NMR (CDCl$_3$, 400 MHz) δ (ppm) 1.33 (s, 3H), 1.35 (s, 3H), 3.84 (s, 3H), 4.50 (m, 1H), 4.15 (m, 3H), 5.30 (dd, J=11.15 Hz and J=1.30 Hz, 1H), 6.70 (dd, J=17.80 Hz and J=1.30 Hz, 1H), 6.65 (d, J=8.80 Hz, 1H), 6.80 (m, 2H), 6.90-6.97 (dd, J=17.80 Hz and J=11.20 Hz, 1H), 7.47 (dd, J=8.80 Hz and J=2.20 Hz, 1H), 7.75 (d, J=2.20 Hz, 1H), 7.80 (m, 4H); $^{31}$P NMR (CDCl$_3$, 161.8 MHz) δ (ppm) 32.71 (s, 1P).

Step D: Preparation of 1,3-bis(2,4,6-trimethylphenyl)-4,5-dihydroimidazol-2-ylidene[2-(i-propoxy)-5-((4-methoxy-phenyl)-ethylphosphite)phenyl]methyleneruthenium (II) dichloride D4. Compound D4 was synthesized from compound D4 as a dark solid in 35% yield according to the procedure as described for compound CS. $^{31}$P NMR (CDCl$_3$, 161.8 MHz) δ (ppm) 30.52 (s, 1P); HRMS (ES+): m/z=827 (M+H$^+$).

Example 4

Synthesis of 1,3-bis(2,4,6-trimethylphenyl)-4,5-dihydroimidazol-2-ylidene[2-(i-propoxy)-5-(phenyl-ethylphosphoramidate)phenyl]methyleneruthenium (II) dichloride E6

E6

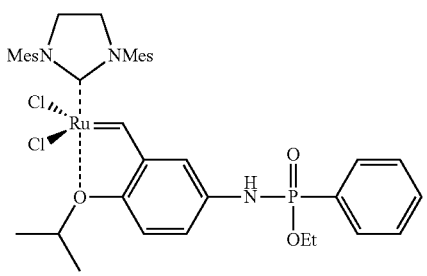

Ruthenium complex E6 were prepared as shown in Scheme 5.

Step A: Preparation of 2-isopropoxy-5-nitro-benzaldehyde E1. Compound E1 was synthesized from 2-hydroxy-5-nitrobenzaldehyde as a yellow solid in 39% yield according to the procedure as described for compound AX. $^1$H NMR (CDCl$_3$, 400 MHz) δ (ppm) 1.47 (s, 3H), 1.49 (s, 3H), 4.84 (m, 1H), 7.09 (d, J=9.20 Hz, 1H), 8.40 (dd, J=9.33 Hz and J=2.93 Hz, 1H), 8.70 (d, J=3.04 Hz, 1H), 10.46 (s, 1H).

Step B: Preparation of 1-isopropoxy-4-nitro-2-vinylbenzene E2. Compound E2 was synthesized from compound E1 as a yellow oil in 63% yield according to the procedure as described for compound AY. $^1$H NMR (CDCl$_3$, 400 MHz) δ (ppm) 1.47 (s, 3H), 1.49 (s, 3H), 4.84 (m, 1H), 5.39 (dd, J=11.02 Hz and J=1.00 Hz, 1H), 5.89 (dd, J=17.70 Hz and J=1.00 Hz, 1H), 7.09 (d, J=9.20 Hz, 1H), 8.40 (dd, J=9.33 Hz and J=2.93 Hz, 1H), 8.12 (dd, J=9.22 Hz and J=2.89 Hz, 1H), 8.37 (d, J=3.04 Hz, 1H).

Step C: Preparation of 4-isopropoxy-3-phenylamine E3. To a stirred solution of compound E2 (114 mg, 1 eq.) in acetic acid (5.5 mL) was added zinc dust (360 mg, 10 eq.). The reaction mixture was stirred at room temperature for 50 min. The mixture was then filtered, concentrated under reduced pressure, and purified by chromatography on silica gel (PE/EA) to afford compound E3 (84 mg) as a yellow oil in 86% yield. $^1$H NMR (CDCl$_3$, 400 MHz) δ (ppm) 1.29 (s, 3H), 1.31 (s, 3H), 4.16 (brs, 2H), 4.34 (m, 1H), 5.23 (dd, J=11.02 Hz and J=1.00 Hz, 1H), 5.69 (dd, J=17.70 Hz and J=1.00 Hz, 1H), 6.60 (dd, J=8.50 Hz and J=2.80 Hz, 1H), 6.77 (d, J=8.50 Hz, 1H), 6.87 (d, J=3.10 Hz, 1H), 7.01 (dd, J=17.80 Hz and J=11.20 Hz, 1H).

Scheme 5

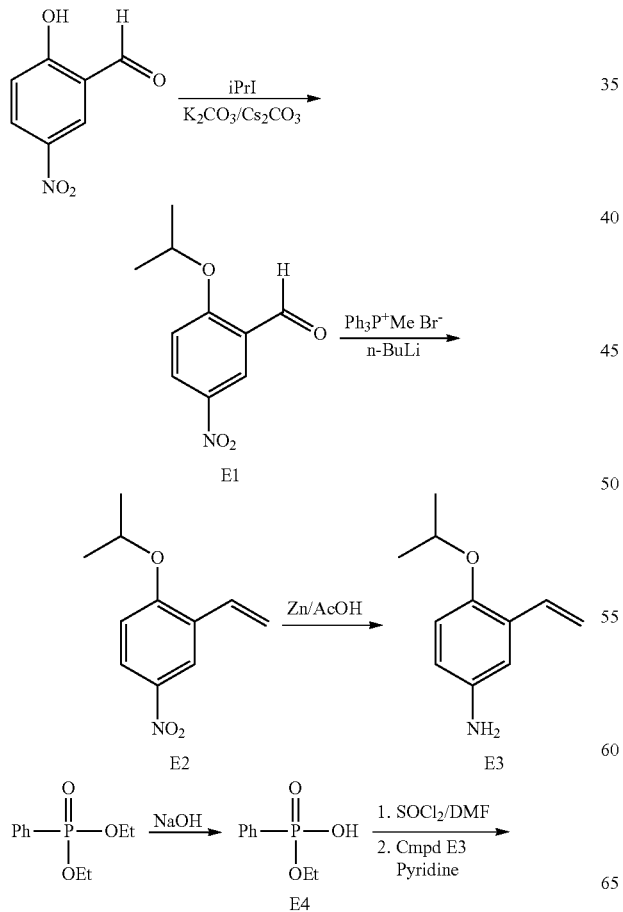

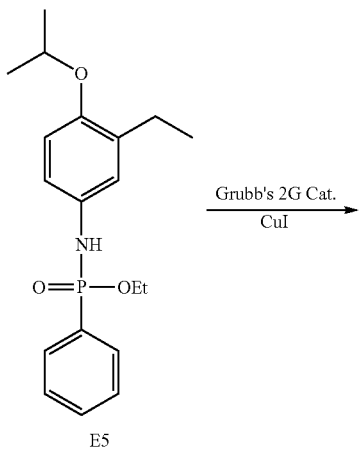

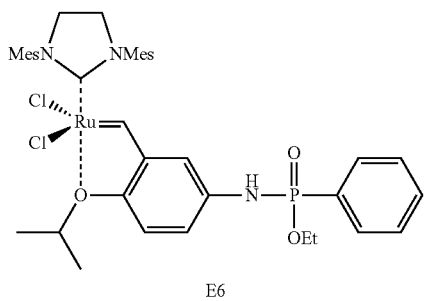

Step D: Preparation of phenyl phosphinic acid ethyl ester E4. Phenyl diethylphosphonate (2.05 g, 1 eq.) was stirred in aqueous NaOH solution (2N, 55 mL, 12 eq.) and EtOH (55 mL, 12 eq.) at 80° C. for 3 hrs. The reaction mixture was then concentrated, acidified to pH 1 with 1N HCl, extracted with DCM, and concentrated under reduced pressure to afford compound E4 as a transparent oil in 90% yield. $^1$H NMR (CDCl$_3$, 400 MHz) δ (ppm) 1.30 (t, J=7.17 Hz, 3H), 4.08 (q, J=7.17 Hz, 2H), 7.43 (m, 2H), 7.53 (t, J=7.22 Hz, 1H), 7.81 (m, 2H), 11.3 (brs, 1H); $^{31}$P NMR (CDCl$_3$, 161.8 MHz) δ (ppm) 20.96 (s, 1P).

Step E: Preparation of N-(phenyl-phosphinic acid ethyl ester)-4-isopropoxy-3-vinyl-aniline E5. Compound E5 was synthesized from compounds E3 and E4 as a yellow oil in 53% yield according to the procedure as described for compound C4. $^1$H NMR (CDCl$_3$, 400 MHz) δ (ppm) 1.26 (s, 3H), 1.28 (s, 3H), 1.34 (t, J=7.17 Hz, 3H), 4.08 (q, J=7.17 Hz, 2H), 4.30 (m, 1H), 5.12 (m, 2H), 5.60 (d, J=17.20 Hz, 1H), 6.70 (d, J=8.80 Hz, 1H), 6.70 (dd, J=8.80 Hz and J=2.80 Hz, 1H), 6.95 (dd, J=17.20 Hz and J=11.09 Hz, 1H), 7.10 (d, J=2.80 Hz, 1H), 7.43 (m, 2H), 7.52 (m, 1H), 7.80 (dd, J=13.15 Hz and J=7.20 Hz, 1H); $^{31}$P NMR (CDCl$_3$, 161.8 MHz) δ (ppm) 17.05 (s, 1P).

Step F: Preparation of 1,3-bis(2,4,6-trimethylphenyl)-4,5-dihydroimidazol-2-ylidene[2-(i-propoxy)-5-(phenyl-ethylphosphoramidate)phenyl]methyleneruthenium (II) dichloride E6. Compound E6 was synthesized from compound E5 as a green solid in 74% yield according to the procedure as described for compound C5. $^{31}$P NMR (CDCl$_3$, 161.8 MHz) δ (ppm) 17.01 (s, 1P); HRMS (ES+): m/z=811 (M+H$^+$).

Example 5

Synthesis of 1,3-bis(2-methylphenyl)-4,5-dihydroimidazol-2-ylidene[2-(i-propoxy)-5-(phenyl-ethylphosphite)phenyl]methyleneruthenium (II) dichloride G2

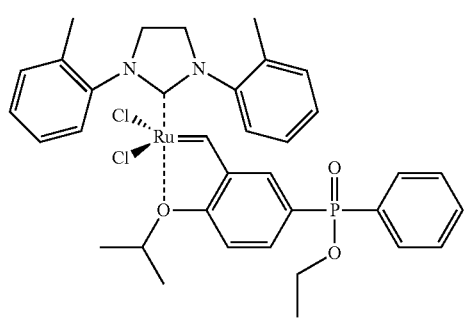

G2

Ruthenium complex G2 was prepared as shown in Scheme 6.

Preparation of 1,3-bis(2,4,6-trimethylphenyl)-4,5-dihydroimidazol-2-ylidene[2-(i-propoxy)-5-(phenyl-ethylphosphite)phenyl]methyleneruthenium (II) dichloride G2. Compound G2 was synthesized from compounds BA4 and G1 as a dark solid in 33% yield according to the procedure as described for compound C5. $^{31}$P NMR (CDCl$_3$, 161.8 MHz) δ (ppm) 30.86 (s, 1P); HRMS (ES+): m/z=740 (M+H$^+$).

Scheme 6

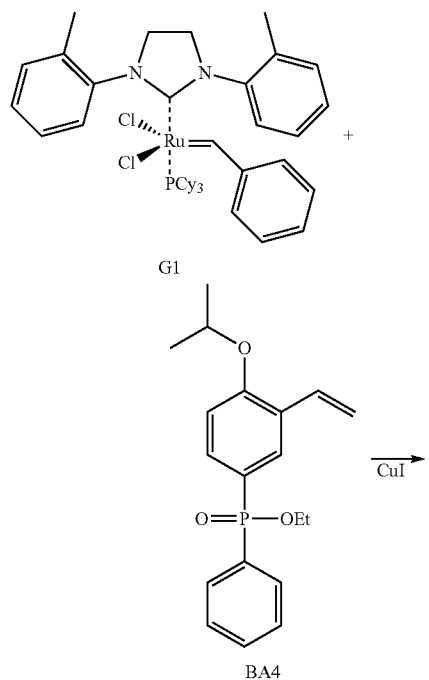

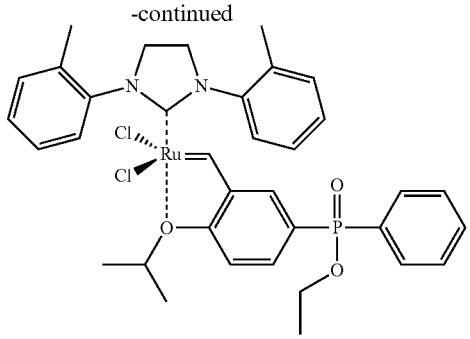

G2

Example 6

Ring Closure Metathesis

Catalytic activity of Ru catalysts AP, AQ, AR, AT, C5, D4, E6, and G2 was evaluated using seven olefin substrates as shown in Schemes 7 and 8, along with five other Ru catalysts, AO, AS, AU, AV, and AW, as shown in Scheme 9.

Scheme 7

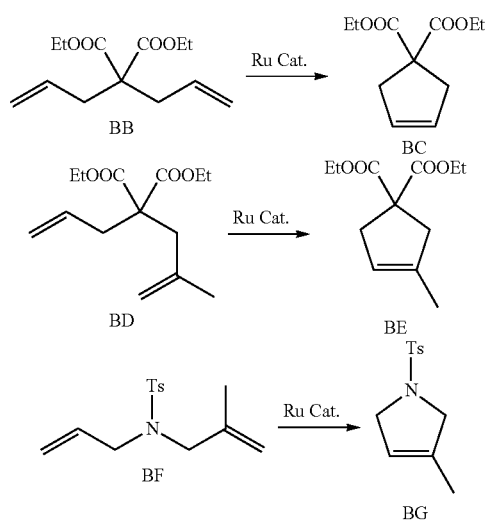

Scheme 8

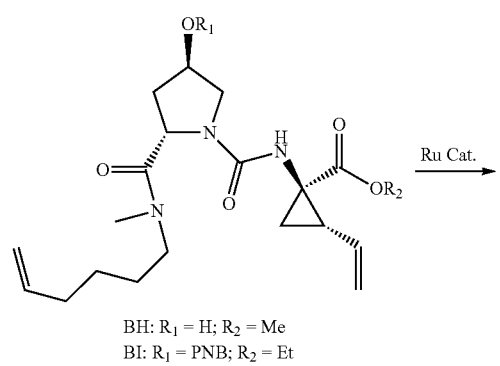

BH: R$_1$ = H; R$_2$ = Me
BI: R$_1$ = PNB; R$_2$ = Et

-continued
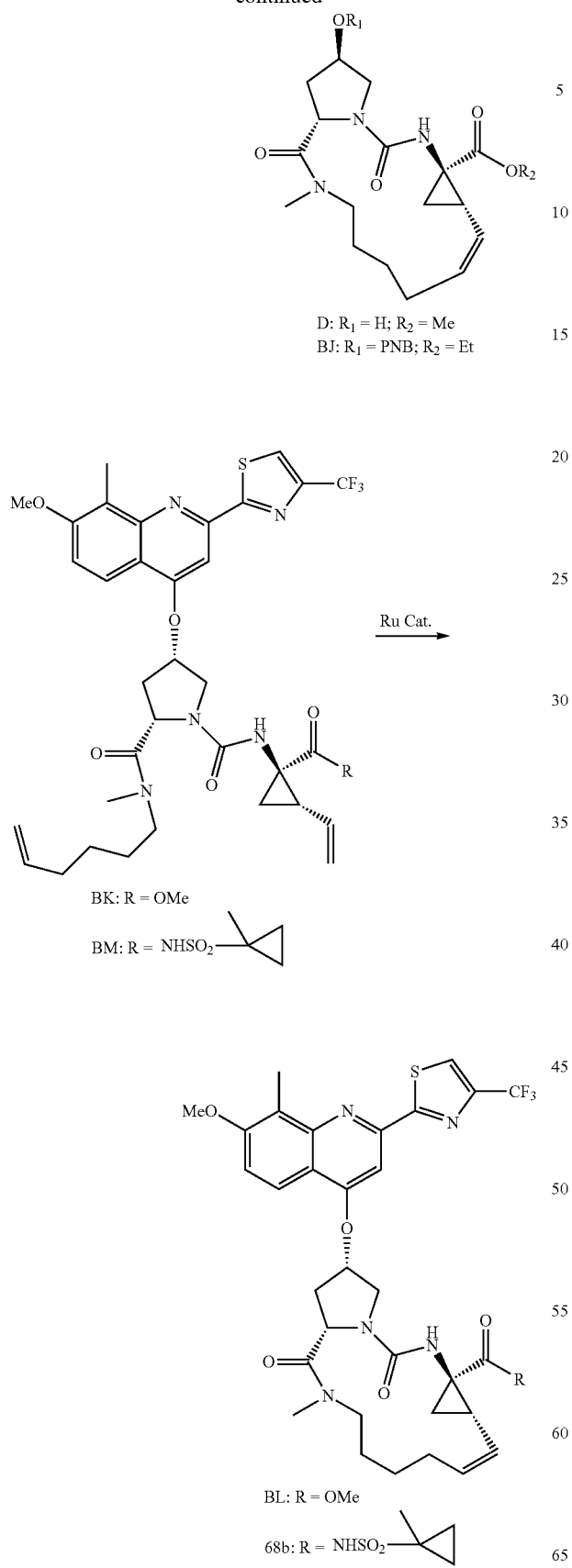
D: R₁ = H; R₂ = Me
BJ: R₁ = PNB; R₂ = Et
BK: R = OMe
BM: R = NHSO₂—⌬
BL: R = OMe
68b: R = NHSO₂—⌬
Scheme 9
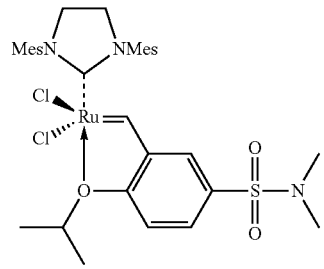
AO
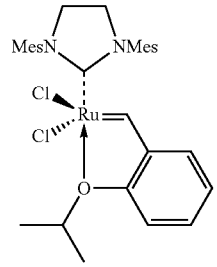
AS
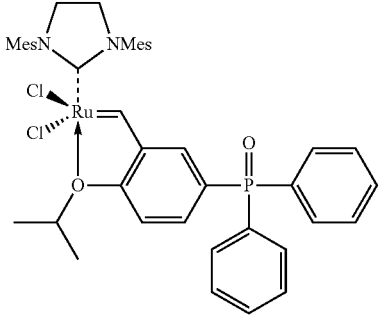
AU
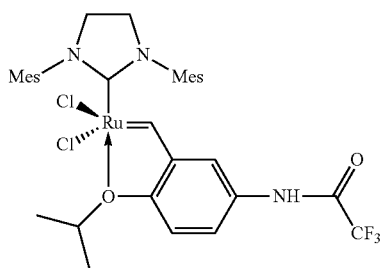
AV
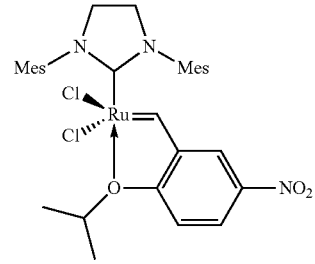
AW
A. Synthesis of Substrates
a. Syntheses of Compounds BB, BD, and BF
Compound BB is a commercially available product. Compounds BD and BF were prepared according to Kotora et al., *J. Am. Chem. Soc.*, 2004, 126:10222-10223; and Zhang et al., *J. Am. Chem. Soc.*, 2004, 126:74-75.

b. Syntheses of Compounds BH and BI

Compound BI was synthesized according to Scheme 10.

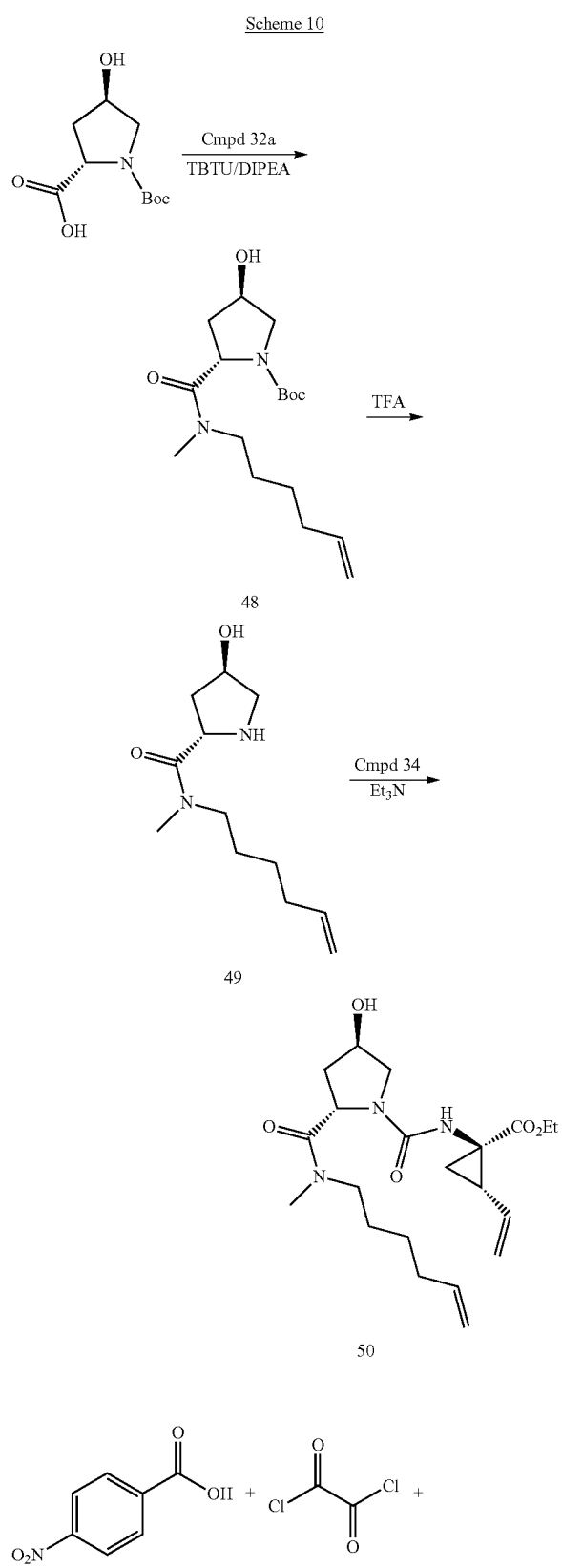

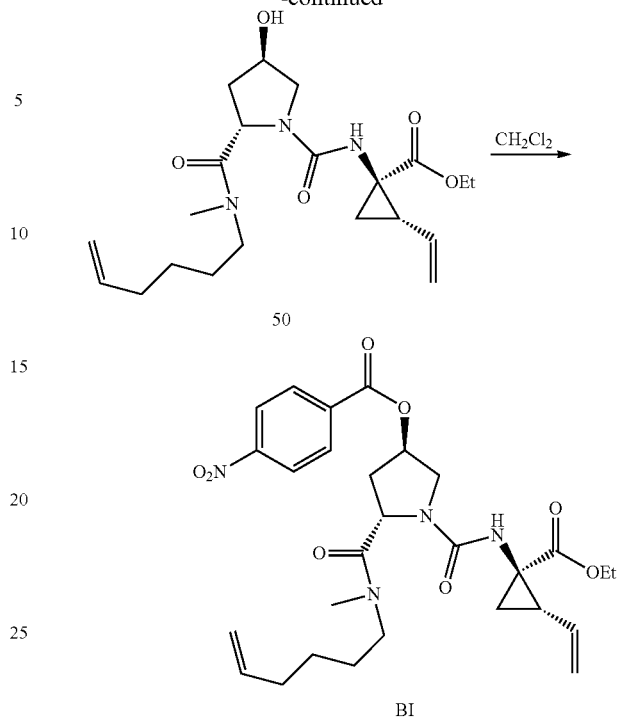

Step A: Preparation of (2S,4R)-tert-butyl 2-(N-(hex-5-enyl)-N-methyl-carbamoyl)-4-hydroxypyrrolidine-1-carboxylate 48. To a cold solution of cis-N-Boc-4-hydroxy-L-proline (10 g, 1 eq.), O-(benzotriazol-1-yl)-N,N,N',N'-tetramethyluronium tetrafluoroborate (TBTU 15.5 g, 1.12 eq.) and N-methylhex-5-en-1-amine tosylate salt 32a (13.6 g, 1.1 eq.), which was prepared according to Scheme 13 as described herein, in DMF (80 mL) containing DIPEA (29.4 mL, 3.9 eq.) was added dropwise under nitrogen at 0° C. The reaction mixture was stirred overnight at room temperature, and then quenched with water and extracted with diethyl ether. The organic layer was washed with brine, dried over magnesium sulfate, and concentrated under reduced pressure. The residue was purified by chromatography on silica gel to yield compound 48 as a rose powder in 95% yield. $^1$H NMR (DMSO-d$_6$, 400 MHz): δ (ppm) 1.29-1.3 (m, 9H), 1.33-1.55 (m, 4H), 1.70-1.80 (m, 1H), 1.97-2.12 (m, 3H), 2.77-2.97 (m, 3H), 3.15-3.40 (m, 4H), 4.22 (br s, 1H), 4.50-4.62 (m, 1H), 4.90-5.04 (m, 3H), 5.71-5.83 (m, 1H); MS (ESI$^+$): m/z=327 (MH$^+$).

Step B: Preparation of (2S,4R)—N-(hex-5-enyl)-4-hydroxy-N-methyl-pyrrolidine-2-carboxamide 49. Trifluoroacetic acid was added dropwise to a solution of compound 48 (1 g, 1 eq.) in DCM (10 mL). The reaction mixture was stirred for 3 hrs at room temperature, and then trifluoroacetic acid was removed under reduced pressure. The residue was co-evaporated with toluene to yield compound 49 as pale yellow oil in quantitative yield. MS (ESI$^+$): m/z=227 (MIT).

Step C: Preparation of (1R)-1-{[2(S)-(hex-5-enyl-methyl-carbamoyl)-4(R)-hydroxy-pyrrolidine-N-carbonyl]amino}-2(R)-vinyl-cyclopropanecarboxylic acid ethyl ester 50. Triethylamine (1.3 mL, 3 eq.) was added at room temperature under nitrogen to a mixture of 1-((1R,2S)-1-(ethoxycarbonyl)-2-vinylcyclopropyl-carbamoyl)-3-methyl-1H-imidazol-3-ium iodide 34 (0.7 g, 1 eq.) and compound 49 (1.2 g, 1 eq.) in DCM (15 mL). The reaction mixture was stirred overnight at room temperature and then quenched with 1M aqueous hydrochloric acid. The organic layer was dried over sodium sulfate and concentrated under reduced pressure. The residue was purified by chromatography on silica gel to yield compound 50 as a white solid in 70% yield. $^1$H NMR (DMSO-d$_6$, 400 MHz): δ (ppm) 1.10-1.14 (td, J=7.07 and 2.01 Hz, 3H), 1.15-1.17 (m, 1H), 1.22-1.30 (m, 1H), 1.33-1.41 (m, 2H), 1.42-1.50 (m, 1H), 1.54-1.57 (m, 1H), 1.71-1.79 (m, 1H), 1.97-2.07 (m, 4H), 2.74 (s, 1H), 2.97 (s, 2H), 3.11 (d, J=10.24 Hz, 1H), 3.15-3.21 (m, 1H), 3.43-3.48 (m, 1H), 3.91-4.07 (m, 2H), 4.29-4.30 (m, 1H), 4.65-4.69 (d, J=6.50 Hz, 1H), 4.90-4.96 (m, 3H), 5.00-5.06 (m, 2H), 5.19-5.25 (dd, J=17.04 and 6.50 Hz, 1H), 5.51-5.61 (m, 1H), 5.71-5.83 (m, 1H), 7.08 (s, 1H); MS (ESI$^-$): m/z=406 (MH$^-$).

Step D: Preparation of (3R,5S)-1-((1R,2S)-1-(ethoxycarbonyl)-2-vinyl-cyclopropylcarbamoyl)-5-(hex-5-enyl(methyl)carbamoyl)pyrrolidin-3-yl-4-nitrobenzoate BI. To a solution of 4-nitrobenzoic acid (3.1 g, 1.5 eq) in CH$_2$Cl$_2$ (61 mL) were added dropwise 3.1 mL oxalyl chloride (3 eq), followed by 60 μL DMF. The reaction mixture was stirred at room temperature for 2 hrs and concentrated in vacuo. A solution of the resulting solid in CH$_2$Cl$_2$ (30 mL) was added dropwise to a solution of compound 50 (5.0 g, 1 eq) and triethylamine (3.4 mL, 2 eq) in CH$_2$Cl$_2$ (30 mL). The reaction mixture was stirred at room temperature for 2 hrs, and then washed with water and a saturated aqueous solution of sodium carbonate. The aqueous layer was extracted with CH$_2$Cl$_2$. The combined organic phases were dried on sodium sulphate, filtered, and concentrated to dryness. Recrystallisation with TBME gave compound BI as a yellow powder, and the filtrate was submitted to flash chromatography using CH$_2$Cl$_2$/MeOH as an eluant, affording a total of 6.42 g of compound BI in 93% yield. $^1$H NMR (CDCl$_3$, 400 MHz) δ (ppm) 1.23 (m, 3H), 1.36-1.61 (m, MI), 1.69 (m, 1H), 1.86 (td, J=5.1 and 7.8 Hz, 1H), 2.05-2.19 (m, 3H), 2.35-2.50 (m, 2H), 2.95 and 3.15 (2s, rotamers, 3H), 3.21 and 3.80 (2m, rotamers, 1H), 3.38 (m, 1H), 3.61 (m, 1H), 4.09 (m, 2H), 4.21 (m, 1H), 4.94-5.00 (m, 1H), 5.05 (br d, 10.3 Hz, 2H), 5.10 (dd, J=1.30 and 10.2 Hz, 1H), 5.27 (d, J=17.0 Hz, 1H), 5.68-5.84 (m, 3H), 8.20 (d, J=8.8 Hz, 2H), 8.31 (d, J=8.8 Hz, 2H).

Compound BH (white powder) was synthesized using the same procedure as compound 50. $^1$H NMR (CDCl$_3$, 400 MHz) δ 1.34-1.46 (m, 2H), 1.49-1.57 (m, 3H), 1.70 (s, 2H), 1.86 (td, J=8.0 and 5.4 Hz, 1H), 2.03-2.28 (m, 6H), 2.92 and 3.11 (2s, rotamers, 3H), 3.27-3.44 (m, 2H), 3.69 (s, 3H), 3.79 (m, J=5.1 and 4.5 Hz, 1H), 4.71 (br s, 1H), 4.90-4.97 (m, 1H), 4.97-5.05 (m, 1H), 5.09 (dd, J=10.3 and 1.5 Hz, 1H), 5.20 (br s, 1H), 5.27 (dd, J=17.1 and 1.0 Hz, 1H), 5.67-5.85 (m, 2H).

c. Syntheses of Compounds BK and BM

Compounds BK and BM were prepared according to Scheme 11.

Step A: Preparation of (2S,4S)-1-tert-butyl 2-methyl 4-(7-methoxy-8-methyl-2-(4-(trifluoromethyl)thiazol-2-yl)quinolin-4-yloxy)pyrrolidine-1,2-dicarboxylate BQ. The 7-methoxy-8-methyl-2-(4-(trifluoromethyl)thiazol-2-yl)quinolin-4-ol BO (10.0 g, 1 eq.), the N-Boc-trans-4-hydroxyproline methyl ester BP (7.20 g, 1 eq.), and the triphenylphosphine (11.56 g, 1.5 eq.) in suspension in THF (250 mL) under N$_2$ were cooled down to 0° C. The DIAD (8.70 mL, 1.5 eq.) was added dropwise. The reaction mixture was allowed to warm up and stir at room temperature for 1.25 hrs, then cooled again at 0° C. and additional 1 more eq. of DIAD was added. The reaction mixture was stirred for 2 hrs at room temperature, and then concentrated in vacuo to 50 mL. Water and ethyl acetate were added and the phases were separated. The aqueous layer was further extracted with ethyl acetate. The organic layer was washed with brine, dried over magnesium sulfate, and concentrated under reduced pressure. The residue was purified by chromatography on silica gel to yield compound BQ (16.75 g, 87% purity). MS (ESI, EI$^+$) m/z=568.3 (MH$^+$); 626.5 (M+OAc$^-$).

Scheme 11

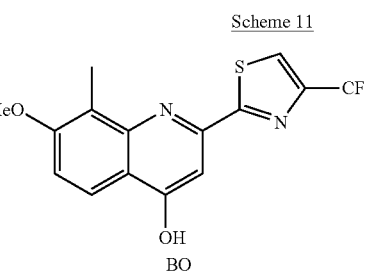

BO

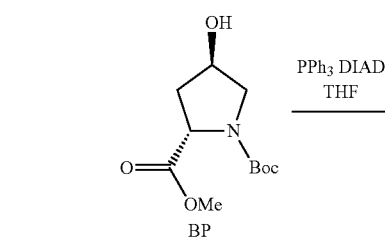

BP

PPh$_3$ DIAD
THF

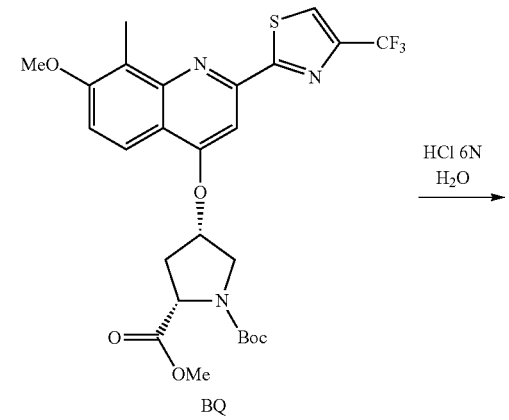

BQ

HCl 6N
H$_2$O

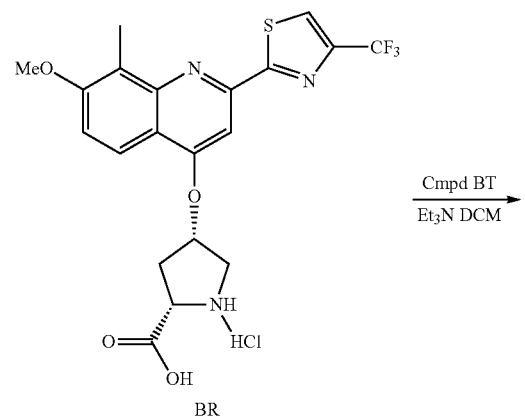

BR

Cmpd BT
Et$_3$N DCM

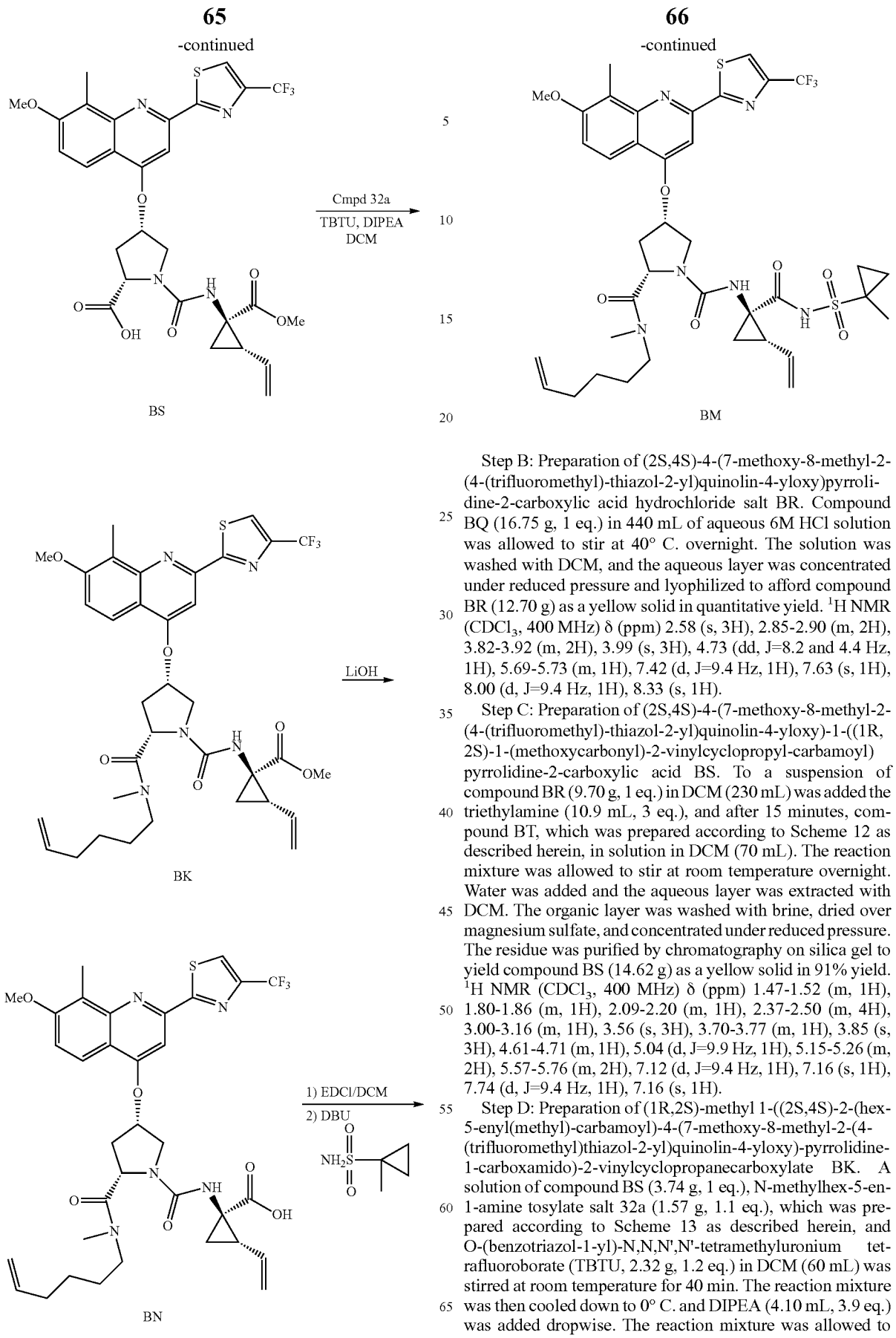

Step B: Preparation of (2S,4S)-4-(7-methoxy-8-methyl-2-(4-(trifluoromethyl)-thiazol-2-yl)quinolin-4-yloxy)pyrrolidine-2-carboxylic acid hydrochloride salt BR. Compound BQ (16.75 g, 1 eq.) in 440 mL of aqueous 6M HCl solution was allowed to stir at 40° C. overnight. The solution was washed with DCM, and the aqueous layer was concentrated under reduced pressure and lyophilized to afford compound BR (12.70 g) as a yellow solid in quantitative yield. $^1$H NMR (CDCl$_3$, 400 MHz) δ (ppm) 2.58 (s, 3H), 2.85-2.90 (m, 2H), 3.82-3.92 (m, 2H), 3.99 (s, 3H), 4.73 (dd, J=8.2 and 4.4 Hz, 1H), 5.69-5.73 (m, 1H), 7.42 (d, J=9.4 Hz, 1H), 7.63 (s, 1H), 8.00 (d, J=9.4 Hz, 1H), 8.33 (s, 1H).

Step C: Preparation of (2S,4S)-4-(7-methoxy-8-methyl-2-(4-(trifluoromethyl)-thiazol-2-yl)quinolin-4-yloxy)-1-((1R,2S)-1-(methoxycarbonyl)-2-vinylcyclopropyl-carbamoyl) pyrrolidine-2-carboxylic acid BS. To a suspension of compound BR (9.70 g, 1 eq.) in DCM (230 mL) was added the triethylamine (10.9 mL, 3 eq.), and after 15 minutes, compound BT, which was prepared according to Scheme 12 as described herein, in solution in DCM (70 mL). The reaction mixture was allowed to stir at room temperature overnight. Water was added and the aqueous layer was extracted with DCM. The organic layer was washed with brine, dried over magnesium sulfate, and concentrated under reduced pressure. The residue was purified by chromatography on silica gel to yield compound BS (14.62 g) as a yellow solid in 91% yield. $^1$H NMR (CDCl$_3$, 400 MHz) δ (ppm) 1.47-1.52 (m, 1H), 1.80-1.86 (m, 1H), 2.09-2.20 (m, 1H), 2.37-2.50 (m, 4H), 3.00-3.16 (m, 1H), 3.56 (s, 3H), 3.70-3.77 (m, 1H), 3.85 (s, 3H), 4.61-4.71 (m, 1H), 5.04 (d, J=9.9 Hz, 1H), 5.15-5.26 (m, 2H), 5.57-5.76 (m, 2H), 7.12 (d, J=9.4 Hz, 1H), 7.16 (s, 1H), 7.74 (d, J=9.4 Hz, 1H), 7.16 (s, 1H).

Step D: Preparation of (1R,2S)-methyl 1-((2S,4S)-2-(hex-5-enyl(methyl)-carbamoyl)-4-(7-methoxy-8-methyl-2-(4-(trifluoromethyl)thiazol-2-yl)quinolin-4-yloxy)-pyrrolidine-1-carboxamido)-2-vinylcyclopropanecarboxylate BK. A solution of compound BS (3.74 g, 1 eq.), N-methylhex-5-en-1-amine tosylate salt 32a (1.57 g, 1.1 eq.), which was prepared according to Scheme 13 as described herein, and O-(benzotriazol-1-yl)-N,N,N',N'-tetramethyluronium tetrafluoroborate (TBTU, 2.32 g, 1.2 eq.) in DCM (60 mL) was stirred at room temperature for 40 min. The reaction mixture was then cooled down to 0° C. and DIPEA (4.10 mL, 3.9 eq.) was added dropwise. The reaction mixture was allowed to warm up and stir at room temperature for 2 hrs. Water was added and the aqueous layer was extracted with DCM. The organic layer was washed with brine, dried over magnesium sulfate, and concentrated under reduced pressure. The residue was purified by chromatography on silica gel to yield compound BK (4.30 g) as a yellow solid in quantitative yield. $^1$H NMR (CDCl$_3$, 400 MHz) δ (ppm) 1.18-1.45 (m, 4H), 1.48-1.58 (m, 1H), 1.81-1.90 (m, 2H), 2.05 (m, J=7.6 Hz, 1H), 2.21 (se, J=7.3 Hz, 1H), 2.27-2.36 (m, 1H), 2.67 (s, 3H), 2.88 and 3.00 (2s, rotamers, 3H), 3.06-3.14 and 3.20-3.29 (2m, rotamers, 1H), 3.33-3.42 and 3.49-3.58 (2m, rotamers, 1H), 3.71 (s, 3H), 3.92 (td, J=10.1 and 3.8 Hz, 1H), 3.98 and 3.99 (2s, rotamers, 3H), 4.06-4.13 (m, 1H), 4.83-5.03 (m, 3H), 5.10 (d, J=10.5 Hz, 1H), 5.14 (dd, J=10.3 and 1.2 Hz, 1H), 5.21 (s, 1H), 5.26-5.34 (m, 1H), 5.40-5.46 (m, 1H), 5.58-5.80 (m, 2H), 7.24-7.28 (m, 1H), 7.45 (d, J=7.1 Hz, 1H), 7.86 (s, 1H), 8.05 (t, J=8.1 Hz, 1H); MS (ESI, EI$^+$) m/z=716.2 (MH$^+$).

Step E: Preparation of (1R,2S)-1-((2S,4S)-2-(hex-5-enyl(methyl)carbamoyl)-4-(7-methoxy-8-methyl-2-(4-(trifluoromethyl)thiazol-2-yl)quinolin-4-yloxy)pyrrolidine-1-carboxamido)-2-vinylcyclopropanecarboxylic acid. Compound BN (yellow solid) was synthesized in quantitative yield from compound BK (4.30 g, 1 eq) and LiOH (290 mg, 2 eq). MS (ESI, EI$^+$) m/z=702.4 (MH$^+$).

Step F: Preparation of (2S,4S)—N$^2$-(hex-5-enyl)-4-(7-methoxy-8-methyl-2-(4-(trifluoromethyl)thiazol-2-yl)quinolin-4-yloxy)-N$^2$-methyl-N$^1$-((1R,2S)-1-(1-methyl-cyclopropylsulfonylcarbamoyl)-2-vinylcyclopropyl)pyrrolidine-1,2-dicarboxamide. Compound BM (white solid) was synthesized from compound BN (4.22 g, 1 eq) and 1-methylcyclopropylsulfonamide (3.25 g, 4 eq) in 31% yield according to the following procedure: Under nitrogen, a solution of compound BN and EDCI (2 eq.) in dry dichloromethane (5 mL) was stirred at room temperature for 2 hours, 1-Methylcyclopropyl-sulfonamide (4 eq.) and DBU (2 eq.) were then added under nitrogen and the reaction mixture was stirred for additional 20 hours. Dichloromethane and water were added and the two layers separated. The organic layer was washed with water (three times) and brine, then dried over Na$_2$SO$_4$, filtered and concentrated under reduced pressure. The residue was purified by chromatography on silica gel to yield compound BM. $^1$H NMR (CDCl$_3$, 400 MHz) δ (ppm) 0.74-0.86 (m, 2H), 1.11-1.21 (m, 2H), 1.30-1.40 (m, 3H), 1.50 (s, 3H), 1.60-1.68 (m, 3H), 1.78 (q, J=6.0 Hz, 1H), 1.88-1.94 (m, 1H), 2.00-2.08 (m, 1H), 2.22 (q, J=8.7 Hz, 1H), 2.33 (dd, J=14.0 and 2.1 Hz, 1H), 2.67 (s, 3H), 2.78-2.82 (m, 1H), 2.87 and 2.97 (2s, rotamers, 3H), 3.15-3.36 (m, 1H), 3.58-3.68 (m, 1H), 3.90-4.01 (m, 5H), 4.82-4.91 (m, 1H), 4.92-5.01 (m, 2H), 5.11 (d, J=10.2 Hz, 1H), 5.25-5.35 (m, 2H), 5.46-5.51 (m, 1H), 5.54-5.76 (m, 2H), 7.25-7.30 (m, 1H), 7.46 (d, J=7.0 Hz, 1H), 7.87 (s, 1H), 8.02 (t, J=10.1 Hz, 1H); MS (ESI, EE) m/z=819.2 (MH$^+$).

d. Synthesis of Compound BT

Preparation of (1R,2S)-methyl 1-(1H-imidazole-1-carboxamido)-2-vinylcyclopropanecarboxylate BT. Compound BT was prepared according to Scheme 12. To a suspension of (1R,2S)-methyl 1-amino-2-vinylcyclopropanecarboxylate tosylate salt (25.0 g, 1 eq) in THF (150 mL) at 50° C. were added CDI (14.24 g, 1.1 eq) and TEA (12.27 mL, 1.1 eq.). The reaction mixture was then refluxed overnight. The solvent was removed under reduced pressure. The residue was dissolved in EtOAc, and washed with water. The organic layer was dried over sodium sulfate and concentrated. The residue was triturated in Et$_2$O to afford compound BT (15.24 g, purity 80%) as a white solid. $^1$H NMR (CDCl$_3$, 400 MHz) δ (ppm) 1.63 (dd, J=5.8 and 9.7 Hz, 1H), 1.96 (dd, J=5.8 and 8.4 Hz, 1H), 2.30 (q, J=8.9 Hz, 1H), 3.73 (s, 3H), 5.16 (d, J=10.0 Hz, 1H), 5.28 (d, J=17.0 Hz, 1H), 5.69-5.81 (m, 1H), 7.03 (s, 1H), 7.50 (s, 1H), 8.24 (s, 1H), 8.57 (s, 1H).

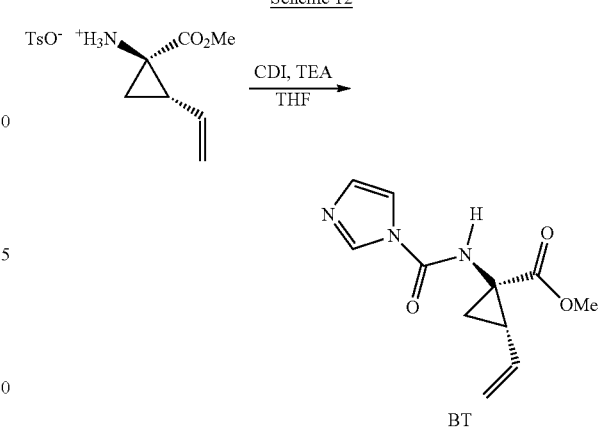

Scheme 12 e. Synthesis of Compound 32a

The synthesis of N-methyl-o-alkenyl-1-amine tosylate salt 32a is shown in Scheme 13.

Step A: Preparation of 2,2,2-trifluoro-N-(hex-5-enyl)-N-methylacetamide 31a. Sodium hydride (60% dispersion in mineral oil, 31.5 g, 1.28 eq.) was slowly added under nitrogen atmosphere to a solution of N-methyl-2,2,2-trifluoroacetamide (100 g, 1.28 eq.) in DMF (500 mL) at 0° C. The reaction mixture was stiffed for 90 min at 0° C., and then 6-bromo-1-hexene (100 g, 1 eq) was added dropwise over 45 min. The reaction mixture was allowed to warm up to room temperature, and stirred for 3 days at room temperature. The reaction mixture was then poured into water and extracted tree time with EtOAc. The combined organics layers were dried over anhydrous sodium sulphate and concentrated under reduced pressure. The residue was purified by flash chromatography on silica gel to produce compound 31a as colorless oil in 56% yield. $^1$H NMR (DMSO-d$_6$, 400 MHz) δ (ppm) 1.27-1.38 (m, 2H), 1.48-1.60 (m, 2H), 2.00-2.06 (m, 2H), 2.93-3.07 (2m, 3H), 3.35-3.40 (m, 2H), 4.92-5.04 (m, 2H), 5.73-5.83 (m, 1H).

Step B: Preparation of N-methylhex-5-en-1-amine tosylate salt 32a. At room temperature, compound 31a (71.88 g, 1 eq.) and p-toluene sulfonic acid (74.4 g, 1.2 eq.) were dissolved in MeOH (640 mL). The reaction mixture was refluxed for 7 days. The solvent was then removed under vacuum, and the residue was recrystallized in acetone. The product was isolated by filtration and dried over $P_2O_5$ to give compound 32a as a white powder in 76% yield. $^1$H NMR (CDCl$_3$, 400 MHz): δ (ppm) 1.38 (q, J=7.76 Hz, 2H), 1.71 (q, J=7.76 Hz, 2H), 1.99 (q, J=6.98 Hz, 2H), 2.38 (s, 3H), 2.70 (t, J=5.17 Hz, 3H), 2.87-2.93 (m, 4.92-4.99 (m, 2H), 5.67-5.73 (m, 1H), 7.20 (d, J=7.76 Hz, 2H), 7.75 (d, J=7.76 Hz, 2H), 8.62 (br s, 2H).

B. Ring Closure Metathesis

All reactions were performed in 1,2-dichloroethane at 0.005 M with $N_2$ bubbling through the reaction mixture. For the substrates depicted in Scheme 7, the RCM reactions were carried out on a 100-mg scale; whereas for the substrates depicted in Scheme 8, the typical scale of the reaction was 200-250 mg. The catalyst was added in solution in 0.5 mL of DCE, in the pre-heated reaction mixture. The conversion of the starting material was followed via TLC and/or HPLC. Products are isolated after flash chromatography (note: compound III was stirred with charcoal and filtered on celite prior to purification).

The experimental results of catalytic activity for the different catalysts are listed in Tables 1 to 7, respectively.

Synthesis of diethyl cyclopent-3-ene-1,1-dicarboxylate BC. $^1$H NMR (CDCl$_3$, 400 MHz): δ (ppm) 1.18 (t, J=7.2 Hz, 6H), 2.94 (s, 4H), 4.13 (q, J=7.2 Hz, 4H), 5.54 (s, 2H); MS (ESI, EE): m/z=213.0 (MH$^+$).

Synthesis of diethyl 3-methylcyclopent-3-ene-1,1-dicarboxylate BE. $^1$H NMR (CDCl$_3$, 400 MHz): δ (ppm) 1.66 (s, 3H), 2.42 (s, 3H), 3.97 (m, 2H), 4.07 (m, 2H), 5.25 (m, 1H), 7.32 (d, J=8.2 Hz, 2H), 7.72 (d, J=8.2 Hz, 2H); MS (ESI, EI$^+$): m/z=238.1 (MH$^+$).

TABLE 1

Compound BC

| Entry | Catalyst | Temperature | Catalyst loading | Isolated yield (%) | Time (hrs) |
|---|---|---|---|---|---|
| 1 | AO | 40° C. | 1.5% + 1.5% (1 hr) | 99 | 2.0 |
| 2 | AP | 40° C. | 1.5% + 1.5% (1 hr) | 87 | 2.5 |
| 3 | AQ | 40° C. | 1.5% + 1.5% (1 hr) | 87 | 2.5 |
| 4 | AR | 40° C. | 1.5% + 1.5% (1 hr) + 1% (2.2 hrs) | 93 | 3.0 |
| 5 | AS | 40° C. | 1.5% + 1.5% (1 hr) + 1% (2.2 hrs) | 91 | 3.0 |
| 6 | AT | 40° C. | 1.5% + 1.5% (1 hr) + 1% (2.2 hrs) | 82 | 3.0 |
| 7 | C5 | 40° C. | 1.5% + 1.5% (1 hr) | 94 | 2.5 |
| 8 | D4 | 40° C. | 1.5% + 1.5% (1 hr) | 93 | 2.5 |
| 9 | E6 | 40° C. | 1.5% + 1.5% (1 hr) | 85 | 2.5 |
| 10 | G2 | 40° C. | 1.5% + 1.5% (1 hr) | 71 | 2.5 |

TABLE 2

Compound BE

| Entry | Catalyst | Temperature | Catalyst loading | Isolated yield (%) | Time (hrs) |
|---|---|---|---|---|---|
| 1 | AO | 40° C. | 1.5% + 1.5% (1 hr) + 1.5% (2.5 hrs) | 99 | 4 |
| 2 | AP | 40° C. | 1.5% + 1.5% (1 hr) + 1.5% (2.5 hrs) | 91 | 4 |
| 3 | AQ | 40° C. | 1.5% + 1.5% (1 hr) + 1.5% (2.5 hrs) | 97 | 4 |
| 4 | AR | 40° C. | 1.5% + 1.5% (1 hr) + 1.5% (2.5 hrs) | 93 | 3.5 |
| 5 | AS | 40° C. | 1.5% + 1.5% (1 hr) + 1.5% (2.5 hrs) | 74 | 3.5 |
| 6 | AT | 40° C. | 1.5% + 1.5% (1 hr) + 1.5% (2.5 hrs) | 81 | 3.5 |
| 7 | C5 | 40° C. | 1.5% + 1.5% (1 hr) + 1.5% (2.5 hrs) | 99 | 3.5 |
| 8 | D4 | 40° C. | 1.5% + 1.5% (1 hr) + 1.5% (2.5 hrs) | 96 | 3.5 |
| 9 | E6 | 40° C. | 1.5% + 1.5% (1 hr) + 1.5% (2.5 hrs) | 93 | 3.5 |
| 10 | G2 | 40° C. | 1.5% + 1.5% (1 hr) + 1.5% (2.5 hrs) | 70 | 3.5 |

TABLE 3

Compound BG

| Entry | Catalyst | Temperature | Catalyst loading | Isolated yield (%) | Time (hrs) |
|---|---|---|---|---|---|
| 1 | AO | 40° C. | 1.5% + 1.5% (1 hr) | 95 | 2.5 |
| 2 | AP | 40° C. | 1.5% + 1.5% (1 hr) | 85 | 3.5 |
| 3 | AQ | 40° C. | 1.5% + 1.5% (1 hr) + 0.7% (2.5 hrs) | 85 | 3.5 |
| 4 | AR | 40° C. | 1.5% + 1.5% (1 hr) + 0.7% (2.5 hrs) | 79 | 3.5 |
| 5 | AS | 40° C. | 1.5% + 1.5% (1 hr) + 0.7% (2.5 hrs) | 93 | 3.5 |
| 6 | AT | 40° C. | 1.5% + 1.5% (1 hr) + 0.7% (2.5 hrs) | 93 | 3.5 |
| 7 | C5 | 40° C. | 1.5% + 1.5% (1 hr) + 0.7% (2.5 hrs) | 92 | 3.5 |
| 8 | D4 | 40° C. | 1.5% + 1.5% (1 hr) + 0.7% (2.5 hrs) | 92 | 3.5 |
| 9 | E6 | 40° C. | 1.5% + 1.5% (1 hr) + 0.7% (2.5 hrs) | 87 | 3.5 |
| 10 | G2 | 40° C. | 1.5% + 1.5% (1 hr) + 0.7% (2.5 hrs) | 85 | 3.5 |

Synthesis of (1aR,6R,7aS,15aS,Z)-methyl 6-hydroxy-9-methyl-3,8-dioxo-1a,2,3,5,6,7,7a,8,9,10,11,12,13,15a-tetradecahydro-1H-cyclopropa[m]pyrrolo[1,2-c][1,3,6]triazacyclotetradecine-1a-carboxylate D.

Synthesis of 3-methyl-1-tosyl-2,5-dihydro-1H-pyrrole BG. $^1$H NMR (CDCl$_3$, 400 MHz): δ (ppm) 1.66 (s, 3H), 2.42 (s, 3H), 3.97 (m, 2H), 4.07 (m, 2H), 5.25 (m, 1H), 7.32 (d, J=8.2 Hz, 2H), 7.72 (d, J=8.2 Hz, 2H); MS (ESI, EI$^+$): m/z=238.1 (MH$^+$).

TABLE 4

Compound D

| Entry | Catalyst | Temperature | Catalyst loading | Isolated yield (%) | Time (hr) |
|---|---|---|---|---|---|
| 1 | AO | 80° C. | 2% + 1% (1.5 hrs) | 51 | 2.5 |
| 2 | AP | 80° C. | 2% + 1% (1.5 hrs) | 44 | 3.0 |
| 3 | AQ | 80° C. | 2% + 1% (1.5 hrs) | 56 | 2.5 |
| 4 | AR | 80° C. | 2% + 1% (1.5 hrs) | 47 | 2.5 |
| 5 | AS | 80° C. | 2% + 1% (1.5 hrs) | 50 | 2.5 |
| 6 | AT | 80° C. | 2% + 1% (1.5 hrs) | 53 | 3.0 |
| 7 | AU | 80° C. | 2% + 1% (1.5 hrs) | 50 | 2.5 |
| 8 | C5 | 80° C. | 2% + 1% (1.5 hrs) | 52 | 3 |
| 9 | D4 | 80° C. | 2% + 1% (1.5 hrs) | 44 | 3 |
| 10 | E6 | 80° C. | 2% + 1% (1.5 hrs) | 45 | 3 |
| 11 | G2 | 80° C. | 2% + 1% (1.5 hrs) | 11 | 2.5 |

TABLE 5

Compound BJ

| Entry | Catalyst | Temperature | Catalyst loading | Isolated yield (%) | Time (hrs) |
|---|---|---|---|---|---|
| 1 | AO | 80° C. | 2% + 2% (20 min) | 65 | 0.67 |
| 2 | AP | 80° C. | 2% + 2% (20 min) + 1% (40 min) | 78 | 1.0 |
| 3 | AT | 80° C. | 2% + 2% (20 min) | 75 | 0.67 |
| 4 | AV | 80° C. | 2% + 2% (20 min) + 2% (60 min) | 52 | 1.5 |
| 5 | AW | 80° C. | 2% + 2% (20 min) + 2% (60 min) | 50 | 1.5 |

Synthesis of (1aR,6R,7aS,15aS,Z)-methyl 9-methyl-6-(4-nitrobenzoyloxy)-3,8-dioxo-1a,2,3,5,6,7,7a,8,9,10,11,12,13,15a-tetradecahydro-1H-cyclopropa[m]pyrrolo[1,2-c][1,3,6]triazacyclotetradecine-1a-carboxylate BJ. $^1$H NMR (CDCl$_3$, 400 MHz): δ (ppm) 1.24 (t, J=7.1 Hz, 3H), 1.27-1.35 (m, 1H), 1.37-1.47 (m, 1H), 1.49-1.62 (m, 1H), 1.66-1.79 (m, 3H), 1.87 (br t, J=13.2 Hz, 1H), 2.26-2.47 (m, 2H), 2.60 (br d, J=13.5 Hz, 1H), 3.05 (s, 3H), 3.51 (d, J=9.3 Hz, 1H), 3.94 (dd, J=9.8 and 5.3 Hz, 1H), 4.06-4.16 (m, 1H), 4.18-4.27 (m, 1H), 4.57 (td, J=13.2 and 3.0 Hz, 1H), 5.00 (s, 3H), 5.00-5.05 (m, 1H), 5.48 (t, J=10.3 Hz, 1H), 5.60-5.68 (m, 1H), 5.72 (br s, 1H), 8.20 (d, J=8.8 Hz, 2H), 8.31 (d, J=8.8 Hz, 2H).

Synthesis of (1aR,6S,7aS,15aS,Z)-methyl 6-(7-methoxy-8-methyl-2-(4-(trifluoromethyl)thiazol-2-yl)quinolin-4-yloxy)-9-methyl-3,8-dioxo-1a,2,3,5,6,7,7a,8,9,10,11,12,13,15a-tetradecahydro-1H-cyclopropa[m]pyrrolo[1,2-c][1,3,6]triazacyclotetradecine-1a-carboxylate BL. $^1$H NMR (CDCl$_3$, 400 MHz): δ (ppm) 1.29-1.44 (m, 2H), 1.50-1.62 (m, 2H), 1.66 (s, 1H), 1.68-1.78 (m, 2H), 1.88 (td, J=13.5 and 2.5 Hz, 1H), 2.15-2.23 (m, 1H), 2.40 (dd, J=9.9 and 9.5 Hz, 1H), 2.58 (td, J=13.7 and 3.5 Hz, 1H), 2.68 (s, 3H), 2.97 (td, J=13.3 and 8.4 Hz, 1H), 3.04 (s, 3H), 3.74 (s, 3H), 3.74-3.80 (m, 1H), 3.99 (s, 3H), 4.07 (t, J=7.5 Hz, 1H), 4.62 (td, J=13.4 and 2.9 Hz, 1H), 4.95 (br t, J=6.7 Hz, 1H), 5.07 (s, 1H), 5.41-5.53 (m, 2H), 5.65 (s, J=5.4 Hz, 1H), 7.25 (d, J=9.1 Hz, 1H), 7.51 (s, 1H), 7.87 (s, 1H), 8.02 (d, J=9.1 Hz, 1H); MS (ESI, EE): m/z=687.98 (MH$^+$).

TABLE 6

Compound BL

| Entry | Catalyst | Temp. (° C..) | Catalyst loading | Isolated yield (%) | Time (hrs) |
|---|---|---|---|---|---|
| 1 | AO | 80 | 2% + 2% (1 hr) + 2% (2 hrs) | 51 | 2.5 |
| 2 | AP | 80 | 2% + 2% (1 hr) + 2% (2 hrs) | 49 | 3 |
| 3 | AQ | 80 | 2% + 2% (1 hr) + 2% (2 hrs) | 49 | 2.5 |
| 4 | AR | 80 | 2% + 2% (1 hr) + 2% (2 hrs) | 48 | 2.5 |
| 5 | AS | 80 | 2% + 2% (1 hr) + 2% (2 hrs) | 49 | 2.5 |
| 6 | AT | 80 | 2% + 2% (1 hr) + 2% (2 hrs) | 49 | 3 |
| 7 | AU | 80 | 2% + 2% (1 hr) + 2% (2 hrs) | 43 | 3.5 |
| 8 | C5 | 80 | 2% + 2% (1 hr) + 2% (2 hrs) | 47 | 3 |
| 9 | D4 | 80 | 2% + 2% (1 hr) + 2% (2 hrs) | 38 | 3 |
| 10 | E6 | 80 | 2% + 2% (1 hr) + 2% (2 hrs) | 42 | 3 |
| 11 | G2 | 80 | 2% + 2% (1 hr) + 2% (2 hrs) | 6 | 3.5 |

Synthesis of (Z)-(4R,6S,15S,17S)-[17-[7-methoxy-8-methyl-2-(4-trifluoromethylhiazol-2-yl)quinolin-4-yloxy]-13-N-methyl-2,14-dioxo-1,3,13-triazatricyclo[13.3.0.0]octadec-7-en-4-yl]carbonyl(1-methylcyclopropyl)sulfonamide 68b. $^1$H NMR (CDCl$_1$, 400 MHz): δ (ppm) 0.737 (m, 2H), 1.10-1.21 (m, 2H), 1.26-1.33 (m, 2H), 1.44 (s, 3H), 1.41-1.53 (m, 1H), 1.56-1.65 (m, 1H), 1.71-1.76 (m, 1H), 1.84 (dd, J=6.2 and 8.1 Hz, 2H), 2.11 (dt, J=5.7 and 13.5 Hz, 1H), 2.36 (dd, J=9.3 and 18.9 Hz, 1H), 2.53 (dd, J=3.0 and 13.5 Hz, 1H), 2.61 (s, 3H), 2.81 (ddd, J=4.7, 12.4 and 17.1 Hz, 1H), 2.90-2.96 (m, 1H), 2.98 (s, 3H), 3.73 (dd, J=7.0 and 8.3 Hz, 1H), 3.92 (s, 3H), 3.96 (t, J=7.7, 1H), 4.54 (dd, f=2.6 and 13.7 Hz, 1H), 4.84 (t, J=10.7 Hz, 1H), 4.89 (dd, J=5.3 and 8.9 Hz, 1H), 5.10 (s, 1H), 5.41 (q, J=7.0 Hz, 1H), 5.56 (td, J=5.8 and 10.8 Hz, 1H), 7.18 (d, J=9.2 Hz, 1H), 7.42 (s, 1H), 7.80 (s, 1H), 7.94 (d, J=9.2 Hz, 1H), 11.12 (s, 1H); MS (ESI, Er) m/z=791 (MH$^+$); MS (ESI, EI$^+$) m/z m/z=791 (MH$^+$).

TABLE 7

Compound 68b

| Entry | Cat. | Temp. (° C.) | Catalyst loading | Isolated yield (%) | Time (hrs) |
|---|---|---|---|---|---|
| 1 | AO | 75 | 2% + 2% (45 min) + 2% (2 hrs) | 75 | 4.0 |
| 2 | AP | 60 | 2% + 2% (45 min) + 2% (2 hrs) + 2% (3 hrs) | 45 | 24.0 |
| 3 | AQ | 60 | 2% + 2% (45 min) + 2% (2 hrs) + 2% (3 hrs) | 63 | 24.0 |
| 4 | AR | 60 | 2% + 2% (45 min) + 2% (2 hrs) + 2% (3 hrs) | 30 | 24.0 |
| 5 | AS | 60 | 2% + 2% (45 min) + 2% (2 hrs) + 2% (3 hrs) | 60 | 24.0 |
| 6 | AT | 60 | 2% + 2% (45 min) + 2% (2 hrs) + 2% (3 hrs) | 53 | 24.0 |
| 7 | C5 | 75 | 2% + 2% (45 min) + 2% (2 hrs) | 70 | 4 |
| 8 | D4 | 75 | 2% + 2% (45 min) + 2% (2 hrs) | 77 | 4 |
| 9 | E6 | 75 | 2% + 2% (45 min) + 2% (2 hrs) | 70 | 4 |
| 10 | G2 | 75 | 2% + 2% (45 min) + 2% (2 hrs) | 12 | 4 |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A ruthenium complex of Formula I:

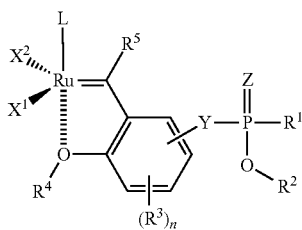

(I)

wherein:

L is a neutral ligand;

$R^1$ is $C_{1-12}$ alkyl, $C_{3-10}$ cycloalkyl, $C_{6-14}$ aryl, heteroaryl, heterocyclyl, or —$NR^{3b}R^{3c}$;

$R^2$ is H, $C_{1-12}$ alkyl, $C_{3-10}$ cycloalkyl, or $C_{6-14}$ aryl;

$R^3$ is halo, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)$R^{3a}$, —C(O)O$R^{3a}$, —C(O)N$R^{3b}R^{3c}$, —O$R^{3a}$, —N$R^{3b}R^{3c}$, —N$R^{3a}$C(O)$R^{3b}$, —N$R^{3a}$C(O)O$R^{3b}$, —N$R^{3a}$S(O)$_2R^{3b}$, —P$R^{3a}R^{3b}$, —P(O$R^{3a}$)$R^{3b}$, —P(O$R^{3a}$)(O$R^{3b}$), —P(O)$R^{3a}R^{3b}$, —P(O)(O$R^{3a}$)$R^{3b}$, —P(O)(O$R^{3a}$)(O$R^{3b}$), —S(O)$_2R^{3a}$, or —SO$_2$N$R^{3b}R^{3c}$, $R^4$ is $C_{1-12}$ alkyl, $C_{3-10}$ cycloalkyl, $C_{7-15}$ aralkyl, or —C($R^{4a}R^{4b}$)C(O)N$R^{4c}R^{4d}$;

$R^5$ is hydrogen, $C_{1-12}$ alkyl, $C_{2-12}$ alkenyl, $C_{2-12}$ alkynyl, $C_{3-10}$ cycloalkyl, or $C_{6-14}$ aryl;

each $R^{3a}$ and $R^{3d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each $R^{3b}$ and $R^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^{3b}$ and $R^{3c}$ together with the N atom form a heteroaryl or heterocyclyl;

$R^{4a}$ and $R^{4b}$ are each independently hydrogen, $C_{1-6}$ alkyl, $C_{3-8}$ cycloalkyl, $C_{6-14}$ aryl, or $C_{7-15}$ aralkyl;

$R^{4c}$ and $R^{4d}$ are each independently hydrogen, $C_{1-6}$ alkyl, $C_{3-8}$ cycloalkyl, $C_{6-14}$ aryl, or $C_{7-15}$ aralkyl; or $R^{4c}$ and $R^{4d}$ together with the N atom form heterocyclyl;

$X^1$ and $X^2$ are each independently an anionic ligand;

Y is a bond or —$NR^b$—;

Z is O or S; and n is an integer of 0, 1, 2, or 3;

wherein each alkyl, alkenyl, alkynyl, aryl, aralkyl, cycloalkyl, heterocyclyl, and heteroaryl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents Q; or (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —P$R^aR^d$, —P(O$R^a$)$R^d$, —P(O$R^a$)(O$R^d$), —P(O)$R^aR^d$, —P(O)(O$R^a$)$R^d$, —P(O)(O$R^a$)(O$R^d$), —S$R^a$, —S(O)$R^a$, —S(O)$_2R^a$, or —SO$_2$N$R^bR^c$; wherein each $R^a$, $R^b$, $R^c$, and $R^d$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents Q; or $R^b$ and $R^c$ together with the N atom to which they are attached form heterocyclyl, optionally substituted with one or more substituents Q;

wherein each Q is independently selected from the group consisting of (i) cyano, halo, or nitro; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —P$R^eR^h$, —P(O$R^e$)$R^h$, —P(O$R^e$)(O$R^h$), —P(O)$R^eR^h$, —P(O)(O$R^e$)$R^h$, —P(O)(O$R^e$)(O$R^h$), —S$R^e$, —S(O)$R^e$, —S(O)$_2R^e$, or —S(O)$_2$N$R^fR^g$; wherein each $R^e$, $R^f$, $R^g$, and $R^h$ is independently hydrogen; $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^f$ and $R^g$ together with the N atom to which they are attached form heterocyclyl.

2. The ruthenium complex of claim 1 having Formula Ia:

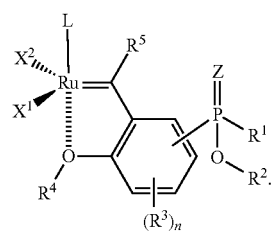

(Ia)

3. The ruthenium complex of claim 1 having Formula Ib:

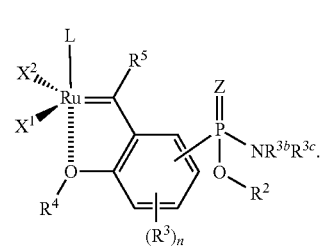

(Ib)

4. The ruthenium complex of claim 1 having Formula Ic:

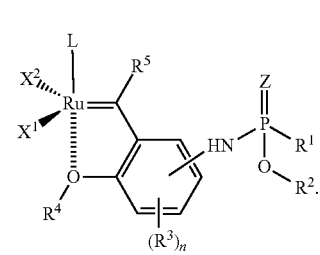

(Ic)

5. The ruthenium complex of claim 1, wherein L is a heterocyclic carbene or phosphine, wherein the heterocyclic carbene is optionally substituted with one or more substituents.

6. The ruthenium complex of claim 5, wherein the heterocyclic carbene is selected from the group consisting of:

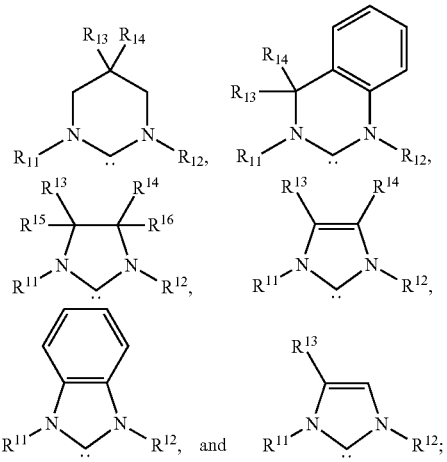

wherein:
   each $R^{11}$ and $R^{12}$ is independently $C_{1-6}$ alkyl or $C_{6-14}$ aryl; and
   each $R^{13}$, $R^{14}$, $R^{15}$, and $R^{16}$ is independently hydrogen, cyano, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;
   wherein each alkyl, alkenyl, alkynyl, aryl, cycloalkyl, heterocyclyl, and heteroaryl is optionally substituted with one or more substituents.

7. The ruthenium complex of claim 6, wherein $R^{13}$ or $R^{15}$ is hydrogen or methyl.

8. The ruthenium complex of claim 6, wherein $R^{14}$ or $R^{16}$ is hydrogen or methyl.

9. The ruthenium complex of claim 6, wherein $R^{11}$ is $C_{6-14}$ aryl.

10. The ruthenium complex of claim 6, wherein $R^{11}$ is $C_{6-14}$ aryl, substituted with one or more $C_{1-6}$ alkyl.

11. The ruthenium complex of claim 10, wherein $R^{11}$ is 2-methylphenyl, 2,4,6-trimethylphenyl, or 2,6-di(isopropyl)phenyl.

12. The ruthenium complex of claim 6, wherein $R^{12}$ is $C_{6-14}$ aryl.

13. The ruthenium complex of claim 6, wherein $R^{12}$ is $C_{6-14}$ aryl, substituted with one or more $C_{1-6}$ alkyl.

14. The ruthenium complex of claim 13, wherein $R^{12}$ is 2-methylphenyl, 2,4,6-trimethylphenyl, or 2,6-di(isopropyl)phenyl.

15. The ruthenium complex of claim 6, wherein the heterocyclic carbene is selected from the group consisting of:

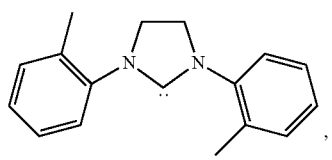

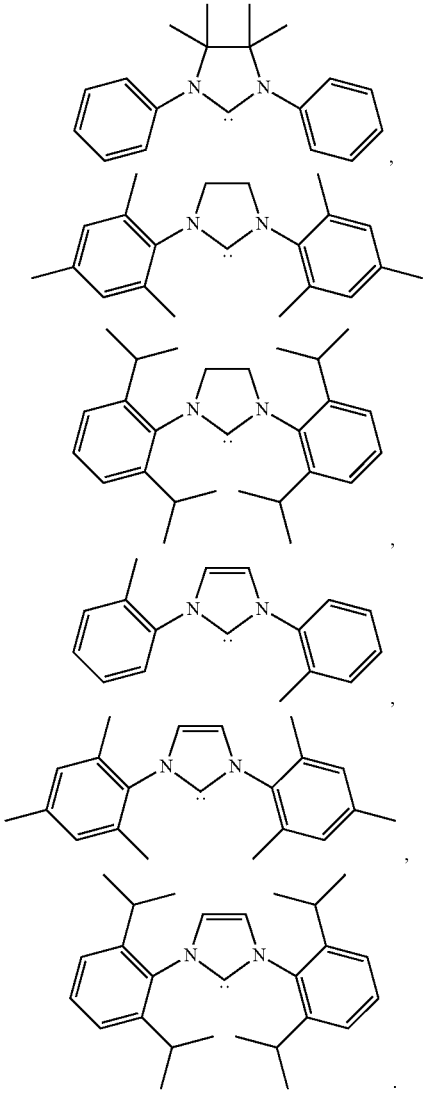

16. The ruthenium complex of claim 5, wherein the phosphine is $PR^{17}R^{18}R^{19}$, wherein $R^{17}$, $R^{18}$, and $R^{19}$ are each independently $C_{1-12}$ alkyl or $C_{6-14}$ aryl, each optionally substituted with one or more substituents.

17. The ruthenium complex of claim 16, wherein $R^{17}$ is phenyl or cyclohexyl.

18. The ruthenium complex of claim 16, wherein $R^{18}$ is phenyl or cyclohexyl.

19. The ruthenium complex of claim 16, wherein $R^{19}$ is phenyl or cyclohexyl.

20. The ruthenium complex of claim 16, wherein the phosphine is triphenylphosphine or tricyclohexylphosphine.

21. The ruthenium complex of claim 1, wherein $X^1$ is halide, $-C(O)R^x$, or $-OC(O)R^x$, wherein $R^x$ is alkyl, optionally substituted with one or more halides.

22. The ruthenium complex of claim 21, wherein $X^1$ is chloride.

23. The ruthenium complex of claim 1, wherein $X^2$ is halide, $-C(O)R^x$, or $-OC(O)R^x$, wherein $R^x$ is alkyl, optionally substituted with one or more halides.

24. The ruthenium complex of claim 23, wherein $X^2$ is chloride.

25. The ruthenium complex of claim 1, wherein $R^1$ is $C_{1-5}$ alkyl, $C_{5-6}$ cycloalkyl, $C_{6-14}$ aryl, heteroaryl, heterocyclyl, or $-NR^{3b}R^{3c}$.

26. The ruthenium complex of claim 25, wherein $R^1$ is trifluoromethyl, phenyl, cyanophenyl, fluorophenyl, difluorophenyl, trifluoromethylphenyl, bis(trifluoromethyl)phenyl, trifluoromethylsulfonylphenyl, trifluoroacetylphenyl, nitrophenyl, dinitrophenyl, trifluoroacetamidophenyl, methoxyphenyl, pentofluorophenyl, pyridyl, trifluoromethyl-thiazolyl, trifluoromethyl-pyrazolyl, or dimethylamino.

27. The ruthenium complex of claim 25, wherein $R^1$ is phenyl, 4-cyanophenyl, 4-fluorophenyl, 3,5-difluorophenyl, 4-trifluoromethylphenyl), 3,5-bis(trifluoromethyl)phenyl, 4-trifluoromethylsulfonylphenyl, 4-trifluoroacetylphenyl, 4-nitrophenyl, 3,5-dinitrophenyl, 4-trifluoroacetamidophenyl, 4-methoxyphenyl, pentofluorophenyl, pyridyl, 4-trifluoromethylthiazolyl, or 3-trifluoromethyl-pyrazolyl, or dimethylamino.

28. The ruthenium complex of claim 25, wherein $R^1$ is phenyl, 4-fluorophenyl, 3,5-difluorophenyl, 4-trifluoromethylphenyl, 4-methoxyphenyl, or dimethylamino.

29. The ruthenium complex of claim 1, wherein $R^2$ is $C_{1-5}$ alkyl or $C_{5-6}$ cycloalkyl.

30. The ruthenium complex of claim 29, wherein $R^2$ is ethyl.

31. The ruthenium complex of claim 1, wherein $R^3$ is halo, cyano, nitro, $-C(O)OR^{3a}$, $-NR^{3a}S(O)_2R^{3b}$, $-P(O)(OR^{3a})R^{3b}$, or $-SO_2NR^{3b}R^{3c}$.

32. The ruthenium complex of claim 1, wherein $R^4$ is $C_{1-5}$ alkyl or $C_{5-6}$ cycloalkyl.

33. The ruthenium complex of claim 32, wherein $R^4$ is isopropyl.

34. The ruthenium complex of claim 1, wherein $R^5$ is hydrogen, $C_{1-5}$ alkyl, or $C_{5-6}$ cycloalkyl.

35. The ruthenium complex of claim 34, wherein $R^5$ is hydrogen.

36. The ruthenium complex of claim 1, wherein Z is O.

37. The ruthenium complex of claim 1, wherein n is 0.

38. The ruthenium complex of claim 1, wherein the complex is selected from the group consisting of:

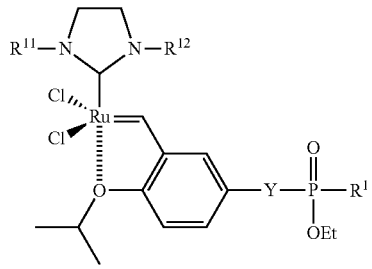

wherein:

| Cmpd No. | Y | $R^1$ | $R^{11}$ | $R^{12}$ |
|---|---|---|---|---|
| AP | A bond | *—C₆H₄—CF₃ | Mes | Mes |
| AQ | A bond | *—C₆H₅ | Mes | Mes |
| AR | A bond | *—C₆H₄—F | Mes | Mes |
| AT | A bond | *—C₆H₃(CF₃)₂ | Mes | Mes |
| C5 | A bond | $-N(CH_3)_2$ | Mes | Mes |
| D4 | A bond | *—C₆H₄—OCH₃ | Mes | Mes |
| E6 | —NH— | *—C₆H₅ | Mes | Mes |
| G2 | A bond | *—C₆H₅ | 2-MePh | 2-MePh. |

* * * * *